US010387020B2

(12) United States Patent
Cauwels et al.

(10) Patent No.: US 10,387,020 B2
(45) Date of Patent: Aug. 20, 2019

(54) DISPLAY DEVICE, CORRESPONDING SYSTEMS, AND METHODS THEREFOR

(71) Applicant: Google Technology Holdings LLC, Mountain View, CA (US)

(72) Inventors: Patrick Cauwels, South Beloit, IL (US); Rachid M. Alameh, Crystal Lake, IL (US); Timothy Dickinson, Crystal Lake, IL (US); Phillip D. Rasky, Buffalo Grove, IL (US); Paul R. Steuer, Hawthorn Woods, IL (US)

(73) Assignee: Google Technology Holdings LLC, Mountain View, CA (US)

(*) Notice: Subject to any disclaimer, the term of this patent is extended or adjusted under 35 U.S.C. 154(b) by 0 days.

(21) Appl. No.: 15/876,860

(22) Filed: Jan. 22, 2018

(65) Prior Publication Data
US 2018/0157401 A1 Jun. 7, 2018

Related U.S. Application Data

(60) Continuation of application No. 15/336,060, filed on Oct. 27, 2016, now Pat. No. 9,875,008, which is a (Continued)

(51) Int. Cl.
*G06F 3/048* (2013.01)
*G06F 1/16* (2006.01)
(Continued)

(52) U.S. Cl.
CPC ............ *G06F 3/04845* (2013.01); *A61B 5/01* (2013.01); *A61B 5/024* (2013.01);
(Continued)

(58) Field of Classification Search
CPC ................. G06F 1/163; G06F 3/04845; G06F 2200/1614; G06F 2200/1637;
(Continued)

(56) References Cited

U.S. PATENT DOCUMENTS 4,985,878 A 1/1991 Yamada et al.
5,416,730 A 5/1995 Lookofsky
(Continued)

FOREIGN PATENT DOCUMENTS

DE 102009003128 11/2010
EP 1225751 7/2002
(Continued)

OTHER PUBLICATIONS

"Advisory Action", U.S. Appl. No. 13/893,533, dated Sep. 14, 2016, 3 pages.
(Continued)

*Primary Examiner* — Omar Casillashernandez
(74) *Attorney, Agent, or Firm* — Colby Nipper

(57) ABSTRACT

A display system includes a display and a control circuit operable with the display. The display is configured to provide visual output having a presentation orientation. When user input is received, the control circuit can alter the presentation orientation from an initial orientation in response to user input. When non-user events or device events are detected, the control circuit can revert the presentation orientation to the initial orientation in response to the non-user event or device event. Where the presentation orientation has a user input configuration associated therewith, the user input configuration can either be altered with the presentation orientation or retained in an initial disposition.

20 Claims, 43 Drawing Sheets

Related U.S. Application Data continuation of application No. 14/474,808, filed on Sep. 2, 2014, now abandoned, which is a division of application No. 13/297,662, filed on Nov. 16, 2011, now abandoned.

(51) Int. Cl.

| | | |
|---|---|---|
| *G06F 3/0484* | (2013.01) | |
| *A61B 5/01* | (2006.01) | |
| *A61B 5/024* | (2006.01) | |
| *A61B 5/00* | (2006.01) | |
| *A61B 5/145* | (2006.01) | |
| *G06F 3/0488* | (2013.01) | |
| *A61B 5/0402* | (2006.01) | |
| *A61B 5/053* | (2006.01) | |
| *G06F 3/0485* | (2013.01) | |

(52) U.S. Cl.
CPC ........ *A61B 5/14532* (2013.01); *A61B 5/4266* (2013.01); *A61B 5/681* (2013.01); *A61B 5/6898* (2013.01); *A61B 5/7475* (2013.01); *G06F 1/163* (2013.01); *G06F 3/04883* (2013.01); *A61B 5/0402* (2013.01); *A61B 5/0531* (2013.01); *G06F 3/0485* (2013.01); *G06F 2200/1614* (2013.01); *G06F 2200/1637* (2013.01)

(58) Field of Classification Search
CPC ........... A61B 5/681; A61B 5/01; A61B 5/024; A61B 5/0531; A61B 5/0402; A61B 5/14532; A61B 5/6898; A61B 5/7475
USPC .............................................. 340/3.1; 715/79
See application file for complete search history.

(56) References Cited

U.S. PATENT DOCUMENTS

| | | | |
|---|---|---|---|
| 5,479,285 A | 12/1995 | Burke | |
| 5,625,697 A | 4/1997 | Bowen et al. | |
| 5,872,744 A | 2/1999 | Taylor | |
| 5,889,737 A | 3/1999 | Alameh et al. | |
| 6,158,884 A | 12/2000 | Lebby et al. | |
| 6,198,394 B1* | 3/2001 | Jacobsen | A61B 5/1112 340/573.1 |
| 6,352,152 B1 | 3/2002 | Anderson et al. | |
| 6,382,448 B1 | 5/2002 | Yuhara et al. | |
| 6,525,997 B1 | 2/2003 | Narayanaswami et al. | |
| 6,528,203 B1 | 3/2003 | Mitamura | |
| 6,771,237 B1 | 8/2004 | Kalt | |
| 7,224,963 B2 | 5/2007 | Anderson et al. | |
| 7,259,155 B2 | 8/2007 | Sakai et al. | |
| 7,401,758 B2 | 7/2008 | Liang et al. | |
| 7,623,780 B2 | 11/2009 | Takita | |
| 7,766,517 B2 | 8/2010 | Kerr et al. | |
| 7,953,463 B2 | 5/2011 | Misawa | |
| 8,207,936 B2 | 6/2012 | Gustafsson et al. | |
| 8,359,020 B2 | 1/2013 | Lebeau et al. | |
| 8,456,586 B2 | 6/2013 | Matthew et al. | |
| 8,517,896 B2 | 8/2013 | Robinette et al. | |
| 8,675,124 B2 | 3/2014 | Kawakami | |
| 8,817,048 B2 | 8/2014 | Kerr et al. | |
| 9,009,984 B2 | 4/2015 | Caskey et al. | |
| 9,201,454 B2 | 12/2015 | Haupt et al. | |
| 9,484,001 B2 | 11/2016 | Dabhi | |
| 9,622,365 B2 | 4/2017 | Allore et al. | |
| 9,674,922 B2 | 6/2017 | Malon et al. | |
| 9,875,008 B2 | 1/2018 | Cauwels et al. | |
| 2001/0043514 A1* | 11/2001 | Kita | A44C 5/0015 368/281 |
| 2002/0103014 A1 | 8/2002 | Hutchison et al. | |
| 2003/0103091 A1 | 6/2003 | Wong et al. | |
| 2003/0158593 A1 | 8/2003 | Heilman et al. | |
| 2004/0056845 A1 | 3/2004 | Harkcom et al. | |
| 2004/0133081 A1* | 7/2004 | Teller | A61B 5/01 600/300 |
| 2004/0250933 A1 | 12/2004 | Demichele | |
| 2005/0285811 A1 | 12/2005 | Kawase et al. | |
| 2007/0103908 A1 | 5/2007 | Tabito et al. | |
| 2007/0273609 A1 | 11/2007 | Yamaguchi et al. | |
| 2008/0001971 A1 | 1/2008 | Kouninski | |
| 2008/0074551 A1 | 3/2008 | Kawakami | |
| 2008/0094515 A1 | 4/2008 | Gutta et al. | |
| 2008/0204367 A1 | 8/2008 | Lafarre et al. | |
| 2008/0258917 A1* | 10/2008 | Boyd | A63B 24/0062 340/572.1 |
| 2008/0285290 A1 | 11/2008 | Ohashi et al. | |
| 2008/0291225 A1 | 11/2008 | Arneson | |
| 2008/0303681 A1 | 12/2008 | Herz et al. | |
| 2008/0303782 A1 | 12/2008 | Grant et al. | |
| 2008/0309589 A1 | 12/2008 | Morales | |
| 2008/0309861 A1 | 12/2008 | Seki et al. | |
| 2009/0177068 A1* | 7/2009 | Stivoric | A61B 5/01 600/365 |
| 2009/0195959 A1 | 8/2009 | Ladouceur et al. | |
| 2009/0254869 A1 | 10/2009 | Ludwig et al. | |
| 2009/0322513 A1* | 12/2009 | Hwang | A61B 5/02055 340/539.12 |
| 2010/0007510 A1 | 1/2010 | Ina et al. | |
| 2010/0029327 A1* | 2/2010 | Jee | G04G 17/045 455/556.1 |
| 2010/0053174 A1 | 3/2010 | Cohen et al. | |
| 2010/0056223 A1 | 3/2010 | Choi et al. | |
| 2010/0225600 A1 | 9/2010 | Dai et al. | |
| 2010/0231692 A1 | 9/2010 | Perlman et al. | |
| 2010/0238367 A1 | 9/2010 | Montgomery et al. | |
| 2010/0265431 A1 | 10/2010 | Li | |
| 2010/0328571 A1 | 12/2010 | Itaya | |
| 2011/0109538 A1 | 5/2011 | Kerr et al. | |
| 2011/0221656 A1 | 9/2011 | Haddick et al. | |
| 2011/0242750 A1 | 10/2011 | Oakley | |
| 2011/0255303 A1 | 10/2011 | Nichol et al. | |
| 2012/0038613 A1 | 2/2012 | Choi | |
| 2012/0044131 A1 | 2/2012 | Nussbacher et al. | |
| 2012/0055553 A1 | 3/2012 | Logunov et al. | |
| 2012/0071099 A1* | 3/2012 | Okinoi | G06K 7/00 455/41.2 |
| 2012/0091923 A1 | 4/2012 | Kastner-Jung et al. | |
| 2012/0112994 A1 | 5/2012 | Vertegaal et al. | |
| 2012/0177953 A1 | 7/2012 | Bhardwaj et al. | |
| 2012/0242592 A1 | 9/2012 | Rothkopf et al. | |
| 2013/0053661 A1 | 2/2013 | Alberth et al. | |
| 2013/0076649 A1 | 3/2013 | Myers et al. | |
| 2013/0120106 A1* | 5/2013 | Cauwels | G06F 1/163 340/3.1 |
| 2013/0127733 A1 | 5/2013 | Krishnaswamy | |
| 2013/0278631 A1 | 10/2013 | Border et al. | |
| 2013/0307419 A1 | 11/2013 | Simonian et al. | |
| 2013/0329460 A1 | 12/2013 | Mathew et al. | |
| 2014/0063055 A1 | 3/2014 | Osterhout et al. | |
| 2014/0088387 A1 | 3/2014 | Hu et al. | |
| 2014/0063049 A1 | 6/2014 | Armstrong-Muntner | |
| 2014/0240903 A1 | 8/2014 | Allore et al. | |
| 2014/0265821 A1 | 9/2014 | Malon | |
| 2014/0285967 A1 | 9/2014 | Wikander et al. | |
| 2014/0368981 A1 | 12/2014 | Haupt et al. | |
| 2014/0372940 A1 | 12/2014 | Cauwels et al. | |
| 2015/0138505 A1 | 5/2015 | Grenon et al. | |
| 2015/0179141 A1 | 6/2015 | Dabhi | |
| 2017/0046054 A1 | 2/2017 | Cauwels et al. | |

FOREIGN PATENT DOCUMENTS

| | | |
|---|---|---|
| EP | 2500898 | 9/2012 |
| GB | 2327012 | 1/1999 |
| WO | 9624093 | 8/1996 |
| WO | 0025193 | 5/2000 |
| WO | 2008057143 | 5/2008 |
| WO | 2011121403 | 10/2011 |

(56) References Cited

FOREIGN PATENT DOCUMENTS

OTHER PUBLICATIONS

"Advisory Action", U.S. Appl. No. 14/474,808, dated Sep. 19, 2016, 2 pages.
"Corrected Notice of Allowance", U.S. Appl. No. 13/893,533, dated Jan. 12, 2017, 5 pages.
"Final Office Action", U.S. Appl. No. 14/034,860, 10 pages.
"Final Office Action", U.S. Appl. No. 13/455,921, dated Jun. 13, 2014, 18 pages.
"Final Office Action", U.S. Appl. No. 13/893,533, dated Jul. 30, 2015, 15 pages.
"Final Office Action", U.S. Appl. No. 13/455,921, dated Oct. 7, 2015, 19 pages.
"Final Office Action", U.S. Appl. No. 14/139,485, dated Oct. 16, 2015, 11 pages.
"Final Office Action", U.S. Appl. No. 13/893,533, dated May 5, 2016, 22 pages.
"Final Office Action", U.S. Appl. No. 14/474,808, dated Jun. 2, 2016, 15 pages.
"Final Office Action", U.S. Appl. No. 14/139,485, dated Jul. 7, 2016, 5 pages.
"International Preliminary Report on Patentability", Application No. PCT/US2013/034760, dated Nov. 6, 2014, 10 pages.
"International Search Report and the Written Opinion", Application No. PCT/US2012/064300, dated Apr. 11, 2013, 14 pages.
"International Search Report and the Written Opinion", Application No. PCT/US2013/034760, dated Jun. 28, 2013, 13 pages.
"International Search Report and the Written Opinion", Application No. PCT/US2014/012739, dated May 9, 2014, 11 pages.
"International Search Report and Written Opinion", Application No. PCT/US2014/017331, dated Sep. 1, 2014, 15 pages.
"Non-Final Office Action", U.S. Appl. No. 13/455,921, dated Dec. 18, 2013, 15 pages.
"Non-Final Office Action", U.S. Appl. No. 13/297,662, dated Jun. 2, 2014, 12 pages.
"Non-Final Office Action", U.S. Appl. No. 13/455,921, dated Feb. 24, 2015, 17 pages.
"Non-Final Office Action", U.S. Appl. No. 13/893,533, dated Mar. 2, 2015, 14 pages.
"Non-Final Office Action", U.S. Appl. No. 14/139,485, dated May 26, 2015, 10 pages.
"Non-Final Office Action", U.S. Appl. No. 13/893,533, dated Dec. 18, 2015, 22 pages.
"Non-Final Office Action", U.S. Appl. No. 14/474,808, dated Jan. 12, 2016, 9 pages.
"Non-Final Office Action", U.S. Appl. No. 14/139,485, dated Mar. 10, 2016, 11 pages.
"Notice of Allowance", U.S. Appl. No. 15/336,060, dated Oct. 16, 2017, 14 pages.
"Notice of Allowance", U.S. Appl. No. 14/082,733, dated Feb. 18, 2015, 7 pages.
"Notice of Allowance", U.S. Appl. No. 14/082,733, dated Jul. 27, 2015, 7 pages.
"Notice of Allowance", U.S. Appl. No. 13/893,533, dated Dec. 2, 2016, 8 pages.
"Notice of Allowance", U.S. Appl. No. 14/034,860, dated Jan. 17, 2017, 8 pages.
"Restriction Requirement", U.S. Appl. No. 13/297,662, dated Nov. 14, 2013, 5 pages.
"Restriction Requirement", U.S. Appl. No. 14/034,860, dated Sep. 4, 2015, 11 pages.
"Supplemental Notice of Allowance", U.S. Appl. No. 14/034,860, dated May 12, 2017, 2 pages.
Kee, "Bendable batteries in the pipeline?", Ubergizmo, http//:www.ubergizmo.com/2011/02/bendable-batteries-in-the-pipeline/, Feb. 28, 2011, 2 pages.
Tan, "Exploiting the Cognitive and Social Benefits of Physically Large Displays", Carnigie Mellon University CMU-CS-04-154, 201 pages.

* cited by examiner

DISPLAY DEVICE, CORRESPONDING SYSTEMS, AND METHODS THEREFOR

RELATED APPLICATIONS

This patent application is a continuation of and claims priority to copending U.S. patent application Ser. No. 15/336,060, filed on Oct. 27, 2016, which in turn claims priority to U.S. patent application Ser. No. 14/474,808, filed on Sep. 2, 2014, which in turn claims priority to U.S. patent application Ser. No. 13/297,662, filed Nov. 16, 2011, the disclosures of which are incorporated herein by reference in their entirety.

BACKGROUND

Technical Field

This invention relates generally to user interfaces, and more particularly to devices, methods, and systems for orienting information on user interfaces and displays.

Background Art

Electronic devices, such as mobile telephones, smart phones, gaming devices, and the like, present information to users on a display. As these devices have become more sophisticated, so too have their displays and the information that can be presented on them. For example, not too long ago a mobile phone included a rudimentary light emitting diode display capable of only presenting numbers and letters configured as seven-segment characters. Today, high resolution liquid crystal and other displays included with mobile communication devices and smart phones can be capable of presenting high resolution video.

The display output is generally oriented so as to be aligned with the device. Said differently, many electronic devices have an identifiable top and bottom. Display output is aligned in a complementary manner, with the top of the display output appearing towards the identifiable top of the device, and the bottom of the display output being aligned with the bottom of the device.

Some devices allow the display output to be rotated. For example, some devices have a gravity detector that is configured to rotate the output based on a detected gravitational field. Thus, as the device is rotated, the "top" of the output always stays above the bottom of the output.

While rotating display output based on gravity can be useful, it fails to provide suitable display output alignment in all situations. It would be advantageous to have an improved display device with improved display orientation capabilities.

Figure 1:
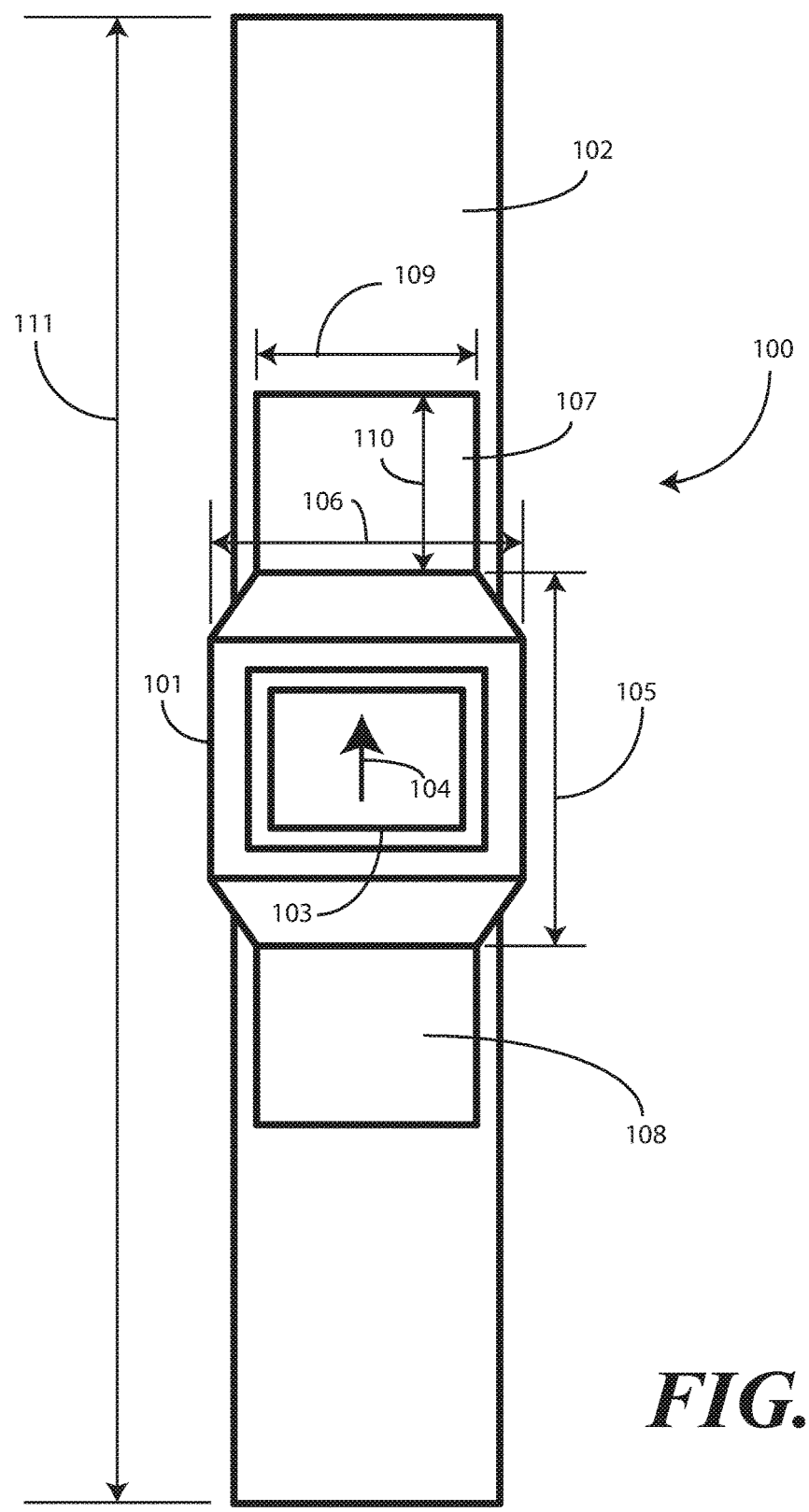
FIG. 1 illustrates one explanatory electronic device configured in accordance with one or more embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Before describing in detail embodiments that are in accordance with the present invention, it should be observed that the embodiments reside primarily in combinations of method steps and apparatus components related to altering a presentation orientation of visual indicia on a display in response to user input and then reverting the presentation orientation to an initial orientation in response to a device event, which can be a non-user initiated event. Any process descriptions or blocks in flow charts should be understood as representing modules, segments, or portions of code that include one or more executable instructions for implementing specific logical functions or steps in the process. Alternate implementations are included, and it will be clear that functions may be executed out of order from that shown or discussed, including substantially concurrently or in reverse order, depending on the functionality involved. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

It will be appreciated that embodiments of the invention described herein may be comprised of one or more conventional processors and unique stored program instructions that control the one or more processors to implement, in conjunction with certain non-processor circuits, some, most, or all of the functions of altering and reverting presentation orientations of data presented on a display as described herein. The non-processor circuits may include, but are not limited to, a radio receiver, a radio transmitter, signal drivers, clock circuits, power source circuits, and user input devices. As such, these functions may be interpreted as steps of a method to perform presentation orientation alteration and reversion. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used. Thus, methods and means for these functions have been described herein. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

From an electrical perspective, embodiments described below provide a display system, suitable for integration into an electronic device, configured to alter a presentation orientation of visual output. One explanatory electronic device used in the figures is a wearable device configured as a wristwatch. However, it will be clear to those of ordinary skill in the art having the benefit of this disclosure that the display systems, control circuits, and associated modules used to alter the presentation orientation could be integrated into any of a number of portable electronic devices, including mobile telephones, personal digital assistants, smart phones, palm-top computers, tablet devices, portable computers, and so forth.

The display is configured to present visual output having a presentation orientation. The presentation orientation refers to how the visual output is oriented relative to either the earth or the electronic device itself. For example, when the electronic device is held vertically with its top above its bottom, a presentation orientation with reference to the earth can be more useful and appropriate. If the visual output is presented with the top of the content being nearer the top of the device, the presentation orientation can be considered to be "right side up." Similarly, of the visual output is presented with the top of the content below the bottom of the content, the presentation orientation can be considered to be "upside down." These references can be without reference to the device itself. In this example the reference to the earth can be determined by using sensors that detect acceleration due to the earth's gravity such as accelerometers, or with gyroscopes that detect a change in motion of the device.

However, when the electronic device is held horizontally, the effect of gravity on accelerometers in the device remains relatively constant. In this case an alternative method would need to be used to detect a reorientation of the device. When the top of presented content is nearer the first side of the device, a first presentation orientation is established. When the presented content is altered such that the top of the content becomes nearer a second side, a second presentation orientation is established. In this example, the reference to the earth can be determined with using a sensor that detects the earth's magnetic field such as an electronic compass or changes in position and orientation using methods such as GPS location or gyroscopes. In this example, the first presentation orientation can remain constant in space even though the device is translated or rotated.

Alternatively, the presentation orientation can be referenced to the electronic device. When the top of presented content is nearer the first side of the device, a first presentation orientation is established. When the presented content is altered such that the top of the content becomes nearer a second side, a second presentation orientation is established such that the top of the presented content is always disposed toward the side of the device that is on "top" in the given orientation. As with the earth-referenced cases, the device can be held horizontally or vertically.

When the display initially presents visual output, it has an initial presentation orientation. A control circuit that is operable with the display can then be configured to alter the presentation orientation in response to user input. For example, if the display is a touch sensitive display, the user may swipe a finger or stylus across the display to rotate the display to a second presentation orientation. For instance, a user may be holding a tablet-style computer horizontally, with the user's body located on a first side of the tablet-style computer. A friend may be standing near the tablet-style computer, with the friend's body being positioned on a second side of the tablet-style computer opposite the first side. When the user wants to show a picture being presented as visual output from the display to the friend that has a "correct" presentation orientation for the friend, the user may make a rotating motion along the display to rotate the picture such that the top of the picture, initially disposed towards the friend, rotates 180 degrees to be nearer the user. In response to this user input, the control circuit alters the presentation orientation from the initial orientation to a second orientation, which is rotated 180 degrees from the initial orientation.

In another embodiment, a user may swipe a touch sensitive display in the direction of their friend by "drawing" a line beginning at user's side and ending at friend's side. In another embodiment, rotation of content can be achieved by tilting device toward the friend while center of the device is held stationary in three-dimensional space. This distinguishes the tilting from random user hand movements, walking, or other motion. As an example, a user can tilt the device toward a friend who is standing in front of the user. The upper side of the device, now pointing away from user, can represent the upper side of the rotated content presented to the friend.

In one or more embodiments, the control circuit is then configured to revert the presentation orientation back to the initial orientation in response to a non-user event or, alternatively, a user event such as a second sweep of a finger or stylus across the display. Non-user input can refer to input other than intentional display manipulation actions like the finger sweep described in the preceding paragraph. For example, an incoming email or text message received via wireless communication would be one example of non-user input. Similarly, an incoming call is an example of non-user input as well.

In some embodiments, non-user input can include passively detected conditions pertaining to the user. For example, as will be described below, in one or more embodiments wellness sensors can be disposed within an electronic device configured with display alteration capabilities. These wellness sensors can detect conditions such as pulse, temperature, heartbeat, perspiration, or other conditions. In such applications, non-user input can be extended to include sensed wellness conditions such as increased or abnormal heartbeat, increased or abnormal pulse, or increased perspiration, increased or decreased temperature, abnormal blood sugar levels, and the like. When one of these conditions is sensed, the control circuit can be configured to revert the presentation orientation back from a user-manipulated orientation to the initial orientation.

From a mechanical perspective, in one embodiment a detachable module of the electronic device includes a first electronic module extension extending distally from a first side of a housing of the electronic device. A second electronic module extension extends distally from a second side of the housing. In one embodiment, the second side of the housing is disposed opposite the first side such that the first electronic module extension and the second electronic module extension extend out of opposite sides of the housing, or outward from the housing in directions that are separated radially by 180 degrees.

In one or more embodiments, both the first electronic module extension and the second electronic module extension are hingedly coupled to the housing. The hinged connection can be via a simple hinge, a biased hinge having a pre-loaded force member, a detented hinge, or combinations of these. The hinged connection is configured to allow the first electronic module extension and the second electronic module extension to selectively pivot to any number of angularly displaced orientations ranging from a closed position, where either the electronic module extension is disposed against a major face of the housing, to an angularly displaced open position, where the electronic module extension is extending distally outward from the housing.

In one or more embodiments, electronic circuitry and components for the electronic module are disposed exclusively within the housing with a single exception: an energy storage device, such as a lithium polymer battery, and accompanying power delivery circuitry (including energy storage device safety and charging circuitry) is disposed within one or both electronic module extensions. In such a configuration, the energy storage device disposed within the electronic module extension(s) is coupled through the hinge to the electronic circuitry and components disposed within the housing, and can accordingly supply power to the electronic components disposed exclusively within the housing. While the electronic module extensions contain energy storage devices, one or more smaller energy storage devices can be disposed in the housing as well.

The electronic module extensions can be configured in a variety of form factors, with each form factor having an aesthetic component, a functional component, or combinations thereof. For example, in one embodiment the electronic module extensions can be configured in a planar configuration so as to form radial extensions from the housing. The electronic module extensions containing the energy storage devices can be electrically coupled in parallel or series. For the series configuration, control circuitry can be added to selectively switch energy storage devices in or out of the circuit based upon stored energy state. In another embodiment, the electronic module extensions can be configured with a non-planar geometry, such as an arched shape (when viewed in cross section). Where energy sources are disposed within the electronic module extensions, the energy sources can be configured to conform to the form factor of the electronic module extension. Illustrating by example, where the electronic module extension is arched, a lithium polymer cell can be formed as an arch so as to be complementary to the form factor of the electronic module extension. Such a cell can be constructed on an arched form to result in the arched cell. Alternatively, a planar lithium polymer cell can be arched after construction so as to be complementary to the form factor of the electronic module extension. Compliant batteries can be used instead to form bendable, compliant electronic module extensions. For instance, a user with small wrist might want to bend the compliant battery/electronic module extension to provide a better fit. Accordingly, the compliant batteries can be covered with a finish that does not restrict bending. Alternatively, the compliant batteries can be housed inside a flexible housing made from flexible material such as rubber, plastic, or even hard material with embedded features enabling it to bend, such as via hinged links. While some explanatory extension module geometries will be shown herein for illustration, others will be readily apparent to those of ordinary skill in the art having the benefit of this disclosure as well. For instance, rather than employing arched cells or batteries, the non-planar geometry can incorporate a series of segmented cell structures that follow a non-planar extension contour.

Functional features can be included into the hinge configuration as well. For example, in one embodiment the hinge is pre-loaded with a biasing member, such as a spring or elastomer, so as to bias the electronic module extensions towards the closed position or vice versa. Where configured to bias the electronic module extensions towards the closed position, the electronic module extensions can be used as "clips" to selectively attach the electronic module to a shirt, backpack, purse, or other article. In another embodiment, the electronic module extensions can be configured to couple to a wearer's ear so that the corresponding electronic module can be used as a hands-free device. In other embodiments, retention devices—such as magnets—can be disposed in one or more of the housing, the first electronic module extension, or the second electronic module extension to retain the electronic module extensions in the open or closed positions. In yet another embodiment, detents can be included within the hinge to provide a motion cessation feature to allow the electronic module extension to be opened to any of a predetermined number of angularly displaced orientations relative to the housing.

From a combined mechanical and electrical perspective, in one embodiment an operational mode of the electronic module can be configured by positioning the electronic module extensions in one or more predefined angularly displaced orientations. As will be shown below, electronic modules configured in accordance with embodiments of the invention can operate in a variety of modes. Such modes include a desktop mode, a telephone mode, a wristwatch mode, a health monitoring mode, a clock mode, a calendar mode, a gaming mode, or a media player mode. This list is not exclusive, as others will be readily apparent to those of ordinary skill in the art having the benefit of this disclosure. A user can cause the electronic module to enter a particular mode, in one embodiment, by placing the electronic module extensions in a predetermined alignment. Illustrating by example, when the electronic module is configured to be worn on the wrist by pivoting the electronic module extensions to the open position, a control circuit disposed within the housing may cause the device to enter the health monitoring mode, a wrist watch mode, or a combination thereof. By contrast, when one electronic module extension is folded to the closed position, the control circuit may cause the electronic device to enter a music player mode. When both electronic module extensions are pivoted to the closed position, the control circuit may cause the electronic device to enter the desktop mode or calendar mode or clock mode, and so forth. These modes are explanatory only, and are not intended to be limiting.

Turning now to FIG. 1, illustrated therein is one explanatory example of an electronic device 100 suitable for use with presentation orientation methods and systems described herein. As noted above, the methods and systems for altering presentation orientation are well suited for most any portable electronic device, including mobile communication devices, portable computers, and the like. For illustration purposes and simplicity of discussion, the electronic device 100 used in many of the figures is configured as a wearable electronic device. For example, the electronic device 100 of FIG. 1 is configured as a wristwatch having an active strap 102 and a detachable electronic module 101. This electronic device 100 is useful for discussion purposes because wearable devices configured in accordance with embodiments described herein can perform additional functions that traditional electronic devices cannot. However, it will be clear to those of ordinary skill in the art having the benefit of this disclosure that the additional features are optional and can be used in some applications, while the presentation orientation manipulation techniques can be applied to simpler, non-wearable devices without employing all of the advanced features of the illustrative wearable device.

Figure 2:
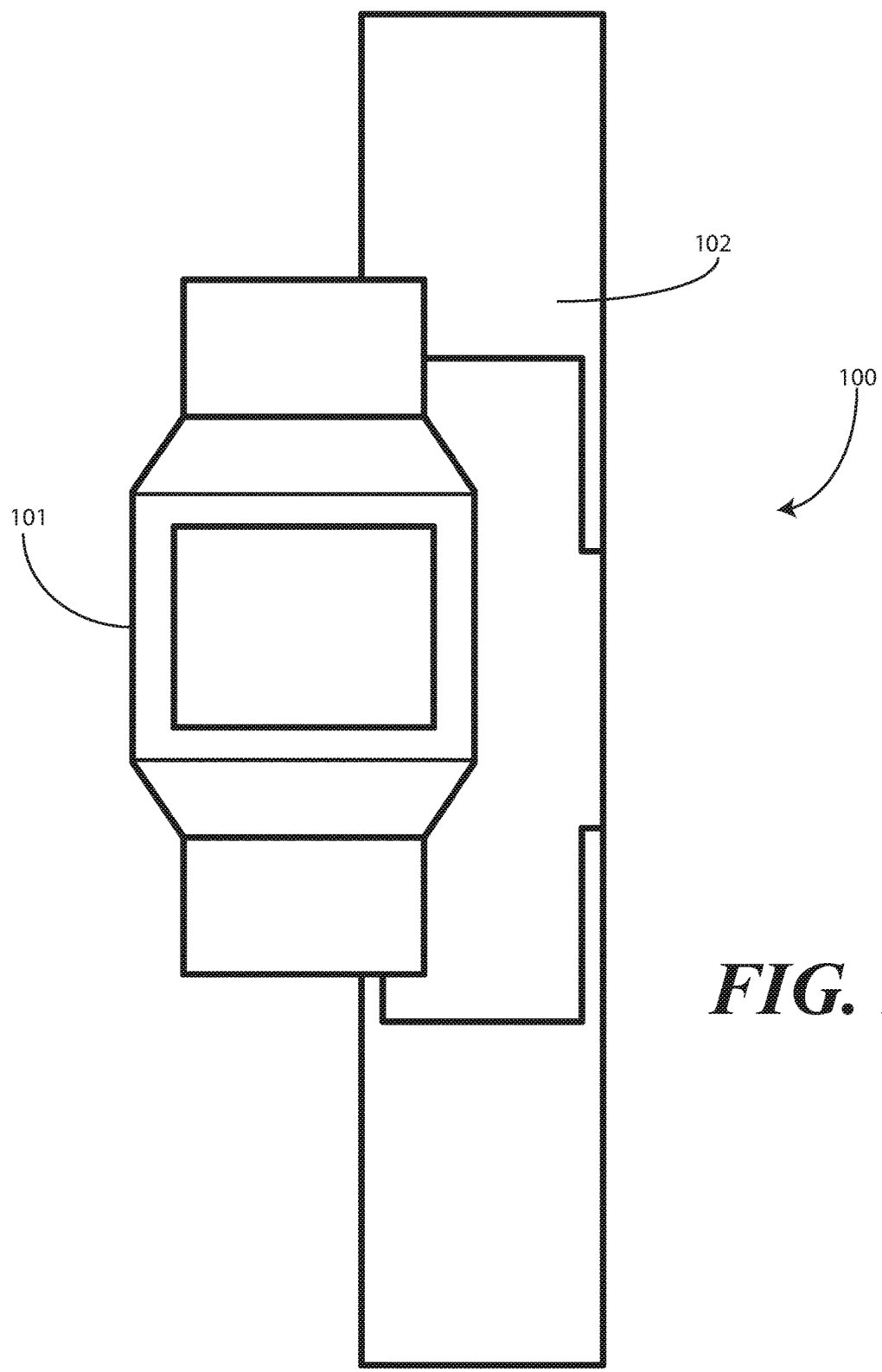
FIG. 2 illustrates an exploded view of one explanatory electronic device with separable components configured in accordance with one or more embodiments of the invention.

As shown in FIG. 2, the detachable electronic module 101 can be selectively detached from the active strap 102 so as to be used as a stand alone electronic device. For example, the detachable electronic module 101 can be configured with cellular communication capabilities and may be detached from the active strap 102 to be used more privately as a mobile telephone than if it were coupled to a wearer's wrist. In other embodiments, the active strap 102 can optionally be configured with mechanically configurable characteristics such that it can be used as a configurable stand when the electronic device 100 is placed on a table. Both the active strap 102 and the detachable electronic module 101 can be configured as "active" devices. An active device refers to a device that includes a power source and hardware. Active devices can include control circuits or processors as well.

In one or more embodiments, the detachable electronic module 101 can be detached from the active strap 102 so that it can be coupled with, or can communicate or interface with, other devices. For example, where the detachable electronic module 101 includes wide area network communication capabilities, such as cellular communication capabilities, the detachable electronic module 101 may be coupled to a folio or docking device to interface with a tablet-style computer. In this configuration, the detachable electronic module 101 can be configured to function as a modem or communication device for the tablet-style computer. In such an application, a user may leverage the large screen of the tablet-style computer with the computing functionality of the detachable electronic module 101, thereby creating device-to-device experiences for telephony, messaging, or other applications. The detachable nature of the detachable electronic module 101 serves to expand the number of experience horizons for the user.

Turning back to FIG. 1, in one embodiment the detachable electronic module 101 includes a display 103 configured to provide visual output having a presentation orientation 104 associated therewith. For illustration purposes, the presentation orientation 104 is shown as an arrow, which is pointing up. This constitutes a first presentation orientation. Where the arrow was pointing down, this would constitute a second presentation orientation, and so forth. The visual output can be text, pictures, video, audio, or other content.

As will be shown in subsequent figures, in one or more embodiments, the electronic device 100 can be configured with various combinations of the following features: wide area network communication capabilities, e.g., cellular or other mobile communication capabilities; local area network communication capabilities, e.g., Bluetooth™ or other similar communication capabilities; voice call capabilities including conventional phone functionality, speaker phone functionality, or private mode capabilities via a wired or wireless headset; one or more wellness sensors, such as heart rate sensors, temperature sensors, or sweat sensors; context sensors, such as accelerometers, global positioning sensors, microphones, local infrared sensors, local light sensors, and local touch sensors; and other safety and security sensors and applications. These features can be integrated into the detachable electronic module 101, the active strap 102, or by way of a combination of the two when coupling the detachable electronic module 101 to the active strap 102 is both an electrical and mechanical coupling.

The detachable electronic module 101, in one embodiment, is equipped with a first electronic module extension 107 and a second electronic module extension 108. The electronic module extensions 107, 108 can be coupled to the housing of the detachable electronic module 101 by way of hinge. Accordingly, the first electronic module extension 107 can be hingedly coupled to a first side of the housing such that it extends distally from the first side of the housing, while the second electronic module extension 108 can be hingedly coupled to a second side of the housing that different from the first side, such that it extends distally from the second side of the housing. The hinged attachment allows the first electronic module extension 107 and the second electronic module extension 108 to selectively pivot from a closed position, where the electronic module extensions 107, 108 are disposed against a rear, major face of the housing, to an angularly displaced open position extending distally outward from the housing.

The illustrative electronic device 100 of FIGS. 1 and 2 includes a form factor that is thin, pleasing, functional, and practical. Exemplary dimensions of some of the components will aid in understanding the shape and size of one explanatory embodiment. For instance, the display 103 can be configured with a 1.6-inch diagonal dimension. The detachable electronic module 101 can have a length 105 of about 62 millimeters, and a width of about 49 millimeters. (The term "about" is used to refer to dimensions inclusive of manufacturing and component tolerances. For example, a measurement of 48.1 or 49.9 millimeters will be about 49 millimeters when the manufacturing tolerances are plus or minus 1 millimeter.) In this illustrative embodiment, the electronic module extensions 107, 108 have a width 109 of about 42 millimeters, and a length 110 of between 20 and 40 millimeters, depending upon the application. An illustrative detachable electronic module 101 with communication capabilities, wellness detectors, and audio capabilities can be formed with a thickness (into the page) of about 10 millimeters. The length 111 of the active strap 102 can vary based upon target wearer's wrist size or application.

Figure 3:
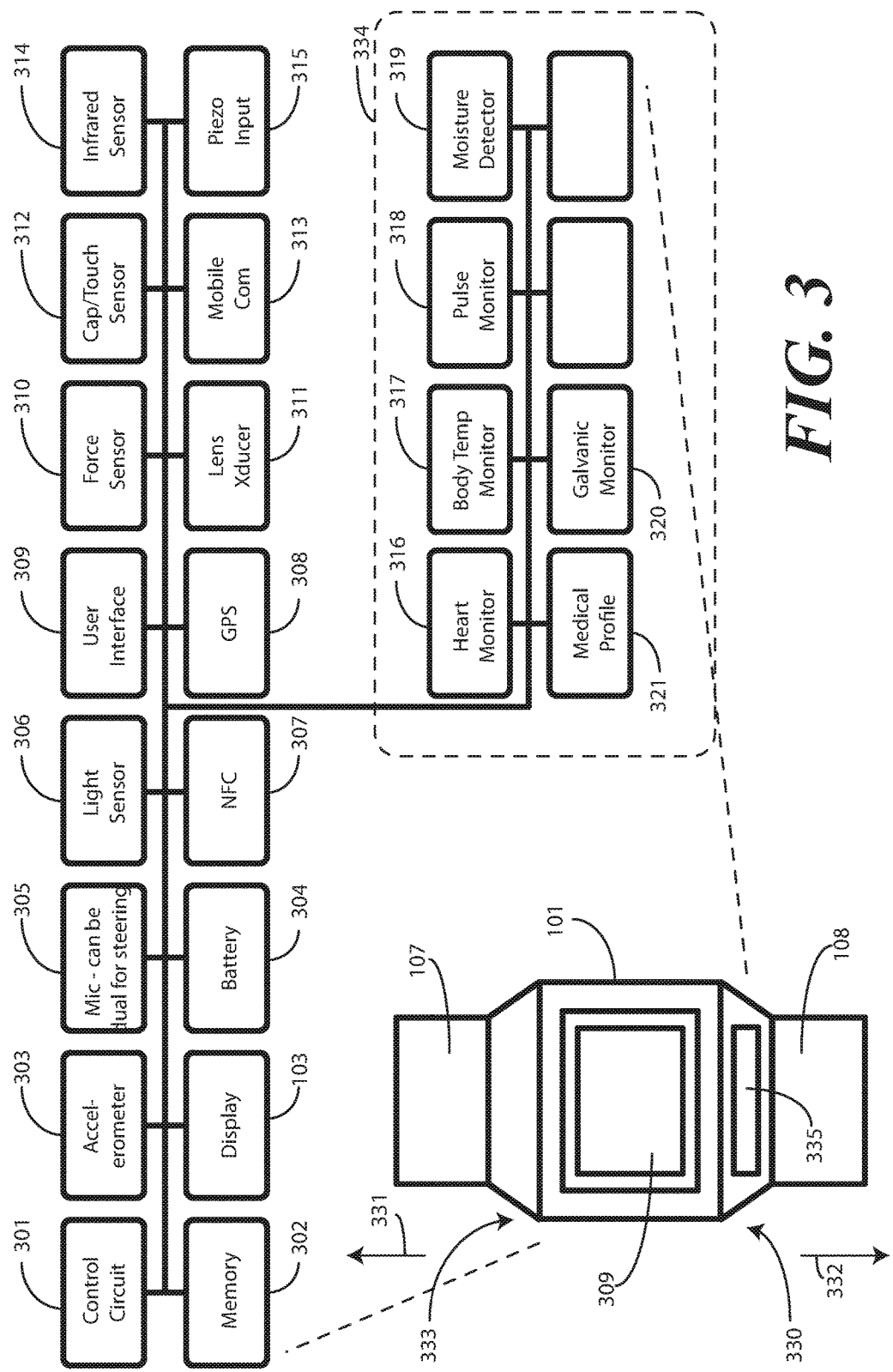
FIG. 3 illustrates a schematic block diagram of one explanatory electronic device configured in accordance with one or more embodiments of the invention.

Turning now to FIG. 3, illustrated therein is a schematic block diagram of various components and modules suitable for inclusion in the detachable electronic module 101. It will be clear to those of ordinary skill in the art having the benefit of this disclosure that the components and modules can be used in different combinations, with some components and modules included and others omitted. For altering the presentation orientation (104) of visual output presented on the display 103, the components of the display system can include a control circuit 301 and the display 103. The other components or modules can be included or excluded based upon need or application.

A control circuit 301 is coupled to the display 103. The control circuit 301 can be operable with a memory 302. The control circuit 301, which may be any of one or more microprocessors, programmable logic, application specific integrated circuit device, or other similar device, is capable of executing program instructions and methods described herein. The program instructions and methods may be stored either on-board in the control circuit 301, or in the memory 302, or in other computer readable media coupled to the control circuit 301. The control circuit 301 can be configured to operate the various functions of the detachable electronic module 101, and also to execute software or firmware applications and modules that can be stored in a computer readable medium, such as memory 302. The control circuit 301 executes this software or firmware, in part, to provide device functionality. The memory 302 may include either or both static and dynamic memory components, may be used for storing both embedded code and user data. One suitable example for control circuit 301 is the MSM7630 processor manufactured by Qualcomm, Inc. The control circuit 301 may operate one or more operating systems, such as the Android™ mobile operating system offered by Google, Inc. In one embodiment, the memory 302 comprises an 8-gigabyte embedded multi-media card (eMMC).

The control circuit 301, which in one embodiment is disposed in the central housing of the detachable electronic module 101 and not within either the first electronic module extension 107 or the second electronic module extension 108, can be configured to alter an operating mode of the electronic module to one of a plurality of functional modes. As noted above, these functional modes can include a desktop mode, a telephone mode, a wristwatch mode, a health monitoring mode, a clock mode, a calendar mode, a gaming mode, or a media player mode. As will be described below, the control circuit 301 in one embodiment selects an operational mode from these functional modes by detecting an angularly displaced orientation of the first electronic module extension 107, the second electronic module extension 108, or combinations thereof.

The display 103 is configured to provide visual output, images, or other visible indicia to a user. In one embodiment, the display 103 comprises a 1.6-inch organic light emitting diode (OLED) device. In one embodiment, the display 103 comprises a touch sensor 312 to form touch sensitive display configured to receive user input across the surface of the display 103. The display 103 can also be configured with a force sensor 310. Where configured with both a touch sensor 312 and force sensor 310, the control circuit 301 can determine not only where the user contacts the display 103, but also how much force the user employs in contacting the display 103. Where configured with a force sensor 310 but no touch sensitive capabilities, the display 103 can be used as a large "push button" or input control for the detachable electronic module 101. In one embodiment, explained in more detail below with reference to FIG. 15, the outer lens of the display 103 can be configured with piezoelectric sensors 315 or other actuators to be used as both an input device and an acoustic transducer.

The touch sensor 312 can include a capacitive touch sensor, an infrared touch sensor, or another touch-sensitive technology. Capacitive touch-sensitive devices include a plurality of capacitive sensors, e.g., electrodes, which are disposed along a substrate. Each capacitive sensor is configured, in conjunction with associated control circuitry, e.g., control circuit 301 or another display specific control circuit, to detect an object in close proximity with—or touching— the surface of the display 103 or the housing of the detachable electronic module 101 by establishing electric field lines between pairs of capacitive sensors and then detecting perturbations of those field lines. The electric field lines can be established in accordance with a periodic waveform, such as a square wave, sine wave, triangle wave, or other periodic waveform that is emitted by one sensor and detected by another. The capacitive sensors can be formed, for example, by disposing indium tin oxide patterned as electrodes on the substrate. Indium tin oxide is useful for such systems because it is transparent and conductive. Further, it is capable of being deposited in thin layers by way of a printing process. The capacitive sensors may also be deposited on the substrate by electron beam evaporation, physical vapor deposition, or other various sputter deposition techniques. For example, commonly assigned U.S. patent application Ser. No. 11/679,228, entitled "Adaptable User Interface and Mechanism for a Portable Electronic Device," filed Feb. 27, 2007, which is incorporated herein by reference, describes a touch sensitive display employing a capacitive sensor.

The force sensor 310 can take various forms. For example, in one embodiment, the force sensor 310 comprises resistive switches or a force switch array configured to detect contact with either the display 103 or the housing of the detachable electronic module 101. An "array" as used herein refers to a set of at least one switch. The array of resistive switches can function as a force-sensing layer, in that when contact is made with either the surface of the display 103 or the housing of the detachable electronic module 101, changes in impedance of any of the switches may be detected. The array of switches may be any of resistance sensing switches, membrane switches, force-sensing switches such as piezoelectric switches, or other equivalent types of technology. In another embodiment, the force sensor 310 can be capacitive. One example of a capacitive force sensor is described in commonly assigned, U.S. patent application Ser. No. 12/181,923, filed Jul. 29, 2008, published as US Published Patent Application No. US-2010-0024573-A1, which is incorporated herein by reference. In yet another embodiment, piezoelectric sensors 315 can be configured to sense force as well. For example, where coupled with the lens of the display 103, the piezoelectric sensors 315 can be configured to detect an amount of displacement of the lens to determine force. The piezoelectric sensors 315 can also be configured to determine force of contact against the housing of the detachable electronic module 101 rather than the display 103.

A mobile communication circuit 303 can be included to provide wide area communication capabilities. Where included, the mobile communication circuit 303 is operable with the control circuit 301, and is used to facilitate electronic communication with various networks, such as cellular networks, data networks, or the Internet. Note that it is possible to combine the control circuit 301, the memory 302, and the mobile communication circuit 303 into a single device or into devices having fewer parts while retaining the functionality of the constituent parts.

The mobile communication circuit 303, which may be one of a receiver or transmitter, and may alternatively be a transceiver, operates in conjunction with the control circuit 301 to electronically communicate through a communication network. For example, in one embodiment, the mobile communication circuit 303 can configured to communicate through a traditional cellular network, such as a Code Division Multiple Access (CDMA) network or Global System for Mobile communication (GSM) network. Other examples of networks with which the communication circuit may communicate include Push-to-Talk (PTT) networks, proprietary networks, dual band CDMA networks, or Dual Band Universal Mobile Telecommunications System (UMTS) networks, and direct communication networks. The mobile communication circuit 303 can be configured to provide messaging functionality to the detachable electronic module 101. In one or more embodiments, the detachable electronic module can communicate with one or more social networking applications through the mobile communication circuit 303 as well. News feeds and other data can be received through the mobile communication circuit 303. Moreover, context and location sensitive notifications can be sent and received via the mobile communication circuit 303.

A battery 304 or other energy source can be included to provide power for the various components of the detachable electronic module 101. While a battery 304 is shown in FIG. 3, it will be obvious to those of ordinary skill in the art having the benefit of this disclosure that other energy storage deices can be used instead of the battery 304, including a fuel container or an electrochemical capacitor. The battery 304 can include a lithium ion cell or a nickel metal hydride cell, such cells having reasonably large energy capacity, wide operating temperature range, large number of charging cycles, and long useful life. The battery 304 may also include overvoltage and overcurrent protection and charging circuitry. In one embodiment, the detachable electronic module 101 includes two batteries, with a battery being stored in each of the electronic module extensions 107, 108. In one embodiment, the battery 304 is configured as an 800 mAh lithium polymer cell.

In one or more embodiments, the battery 304 disposed within the first electronic module extension 107, the second electronic module extension 108, or combinations thereof, and not within the central housing of the detachable electronic module 101. In such a configuration, the battery 304 is configured to deliver energy to electronic components, e.g., the control circuit 301, memory 302, display 103, etc., each of which is disposed only within the central housing of the detachable electronic module 101.

One or more microphones 305 can be included to receive voice input, voice commands, and other audio input. A single microphone can be included. Optionally, two or more microphones can be included for selective beam steering. For example, a first microphone can be located on a first side 330 of the detachable electronic module 101 for receiving audio input from a first direction 332. Similarly, a second microphone can be placed on a second side 331 of the detachable electronic module 101 for receiving audio input from a second direction 333. As will be described below, an infrared sensor 314, light sensor 306, or other sensor can detect a direction in which a user is located. The control circuit 301 can then select between the first microphone and the second microphone to beam steer audio reception toward the user. Alternatively, the control circuit 301 processes and combines the signals from two or more microphones to perform beam steering. The one or more microphones 305 can be used for voice commands. When altering the presentation orientation of information presented on the display, the one or more microphones 305 can be configured to be responsive to the control circuit 301. Accordingly, the control circuit 301 can switch between microphones upon altering the presentation orientation in response to the user input.

A light sensor 306 is configured to detect changes in optical intensity, color, light, or shadow in the near vicinity of the detachable electronic module 101. For example, the light sensor 306 can be configured as an image sensing device that captures successive images about the device and compares luminous intensity, color, or other spatial variations between images to detect motion or the presence of an object near the detachable electronic module 101. Such sensors can be useful in determining at which side of the detachable electronic module 101 a user is standing. An infrared sensor 314 can be used in conjunction with, or in place of, the light sensor 306. The infrared sensor 314 can be configured to operate in a similar manner, but on the basis of infrared radiation rather than visible light. The light sensor 306 and/or infrared sensor 314 can be used for gesture commands, as will be described with reference to subsequent figures.

A near field communication circuit 307 can be included for communication with local area networks. Examples of suitable near field communication circuits include Bluetooth communication circuits, IEEE 801.11 communication circuits, infrared communication circuits, magnetic field modulation circuits, and Wi-Fi circuits.

A global positioning system device 308 can be included for determining where the detachable electronic module 101 is located. (Note that the global positioning system device 308 can also be used to determine the spatial orientation of the detachable electronic module 101 in three-dimensional space by determining the change in position of the device relative to the earth.) The global positioning system device 308 is configured for communicating with a constellation of earth orbiting satellites or a network of terrestrial base stations to determine an approximate location. Examples of satellite positioning systems suitable for use with embodiments of the present invention include, among others, the Navigation System with Time and Range (NAVSTAR) Global Positioning Systems (GPS) in the United States of America, the Global Orbiting Navigation System (GLONASS) in Russia, and other similar satellite positioning systems. The satellite positioning systems based location fixes of the global positioning system device 308 autonomously or with assistance from terrestrial base stations, for example with assistance from a cellular communication network or other ground based network, or as part of a Differential Global Positioning System (DGPS), as is well known by those having ordinary skill in the art. While a global positioning system device 308 is one example of a location determination module, it will be clear to those of ordinary skill in the art having the benefit of this disclosure that other location determination devices, such as electronic compasses or gyroscopes, could be used as well.

A user interface 309 can be included. As noted above, in one embodiment, the display 103 is configured as a touch sensitive display, and accordingly functions as a user interface in and of itself. However, some applications will be better served with additional user interface components as well. The user interface 309, where included, can be operable with the control circuit 301 to deliver information to, and receive information from, a user. The user interface 309 can include a keypad 335, navigation devices, joysticks, rocker switches, slider pads, buttons, or other controls, and optionally a voice or touch command interface. These various components can be integrated together.

In one or more embodiments, the lens of the display 103 can be configured as a lens transducer 311 to deliver audio output to a user. While this will be described in more detail with reference to FIG. 15 below, piezoelectric transducers can be operably disposed with a lens of the display 103. Actuation of the piezoelectric transducers can cause the lens of the display 103 to vibrate, thereby emitting acoustic output. An example of a piezo-driven lens speaker is described in commonly assigned, pending U.S. Ser. No. 12/967,208, filed Dec. 14, 2010, entitled "Portable Electronic Device," which is incorporated herein by reference.

An accelerometer 313 can be included to detect motion of the detachable electronic module 101. The accelerometer 313 can also be used to determine the spatial orientation of the detachable electronic module 101 in three-dimensional space by detecting a gravitational direction. In addition to, or instead of, the accelerometer 313, an electronic compass can be included to detect the spatial orientation of the detachable electronic module 101 relative to the earth's magnetic field. Similarly, one or more gyroscopes can be included to detect rotational motion of the detachable electronic module 101. The gyroscope can be used to determine the spatial rotation of the detachable electronic module 101 in three-dimensional space.

Where the detachable electronic module 101 is configured as a wellness device, or is capable of operating in a health monitoring mode or physical safety device, one or more wellness sensors 334 can be included as well. Examples of wellness sensors are described in commonly assigned U.S. patent application Ser. No. 10/396,621, filed Mar. 24, 2003, published as US Published Patent Application No. 2004/0015058, which is incorporated herein by reference.

For example, a heart monitor 316 can be configured to employ EKG or other sensors to monitor a user's heart rate. The heart monitor 316 can include electrodes configured to determine action potentials from the skin of a user. A temperature monitor 317 can be configured to monitor the temperature of a user. A pulse monitor 318 can be configured to monitor the user's pulse. The pulse monitor 318 lends itself to the wristwatch configuration of the electronic device (100) of FIG. 1 because the wrist serves as an advantageous location from which to measure a person's pulse.

A moisture detector 319 can be configured to detect the amount of moisture present on a person's skin. The moisture detector 319 can be realized in the form of an impedance sensor that measures impedance between electrodes. As moisture can be due to external conditions, e.g., rain, or user conditions, perspiration, the moisture detector 319 can function in tandem with ISFETS configured to measure pH or amounts of NaOH in the moisture or a galvanic sensor 320 to determine not only the amount of moisture, but whether the moisture is due to external factors, perspiration, or combinations thereof.

The medical history of a user, as well as the determinations made by the various wellness sensors 334, can be stored in a medical profile 321. Periodic updates can be made to the medical profile 321 as well. The medical profile 321 can be a module operable with the control circuit 301. Such modules can be configured as sets of instructions stored in the memory 302 that are usable by the control circuit 301 to execute the various wellness monitoring functions of the detachable electronic module 101. Alternatively, the modules could be configured in hardware, such as through programmable logic. The wellness sensors 334 shown in FIG. 3 are illustrative only. Embodiments of the present invention may use various combinations of wellness sensors 334, including subsets of the wellness sensors 334 shown in FIG. 3. Further, other modules may be added to further increase device functionality. The wellness sensors 334 can be used to provide the user with a sensor-based health and wellness data assessment. The wellness sensors 334 can be used in conjunction with the medical profile 321 to provide context sensitive recommendations on the display 103.

Figure 4:
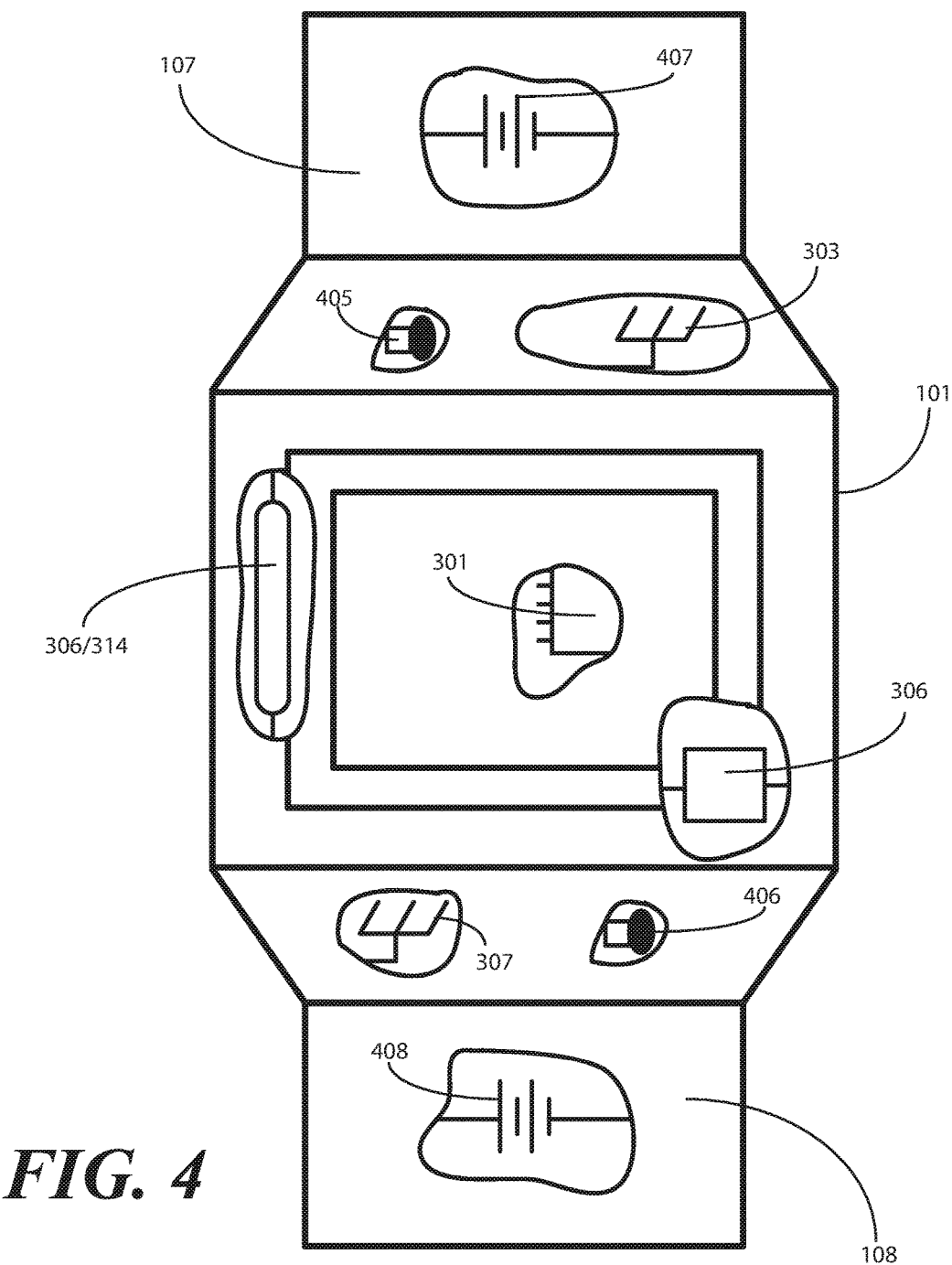
FIG. 4 illustrates a cut-away view of one explanatory electronic device configured in accordance with one or more embodiments of the invention.

Turning now to FIG. 4, illustrated therein is a cut-away view of the detachable electronic module 101 illustrating how some of the components of FIG. 3 may be disposed within the housing of the detachable electronic module 101.

The battery (304) in the embodiment of FIG. 4 comprises a first cell 407 disposed in a first electronic module extension 107 and a second cell 408 disposed in a second electronic module extension 108. All other electrical components, such as the control circuit 301, are disposed within a central housing of the detachable electronic module 101, with the exception of any conductors or connectors, safety circuits, or charging circuits used or required to deliver energy from the first cell 407 and second cell 408 to the electronic components disposed within the central housing. In this illustrative embodiment, the first cell 407 and second cell 408 each comprise 400 mAh lithium cells. Where the detachable electronic module 101 is configured for communication with both wide area networks, e.g., cellular networks, and local area networks, e.g., WiFi networks, both the first cell 407 and the second cell 408 can be included. However, in some embodiments where only local area network communication or no communication capability is included, one of the first cell 407 or second cell 408 may be omitted. As noted above, the first cell 407 and second cell 408 can be coupled in parallel to provide higher peak pulse currents. Alternatively, the first cell 407 and the second cell 408 can be coupled in series when there is no high current demand. One or more switches can be used to selectively alter the coupling of the first cell 407 and second cell 408 in the series/parallel configurations.

The mobile communication circuit 303 is disposed at a first end of the detachable electronic module 101. The near field communication circuit 307 can be disposed on a side of the detachable electronic module 101 opposite the mobile communication circuit 303. The global positioning system device (308), where included, can also be disposed on a side opposite the mobile communication circuit 303. In this illustrative embodiment, the global positioning system device (308) is displaced from the near field communication circuit 307 to avoid interference. The light sensor 306 and/or infrared sensor 314 can be disposed on a side of the device.

The microphones (305) in this embodiment comprise a first microphone 405 disposed on a first side of the detachable electronic module 101 and a second microphone 406 disposed on a second side of the detachable electronic module 101 that is opposite the first side. As noted above, multiple microphones can be included to receive voice input, voice commands, and other audio input. In this embodiment, the first microphone 405 and second microphone 406 can be used for selective beam steering. The infrared sensor 314, light sensor 306, or other sensor can detect a directional position of a user. The control circuit 301 can then select between the first microphone 405 and the second microphone 406 to beam steer audio reception toward the user.

Figure 5:
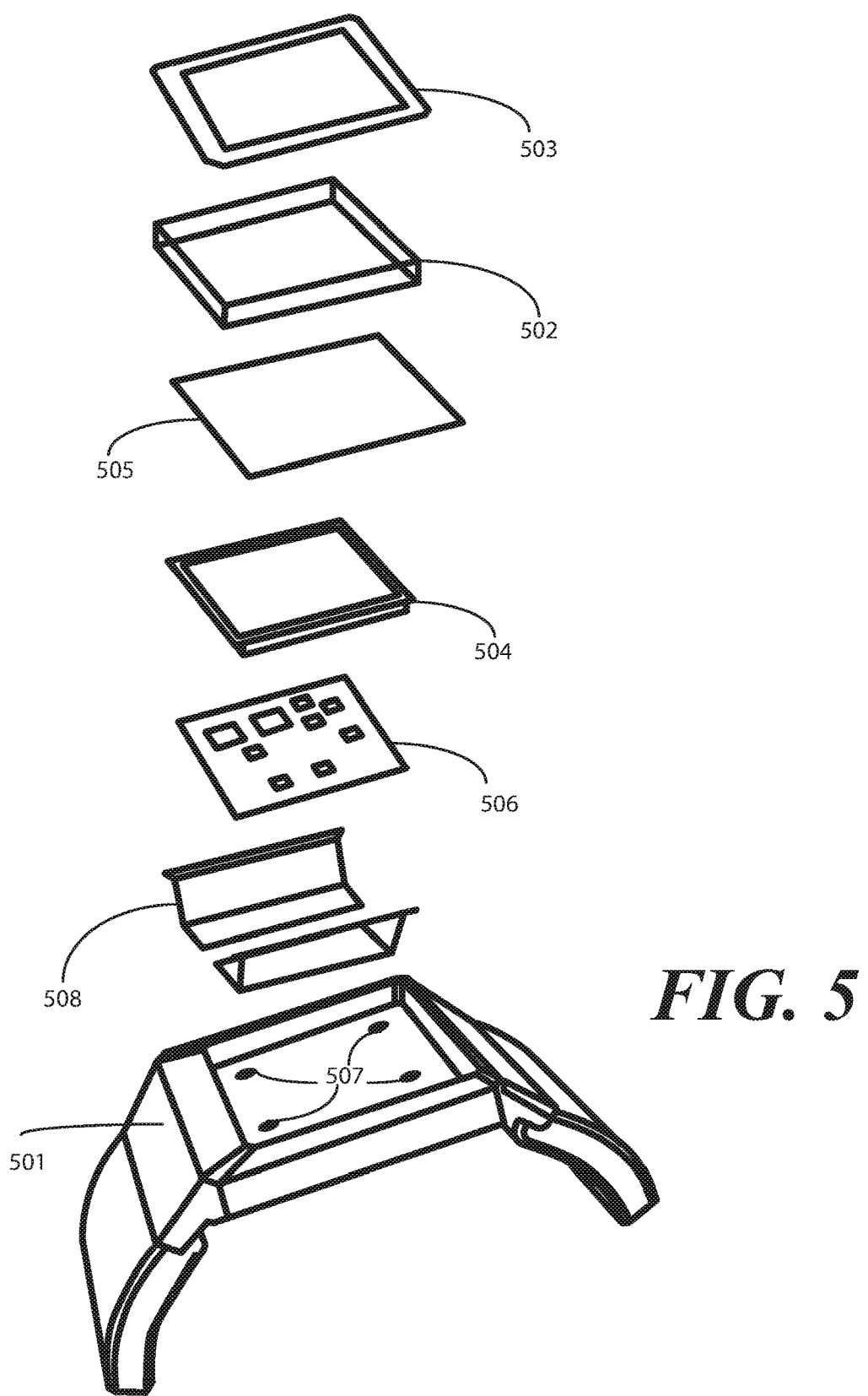
FIG. 5 illustrates an exploded view of some internal components associated with one explanatory electronic device configured in accordance with one or more embodiments of the invention.
Figure 6:
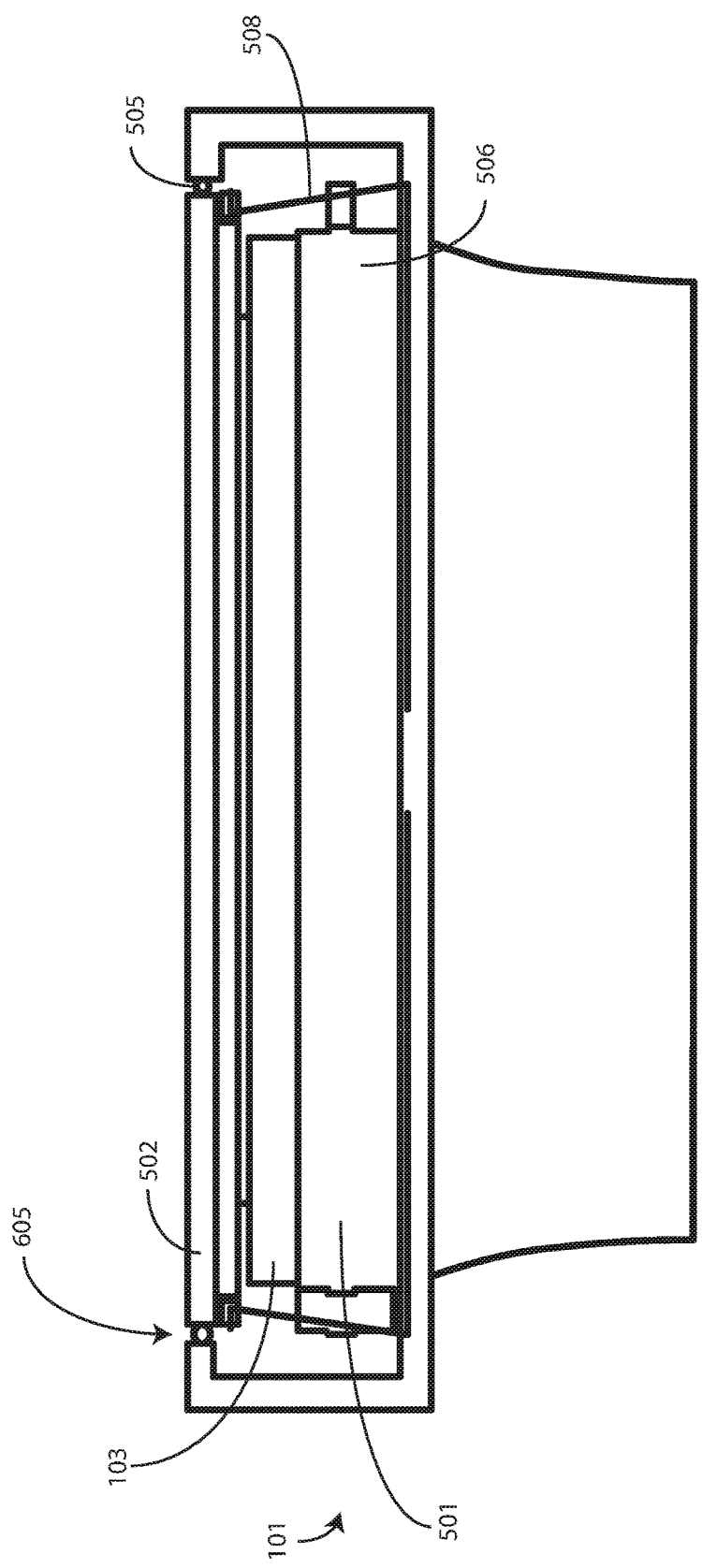
FIG. 6 illustrates a sectional view of one explanatory electronic device configured in accordance with one or more embodiments of the invention.

Turning now to FIGS. 5 and 6, illustrated therein are additional internal components associated with one explanatory detachable electronic module 101 configured in accordance with one or more embodiments of the invention. FIG. 5 illustrates an exploded view, while FIG. 6 illustrates a sectional view.

The detachable electronic module 101 includes a housing 501 configured to carry internal components. This illustrative housing 501 is curved and contoured so as to forma a wearable housing, in that it can be coupled to either a passive or active strap and worn about a wrist, arm, or leg. Alternatively, it could be coupled about a waist as well. In one embodiment, the housing 501 and a cover layer 502 of the display assembly bound the internal components. An optional mechanical upper housing 503 can also be used to retain the cover layer 502 within the housing 501. (The optional mechanical upper housing 503 is not shown in FIG. 6.)

The cover layer 502 can be a substrate manufactured from thin plastic film, sheet plastic, or reinforced glass. The cover layer 502 serves as a fascia member for the detachable electronic module 101. A "fascia" is a covering or housing, which may or may not be detachable, for an electronic device like the detachable electronic module 101 of FIGS. 5 and 6. To provide ornamentation, text, graphics, and other visual indicators, the cover layer 502, in one embodiment, includes printing disposed on the rear face. Selective printing on the cover layer 502 may be desirable, for instance, around the perimeter of the cover layer 502 to cover electrical traces connecting internal components. Printing may be desired on the front face of the cover layer 502 for various reasons as well. For example, a subtle textural printing or overlay printing may be desirable to provide a translucent matte finish atop the detachable electronic module 101. Such a finish is useful to prevent cosmetic blemishing from sharp objects or fingerprints. By printing only on the rear face, the front face can remain smooth and glossy. The cover layer 502 may also include an ultra-violet barrier as well. Such a barrier is useful both in improving the visibility of the display module 504 and in protecting internal components of the detachable electronic module 101. As noted above, the cover layer 502 can include a plurality of indium tin oxide or other electrodes, which function as a capacitive sensor, to covert the display to a touch-sensitive display.

Beneath the cover layer 502 is the display module 504, which in this case is an OLED display module. The display module 504 is configured to provide visual output having a presentation orientation through the cover layer 502 to the user.

As noted above, in one or more embodiments, the display (103) or cover layer 502 can be can be used as a user input and as a transducer for acoustic output. In some embodiments, the cover layer 502, display module 504, or combinations thereof will be moveable relative to the housing 501. In some embodiments, an acoustic roll of compliant material 505 can be disposed between the cover layer 502 and the housing 501. The inclusion of the acoustic roll facilitates small movement of the cover layer 502, display module 504, or combinations thereof relative to the housing 501. A design gap 605 can be included between the cover layer 502 and the housing 501 for insertion of the acoustic roll of compliant material 505 and to facilitate travel of the cover layer 502 relative to the housing 501. In embodiments that have an exposed display (103) with no cover layer 502, the display (103) can be attached to the acoustic roll of compliant material 505 in place of the cover layer 502. In these embodiments, the movable display module would serve the as the user input and transducer for acoustic output.

A circuit carrier 506 can then include the control circuit (301) and other electronic circuitry components and modules. In one embodiment, the circuit carrier 506 comprises a printed circuit board manufactured from FR-4 fiberglass. In another embodiment, the circuit carrier 506 comprises a flexible substrate disposed about flexible conductors, which is known in the art as a "flex" circuit. The circuit carrier 506 can include components disposed on the top and bottom sides. Alternatively, the circuit carrier 506 can have components disposed on a single side to conserve cost. The circuit carrier 506 can comprise one or more substrates that are coupled together with electrical conductors, wires, or other flex circuits.

Where the cover layer 502 is used in conjunction with piezoelectric devices 507, a piezo frame 508 can be used as a mechanical support extending from the piezoelectric devices 507 and the cover layer 502. When the piezoelectric devices 507 are actuated, the piezo frame 508 transfers force to the cover layer 502 to make it move in response to the forces generated by the piezoelectric devices 507. Alternatively, when a user engages the cover layer 502 to use it as a control input, user exerted force is transferred through the piezo frame 508 to the piezoelectric devices 507, which function as an input sensor in this mode.

The piezoelectric devices 507 can be configured as disks or pills as shown in FIG. 5. Alternatively, the piezoelectric devices 507 can be configured as bendable elements bonded to the piezo frame 508. In the case where piezoelectric disks are couple to the piezo frame 508, one portion of the piezoelectric disks can be coupled to the piezo frame 508 while another portion of the piezoelectric disks is coupled to the housing 501 or another portion of detachable electronic module 101 that is more massive than the cover layer 502. Alternatively the piezoelectric disks can be disposed between the cover layer 502 and the piezo frame 508, reversing the order of the components, but still providing the same effective functionality. This latter embodiment serves as an effective mechanical grounding for the piezoelectric system. In an embodiment where the piezoelectric devices 507 are bendable elements bonded to the piezo frame 508, the bendable elements can be bonded only to the piezo frame 508, with the frame being coupled to both the cover layer 502 and the housing 501.

Figure 7:
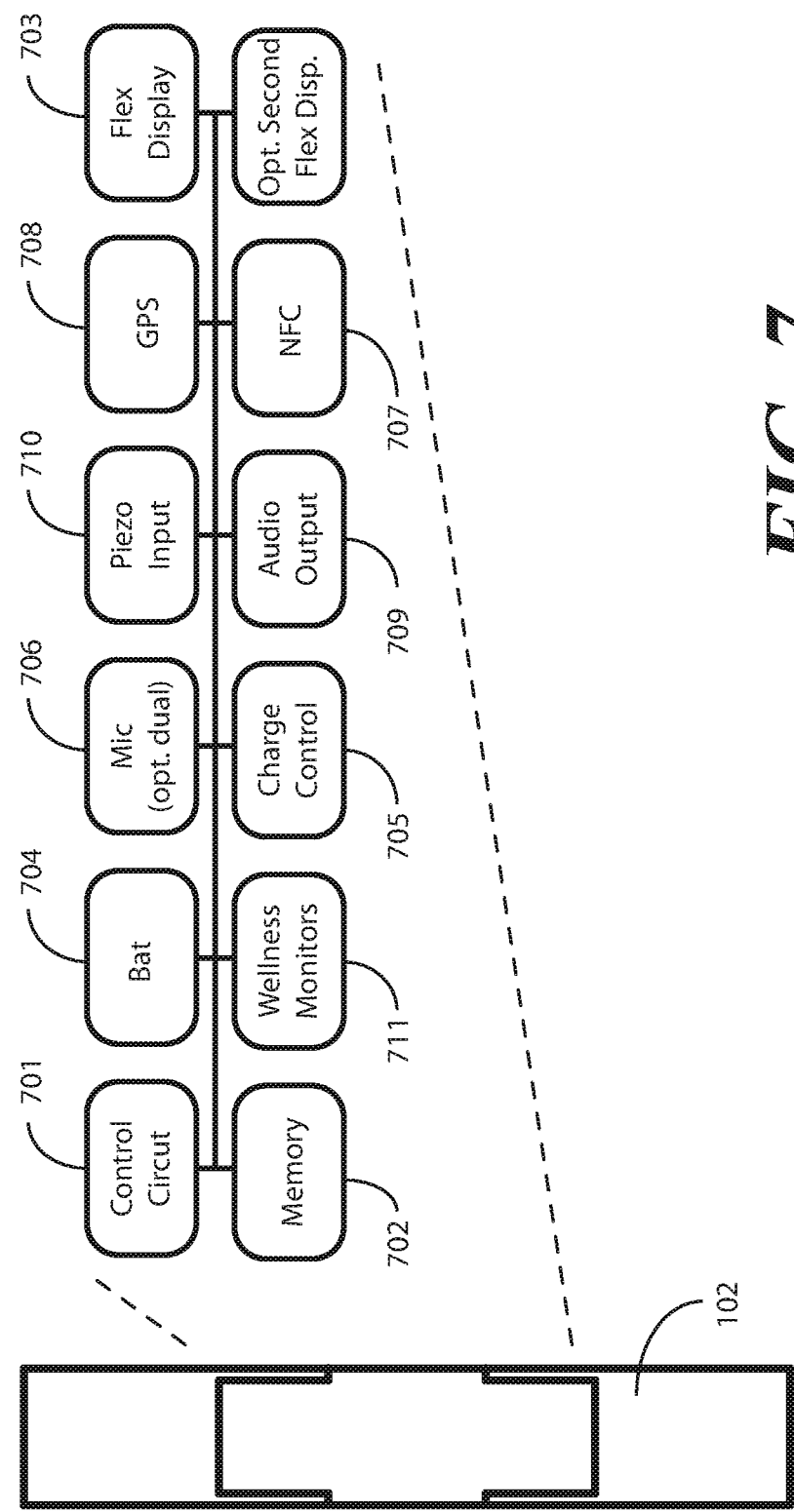
FIG. 7 illustrates a schematic block diagram of one explanatory wearable component suitable for use with an electronic device configured in accordance with one or more embodiments of the invention.

Turning to FIG. 7 illustrated therein are components that can be included in the active strap 102. Note that in many embodiments, the detachable electronic module (101) can be coupled to passive straps or attachments to form a wearable electronic device. In one or more embodiments, functionality can be increased by providing an active strap 102 that also includes a power source and hardware components. The components shown in FIG. 7 provide an illustration of components that can be included with the active strap 102. However, as with the modules shown in FIG. 3, the active strap 102 can include subsets of the modules, with only those modules being included as required by a particular application.

The active strap 102 can include its own control circuit 701. The control circuit 701 can be operable with a memory 702. The control circuit 701, which may be any of one or more microprocessors, programmable logic, application specific integrated circuit device, or other similar device, is capable of executing program instructions associated with the functions of the active strap 102. The program instructions and methods may be stored either on-board in the control circuit 701, or in the memory 702, or in other computer readable media coupled to the control circuit 701.

The active strap 102 can include a display 703. In one embodiment, the display 703 comprises one or more flexible display devices. Since the active strap 102 can be configured as a wristband for a wristwatch-type wearable device, flexible displays disposed on the active strap 102 can "wrap" around the wearer's wrist without compromising operational performance. While the display 703 can include non-flexible displays as well, the inclusion of flexible display devices not only increases comfort for the wearer but also allows the display 703 to be larger as well. The display 703 can be configured to be touch sensitive also, thereby allowing the display 703 to be used as a control input. The display is configured to provide visual output, images, or other visible indicia to a user. The display 703 can also be configured with a force sensor. Where configured with both, the control circuit 701 can determine not only where the user contacts the display 703, but also how much force the user employs in contacting the display 703. Where configured with a force sensor only, the display 703 can be used as a large "push button" or input control.

A battery 704 or other energy source can be included to provide power for the various components of the active strap 102. In one or more embodiments, the battery 704 is selectively detachable from the active strap 102. Charging circuitry 705 can be included in the active strap 102 as well. The charging circuitry 705 can include overvoltage and overcurrent protection. In one embodiment, the battery 704 is configured as a flexible lithium polymer cell.

One or more microphones 706 can be included to receive voice input, voice commands, and other audio input. A single microphone can be included. Optionally, two or more microphones can be included for selective beam steering. As with the detachable electronic module (101) described above, a first microphone can be located on a first side of the active strap 102 for receiving audio input from a first direction, while a second microphone can be placed on a second side of the active strap 102 for receiving audio input from a second direction. In response to a sensor, perhaps located in the detachable electronic module (101), a user location direction can be determined. The control circuit 701 can then select between the first microphone and the second microphone to beam steer audio reception toward the user. Alternatively, the control circuit 701 can employ a weighted combination of the microphones to beam steer audio reception toward the user.

A near field communication circuit 707 can be included for communication with local area networks. A global positioning system device 708 can be included for determining location information. One or more audio output devices 709 can be included to deliver audio output to a user. Piezoelectric devices 710 can be configured to both receive input from the user and deliver haptic feedback to the user.

Where desired, one or more wellness sensors 711 can be included as well. As described above, the wellness sensors 711 can include a heart monitor, moisture detector, temperature monitor, pulse monitor, galvanic devices, and so forth.

Figure 8:
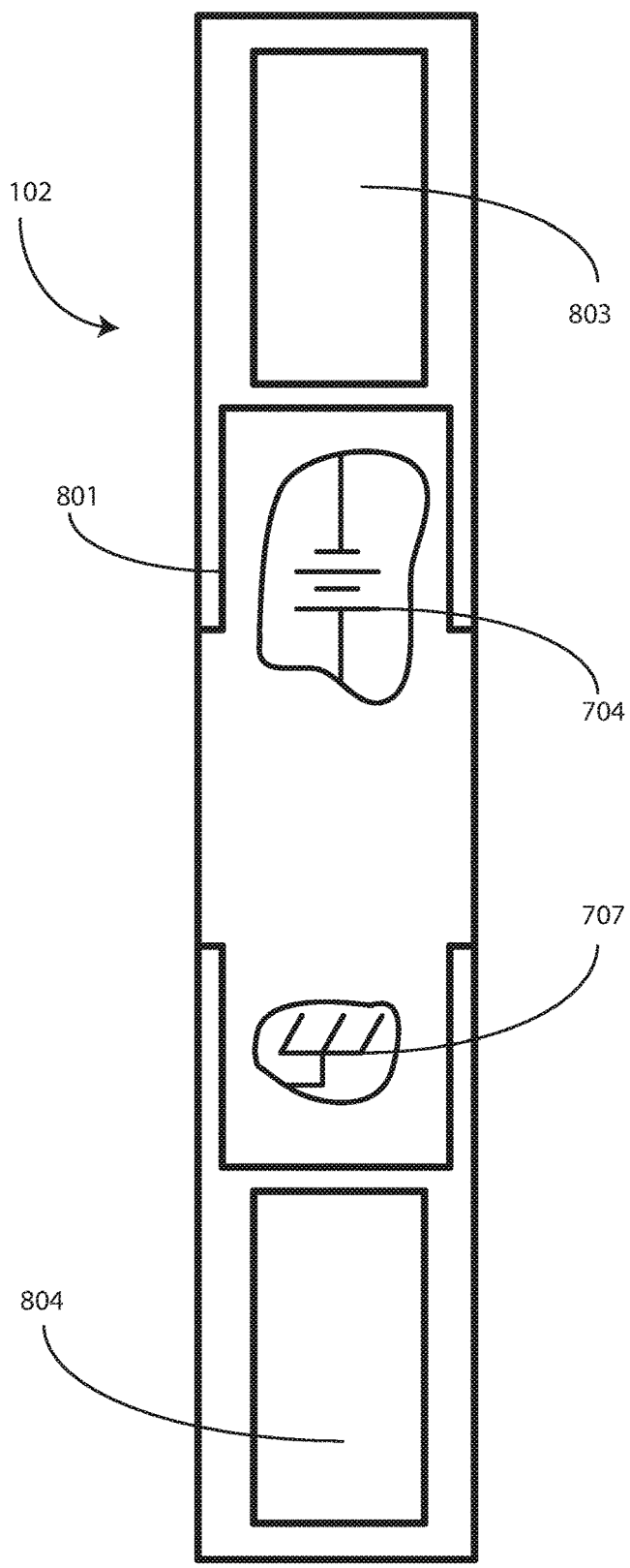
FIG. 8 illustrates a cut-away view of one explanatory wearable component suitable for use with an electronic device configured in accordance with one or more embodiments of the invention.

Turning now to FIG. 8, illustrated therein is a cut-away view of the active strap 102 that demonstrates illustrative locations of some of the components shown in FIG. 7. In this illustrative embodiment, the display (703) comprises a first display 803 disposed on a first side of the active strap 102 and a second display 804 disposed on a second side of the active strap 102. The first display 803 and the second display 804 are flexible displays, and cover substantial portions of the outer surface of the upper face of the active strap 102. Disposition of the displays in this arrangement lends itself to interesting applications. For example, when used with a light sensor (306) of a detachable electronic module (101) coupled to the active strap, the displays can present a color that is complementary to the colors worn by the user, thereby transforming the active strap 102 into a fashion accessory. Alternatively, the displays can present data, images, video, or other indicia to the user.

The battery 704 in this illustrative embodiment has been disposed beneath an attachment bay 801. The attachment bay 801 is configured for attachment to other electronic devices, one example being the detachable electronic module (101) of FIG. 4. Where included, the near field communication circuit 707 can be disposed within the attachment bay 801 as well. Alternatively, the near field communication circuit 707 can be disposed in the outer portions of the active strap 102.

Figure 9:
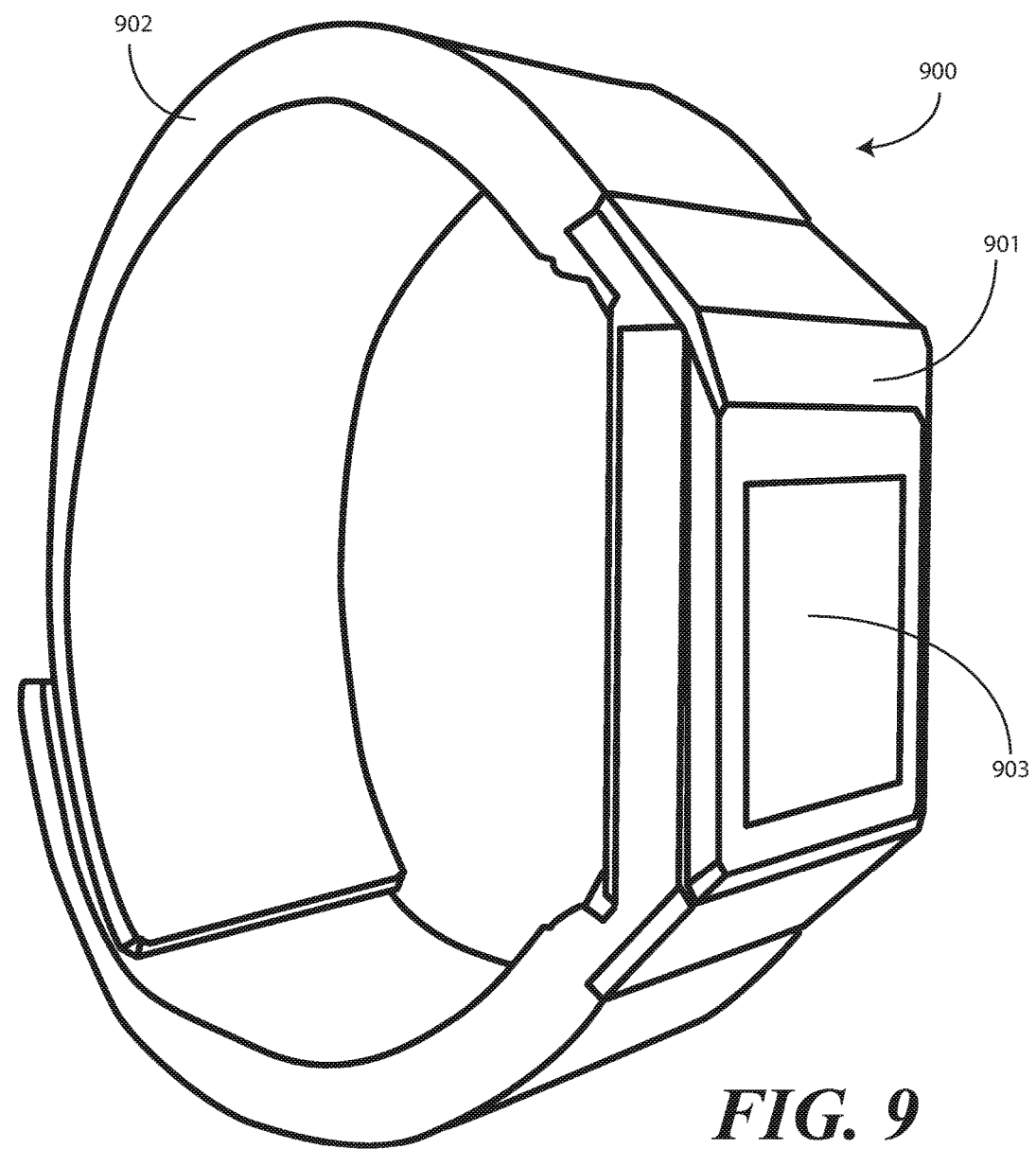
FIGS. 9-12 illustrate various stages of coupling between an explanatory wearable component and an explanatory electronic device configured in accordance with one or more embodiments of the invention.

Turning now to FIG. 9, illustrated therein is another embodiment of an electronic device 900 configured in accordance with embodiments of the present invention. The electronic device 900 is configured as a wearable device. A detachable electronic module 901 is coupled to an active strap 902 to form a wrist wearable device. The illustrative electronic device 900 of FIG. 9 includes a mobile communication circuit (303), a touch sensitive display 903, wellness sensors (334), a near field communication circuit (307), a global positioning system device (308), an infrared sensor (314), twin microphones configured for selective beam steering, and a cover layer configured with piezoelectric sensors (315) so as to function as an acoustic transducer and input control device. Accordingly, the electronic device 900 can function in a telephone mode to not only serve as a personal communication device akin to a mobile telephone, but can also function in a health monitoring mode to also serve as a personal safety and security device capable of detecting falls, user accidents, user drowsiness, user sleep and sleep patterns. Moreover, the electronic device 900 is capable of sending and receiving emergency alert communication messages, as well as delivering alert notifications to the user. In one or more embodiments, the electronic device 900 can be configured to communicate with social networks to provide automatic wellness and other updates to friends or family. The wearable electronic device 900 functions as a wearable wireless communication device that is compact and includes wellness sensing capabilities. The electronic device 900 has an efficient, compact design with a simple user interface configured for efficient operation with one hand (which is advantageous when the electronic device 900 is worn on the wrist).

In addition to the touch sensitive input of the touch sensitive display 903, the electronic device 900 is further equipped with an accelerometer (313) that can detect movement. Accordingly, when the electronic device 900 is worn on a wrist, the user can make gesture commands by moving the arm in predefined motions. Additionally, the user can deliver voice commands to the electronic device 900 via the twin microphones.

The user interface of the electronic device 900 is specially designed for a small screen. It included an intuitive touch interface. When the piezoelectric sensors (315) in conjunction with the cover layer of the touch sensitive display 903 are utilized as a touch interface, special functions can be realized. For example, the cover layer can be pressed for a short time, e.g., less than two seconds, to power on and off the electronic device 900. Alternatively, the cover layer can be pressed for a long time, e.g., more than two seconds, to perform a special function, such as transmission of an emergency message.

When the touch sensitive display 903 is configured as a touch sensitive display, control input can be entered in some embodiments with a single swiping action across the surface of the touch sensitive display 903. When operating in conjunction with the piezoelectric sensors (315), the touch sensitive display 903 can deliver intelligent alerts, acoustics, and haptic feed back in addition to visual output. In one or more embodiments, the touch sensitive display 903 is configured to alter magnification of the visual output for special applications. For instance, the touch sensitive display 903 can alter the magnification of a keypad during mobile communication dialing operations.

Using the near field communication circuit (307), the electronic device 900 can communicate with other electronic devices to provide "device to device" connectivity. For example, the electronic device 900 can link to a tablet-style computer to permit viewing of the visual output of the touch sensitive display 903 on a larger screen. The electronic device 900 can further serve as a communication portal for the tablet style computer, providing telephony functionality, messaging functionality, and notification functionality for the tablet-style computer.

As the electronic device 900 is configured with a small form factor in a wearable configuration, it provides advantages over prior art devices. For example, with prior art devices, a user employing a tablet-style computer frequently had to carry a mobile telephone to provide communication capability for the tablet-style computer. The wearable nature of the electronic device 900 alleviates the need to carry a large communication device for device-to-device connectivity with portable computers or tablet style computers. Moreover, the wearable nature of the electronic device 900 is compact and simple for a user to carry.

The inclusion of wellness sensors (334) provides advantageous applications in the area of wellness and health. For example, the medical profile (321) permits a user to store a medical history or wellness profile in the electronic device 900. Applications operable on the electronic device 900 can then draw on this information to provide wellness applications that are specifically tailored to the wearer. Additionally, sensors like the heart monitor (316), pulse monitor (318), and temperature monitor (317) can continually monitor vital signals of the user while the electronic device 900 is worn. By maintaining a record of this monitoring in the medical profile (321), the electronic device can provide a wellness assessment by analyzing the data. Sleep can be detected based upon pulse and temperature. Additionally, high-risk situations can be detected from elevated pulse, heartbeat, and excessive perspiration.

Applications operable on the electronic device 900 can provide timely wellness and health reminders, such as when a user should ingest medicine or when the user should exercise. Further, wellness outcomes, such as the results of an exercise session, can be presented on the touch sensitive display 903. The wellness sensors (334) can be configured to monitor vital signals only upon predetermined criteria. For example, when the moisture detector (319) detects moisture, the wellness sensors (334) may presume the user is exercising and actuate vital sign monitoring. The wellness sensors (334) can be configured to make wellness recommendations based upon location, history, and/or activity. The wellness sensors (334) can be configured to provide early warnings that anticipate health events based upon data detected using onboard sensors. The wellness sensors (334) can be configured to automatically journal daily physical and wellness activity. The wellness sensors (334) can be configured to provide real time updates to trusted family members, friends, or medical service providers.

The wellness sensors (334) can be configured to automatically deliver messages to third parties, e.g., doctors, family members, or friends, when abnormal wellness conditions are detected. As noted above, in one or more embodiments, a user can send such a message by pressing the cover layer of the touch sensitive display 903 for a predetermined time. The wellness sensors (334) can be configured to detect falls, auto accidents, extended lack of motion of a wearer, or sleep. This will be described in more detail with reference to FIG. 24 below. In one embodiment, the wellness sensors (334) can be configured to provide awakening alerts to the user when drowsiness or sleep is detected.

Figure 10:
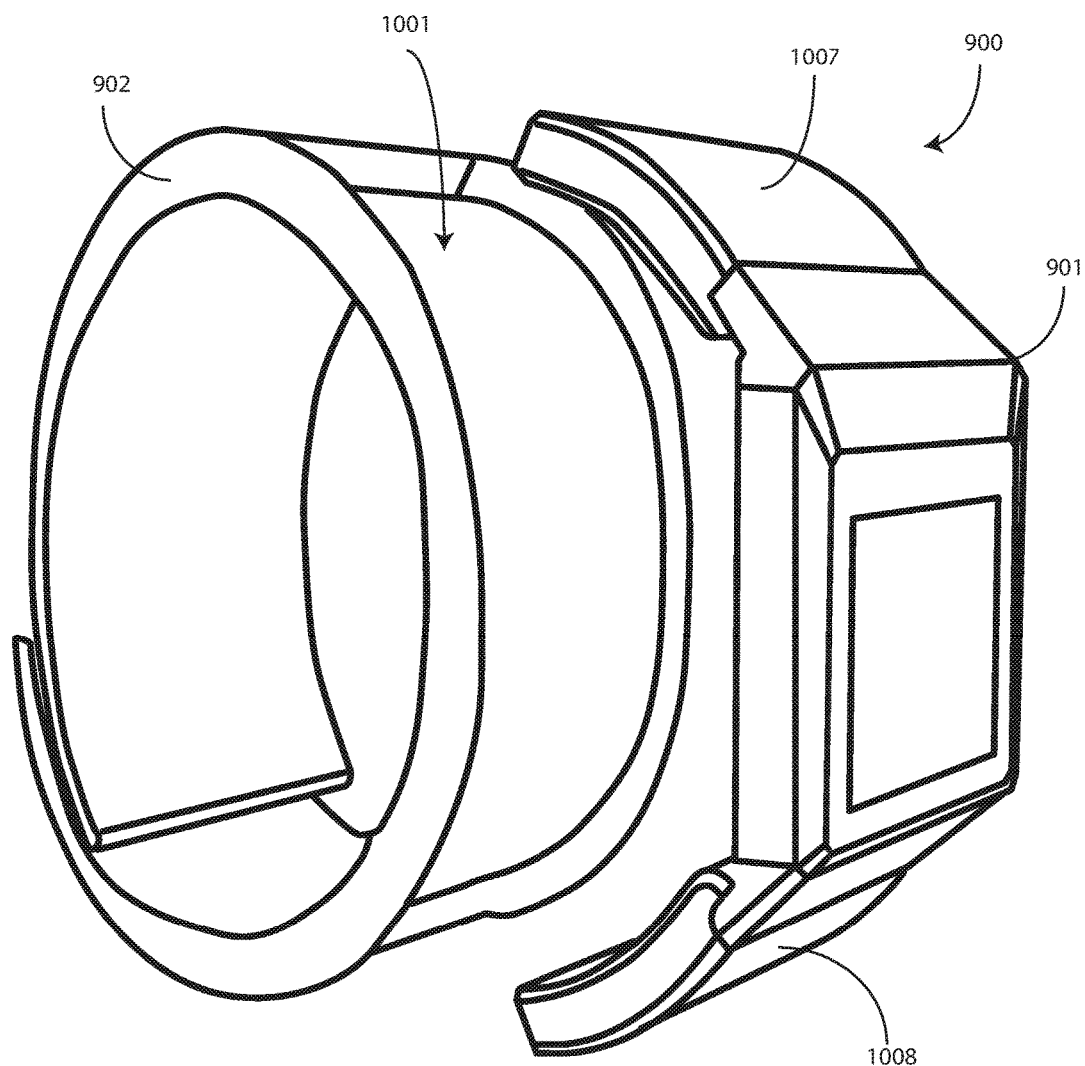

Turning now to FIG. 10, the detachable nature of the detachable electronic module 901 from the active strap 902 is shown. As will be described below with reference to FIG. 42, in one embodiment the detachable electronic module 901 can be detached from the active strap 902 by "hyper pivoting" the electronic module extensions 1007, 1008 relative to the housing of the detachable electronic module 901 away from the active strap 902.

In this illustrative embodiment, the electronic module extensions 1007, 1008 are non-planar, in that they are curved in cross section. This geometric configuration provides a wearable configuration for the detachable electronic module 901 in that the non-planar geometries of the electronic module extensions 1007, 1008 are complementary to the shape of a wearer's arm. Where this is the case, energy storage devices disposed within the electronic module extensions 1007, 1008 can be non-planar as well.

In FIG. 10, the detachable electronic module 901 has been released from the attachment bay 1001, thus converting it to a stand-alone device that can be used individually by the user or docked for use with other devices. In addition to providing wearable capabilities for the overall electronic device 900, the active strap 902 can be used for a stand. Since it is an active device with hardware and a power source, the active strap 902 can remain on the wrist to monitor wellness or other conditions while the detachable electronic module 901 is not connected. Upon reconnection, the detachable electronic module 901 can retrieve such monitored data and process it or communicate it as directed by a particular application.

Figure 11:
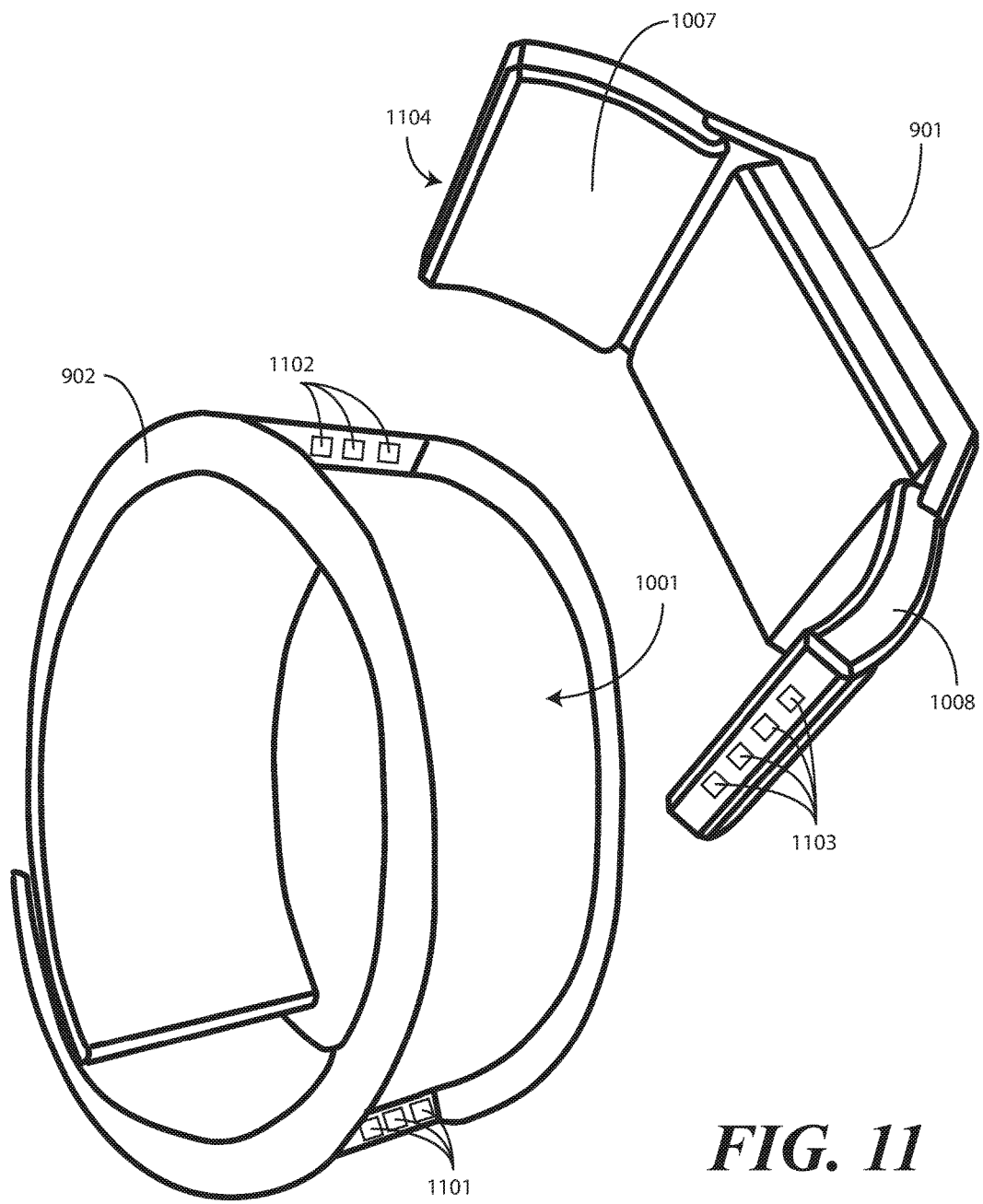

Turning now to FIG. 11, the detachable electronic module 901 has been rotated to reveal electrical couplings 1101, 1102, 1103, 1104 that allow the detachable electronic module 901 and the active strap 902 to work in tandem. In this illustrative embodiment, the attachment bay 1001 includes electrical couplings 1101, 1102 that mate with complementary electrical couplings 1103, 1104 disposed on the electronic module extensions 1007, 1008. The location of these electrical couplings 1101, 1102, 1103, 1104 is illustrative only. Other electrical coupling embodiments will be described below.

Figure 12:
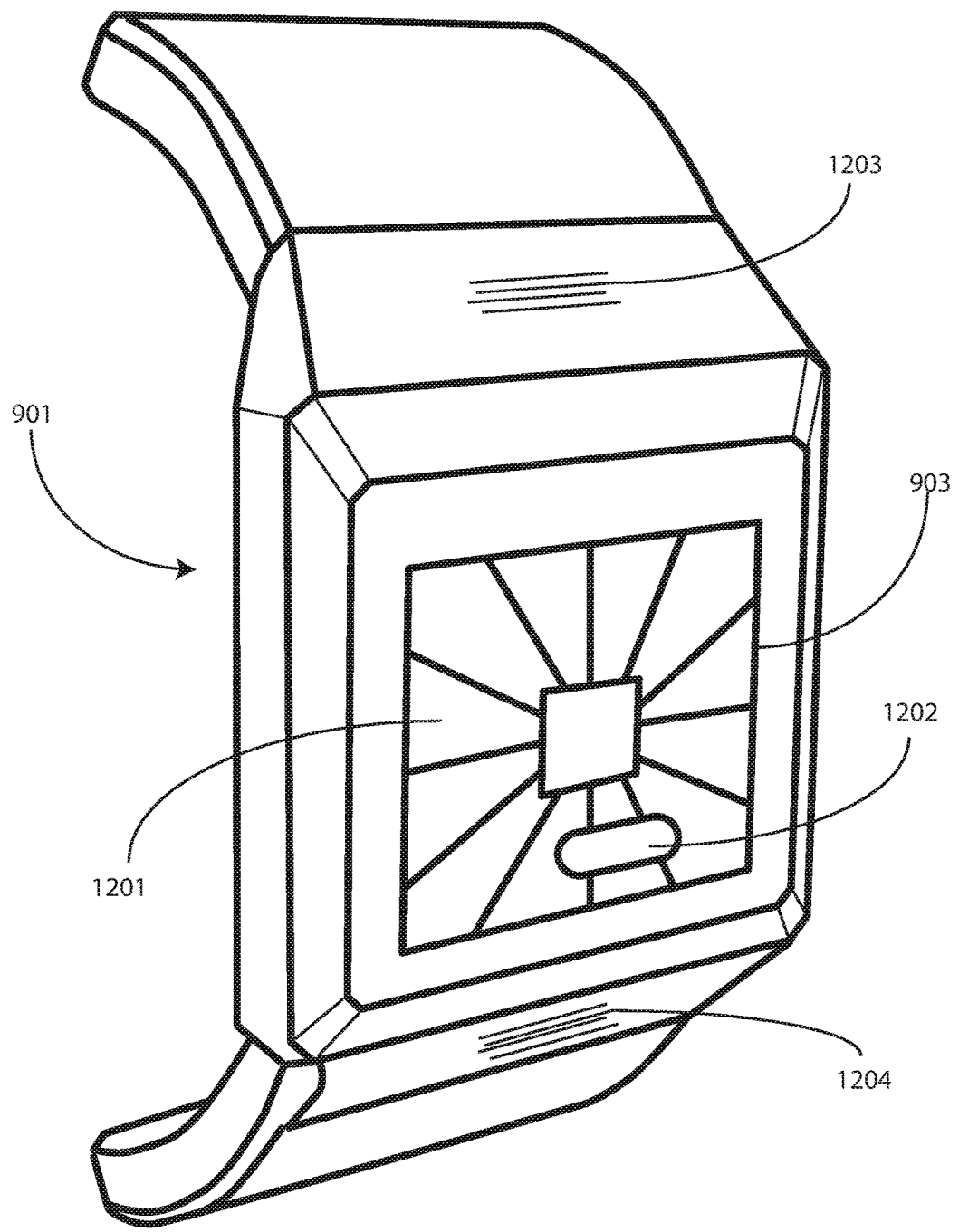

Turning to FIG. 12, the detachable electronic module 901 is shown by itself with one example of visual output 1201 being presented on the touch sensitive display 903. The visual output 1201 in this embodiment is a telephone dialer, as the detachable electronic module 901 is operating in a telephone mode. As noted above, in one or more embodiments, the control circuit (301) of the detachable electronic module 901 can be configured to alter one of a color, a resolution, a scaling, an operating mode, or a magnification of the visual output 1201. For example, one or more of these characteristics can be altered when the control circuit (301) alters altering the presentation orientation of the visual output 1201 in response to the user input.

This can be understood with a simple use case. Presume that a user is wearing the detachable electronic module 901 on his wrist. A friend asks the user to dial a local restaurant. The friend knows the number, but the user does not. Rather than the friend having to say the number to the user, the user may simply make a gesture, such as a swipe of his arm towards the friend. This gesture, sensed by the accelerometer (313) is a user input. Upon detecting this user input, a presentation module operable with the display can alter a presentation orientation of visual output 1201 from an initial orientation, shown in FIG. 12, to a second orientation, which may be rotated a predetermined rotation amount, e.g., 180 degrees from the initial orientation. The friend can then dial the number using the telephone dialer shown in FIG. 12. When the mobile communication circuit (303) makes a connection with the restaurant, this represents an event occurring in the absence of further user input. Accordingly, the presentation module can revert the presentation orientation to the initial orientation, thus indicating to the user that a call has been established. In addition, the presentation module may present a prompt 1202 on the touch sensitive display 903 when the call was connected.

Now suppose that both the friend and user need to speak with the restaurant. In one embodiment, the user may employ gestures to make the communication more efficient. For example, during the call, when it is the friend's turn to speak, the user may make the same arm gesture of swiping his arm towards the friend. In one embodiment, two speakers 1203, 1204 are provided, each having a differently oriented acoustic output cone. The two speakers 1203, 1204 thus form a directable audio output. When the user makes the gesture, the control circuit (301) can further to redirect output audio in addition to altering the presentation orientation. The same can occur with multiple microphones. The control circuit (301) can switch between audio input devices upon altering the presentation orientation in response to the user input.

Figure 13:
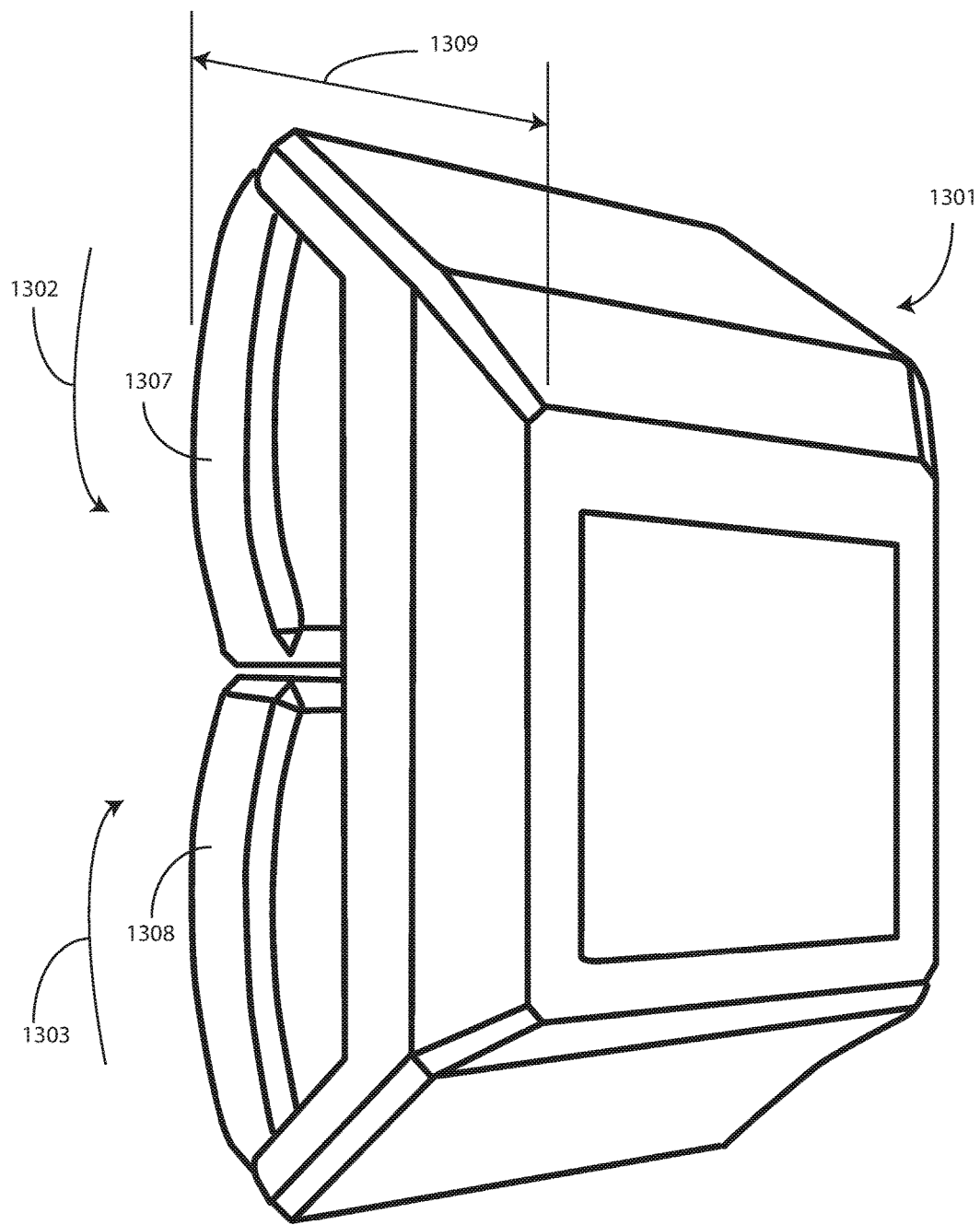
FIG. 13 illustrates one explanatory electronic device having collapsible components configured in accordance with one or more embodiments of the invention.

Turning to FIG. 13, illustrated therein is an optional mechanical feature associated with one detachable electronic module 1301 configured in accordance with one or more embodiments of the invention. As shown in FIG. 13, the electronic module extensions 1307, 1308 are coupled to the detachable electronic module 1301 with folding hinges and have been folded 1302, 1303 about the rear side of the detachable electronic module 1301. This position is referred to a "closed" position because the electronic module extensions 1307, 1308 are disposed against a major face, i.e., the back surface, of the housing of the detachable electronic module 1301. This collapsible feature allows the detachable electronic module 1301 to become a more compact device when being used in the absence of a passive or active strap. Additionally, as will be described in more detail below, the collapsible feature can allow a user to alter the operational modes of the detachable electronic module 1301 by moving, i.e., pivoting or rotating, the electronic module extensions 1307, 1308 relative to the central housing of the detachable electronic module 1301.

In this illustrative embodiment, each electronic module extension 1307, 1308 is equipped with pivoting power and ground contacts so that power from the cells disposed within the electronic module extensions 1307, 1308 is delivered to the control circuit and other components in the detachable electronic module 1301 regardless of their radial orientation relative to the detachable electronic module 1301. In this illustrative embodiment, the detachable electronic module 1301 has a thickness 1309 of between twenty and thirty millimeters.

While the electronic module extensions 1307, 1308 are shown completely folded in FIG. 13, it should be noted that the folding hinges can be configured to be resistive so as to be pivotable to any number of rotational orientations as desired by a user. For example, each electronic module extension 1307, 1308 can be rotated halfway so as to serve as a stand when the detachable electronic module 1301 is placed on its side. In one or more embodiments, the electronic module extensions 1307, 1308 are coupled to the central housing of the detachable electronic module with a detented hinge that provides pseudo mechanical stops so that the electronic module extensions 1307, 1308 can be easily stopped at a variety of pre-defined angularly displaced orientations relative to the central housing of the detachable electronic module 1301. In such an embodiment, the detented hinge comprises a plurality of detent stops configured to hold the one or both of the first electronic module extension 1307 or the second electronic module extension 1308 in one of a plurality of angularly displaced alignments relative to the housing.

Figure 14:
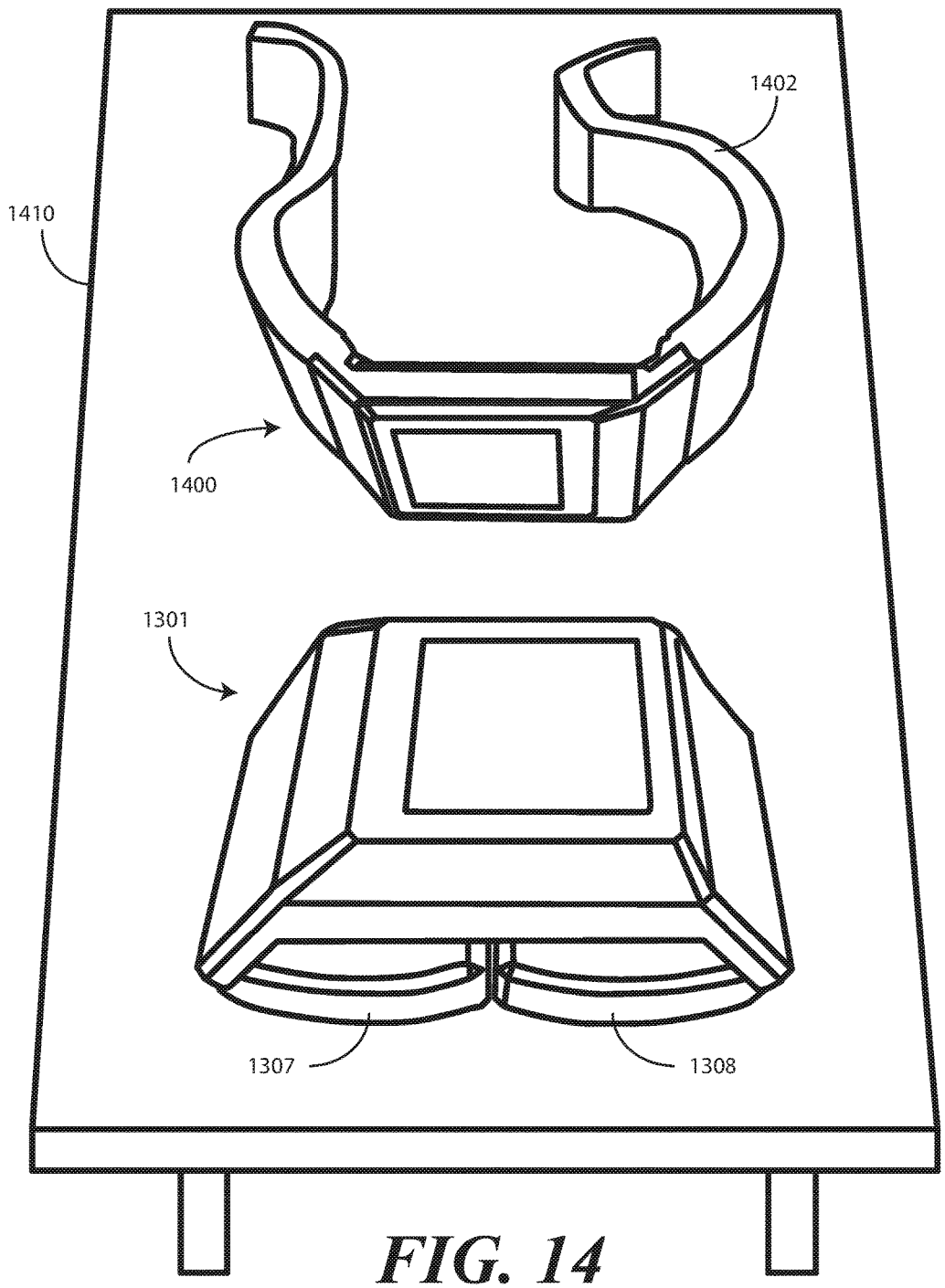
FIG. 14 illustrates an explanatory wearable component having been separated from an explanatory electronic device configured in accordance with one or more embodiments of the invention.

Turning to FIG. 14, illustrated therein are the detachable electronic module 1301 of FIG. 13 and an electronic device 1400 placed on a table 1410. FIG. 14 illustrates a few of the many options for using the electronic devices configured in accordance with embodiments of the invention when not being worn. The electronic module extensions 1307, 1308 have been folded about detachable electronic module 1301. The detachable electronic module 1301 has then been placed face up, with each electronic module extension 1307, 1308 serving as a stand. This configuration can be useful, for example, when multiple people are using the detachable electronic module 1301 as a speakerphone during a group call. Further, the active strap to which the detachable electronic module 1301 was coupled can remain on the wrist performing wellness monitoring. With electronic device 1400, the active strap 1402 has been straightened from its wearable configuration to serve as a stand. This configuration can be useful, for example, when using the electronic device 1400 as an alarm clock.

Figure 15:
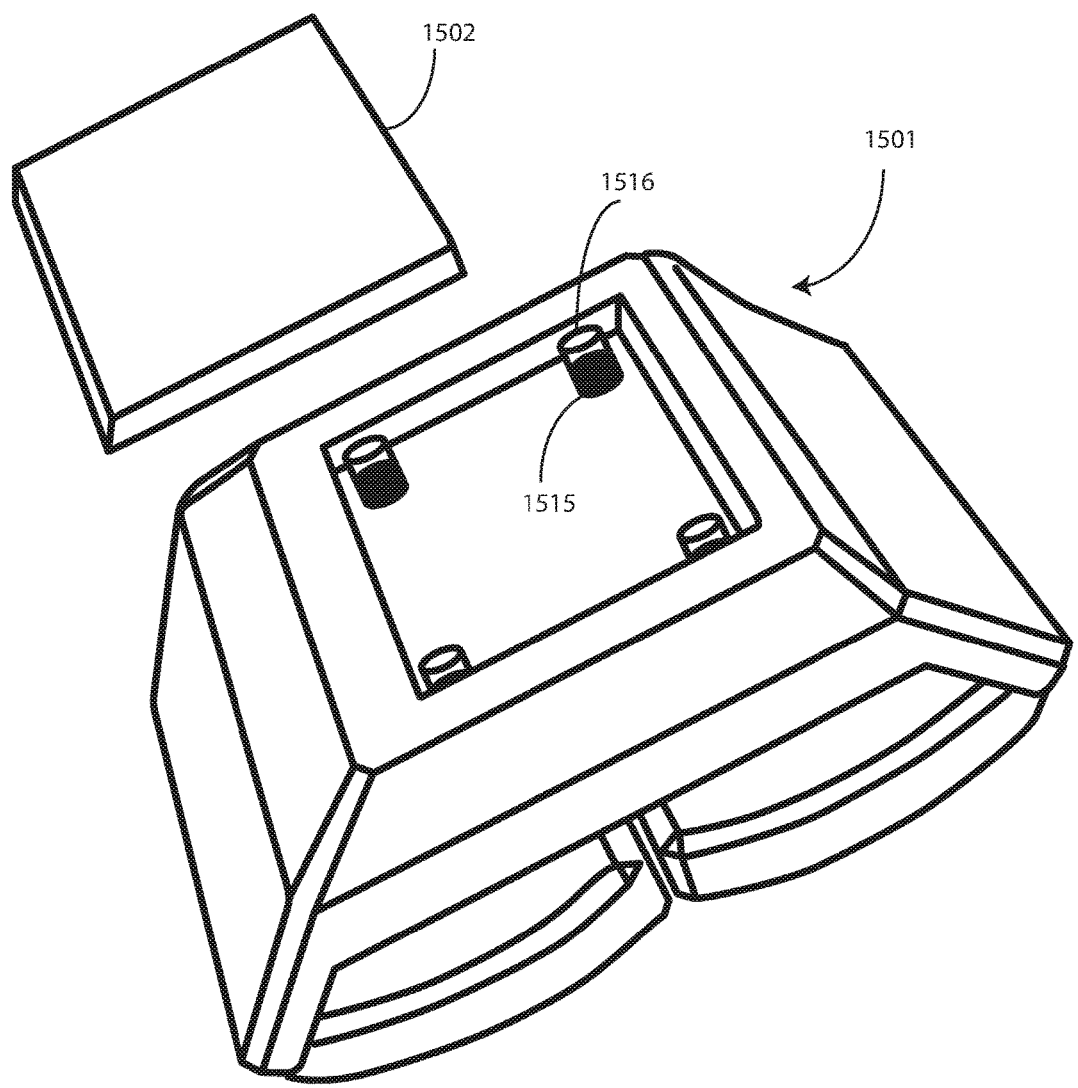
FIG. 15 illustrates an exploded view of one explanatory electronic device having a display lens configured as an acoustic output transducer in accordance with one or more embodiments of the invention.

Turning now to FIG. 15, a detachable electronic device 1501 having piezoelectric devices 1515 configured work with the cover layer 1502 of the display to provide input and output capabilities. Piezo frame elements 1516 function as mechanical couplers between the cover layer 1502 and the piezoelectric devices 1515. The control circuit disposed within the detachable electronic device 1501 is operable with the piezoelectric devices 1515. The control circuit can actuate the piezoelectric devices 1515 to employ them as output devices. Alternatively, when forces act upon the piezo frame elements 1516, those forces are transferred to the piezoelectric devices 1515, thereby delivering signals to the control circuit. Accordingly, the piezoelectric devices 1515 can be used as either input or output devices.

The inclusion of the piezoelectric devices 1515 provides many advantageous functions to the detachable electronic device 1501. As noted above, when the cover layer 1502 is touched or pressed by a user, the cover layer 1502 becomes an input control device for receiving user input. The piezoelectric devices 1515 can sense this input and deliver a corresponding signal to the control circuit. By using multiple piezoelectric devices 1515 that are spread out within the detachable electronic device 1501, the signals can be read individually to determine an approximate location along the cover layer 1502 contacted by the user. In this manner, the cover layer 1502 can be used as a navigation device by defining, for example, a "left edge press" with a different function from a "right edge press," and so forth.

The cover layer 1502 can also be used as an output. In one or more embodiments, the control circuit actuates the piezoelectric devices 1515 in accordance with an audio signal to use the cover layer 1502 as an audio transducer. Accordingly, the cover layer becomes a loudspeaker through which audio output can be delivered to a user. In some embodiments, the control circuit can actuate the piezoelectric devices 1515 in accordance with pulse functions to deliver haptic feedback to the user as well.

Figure 16:
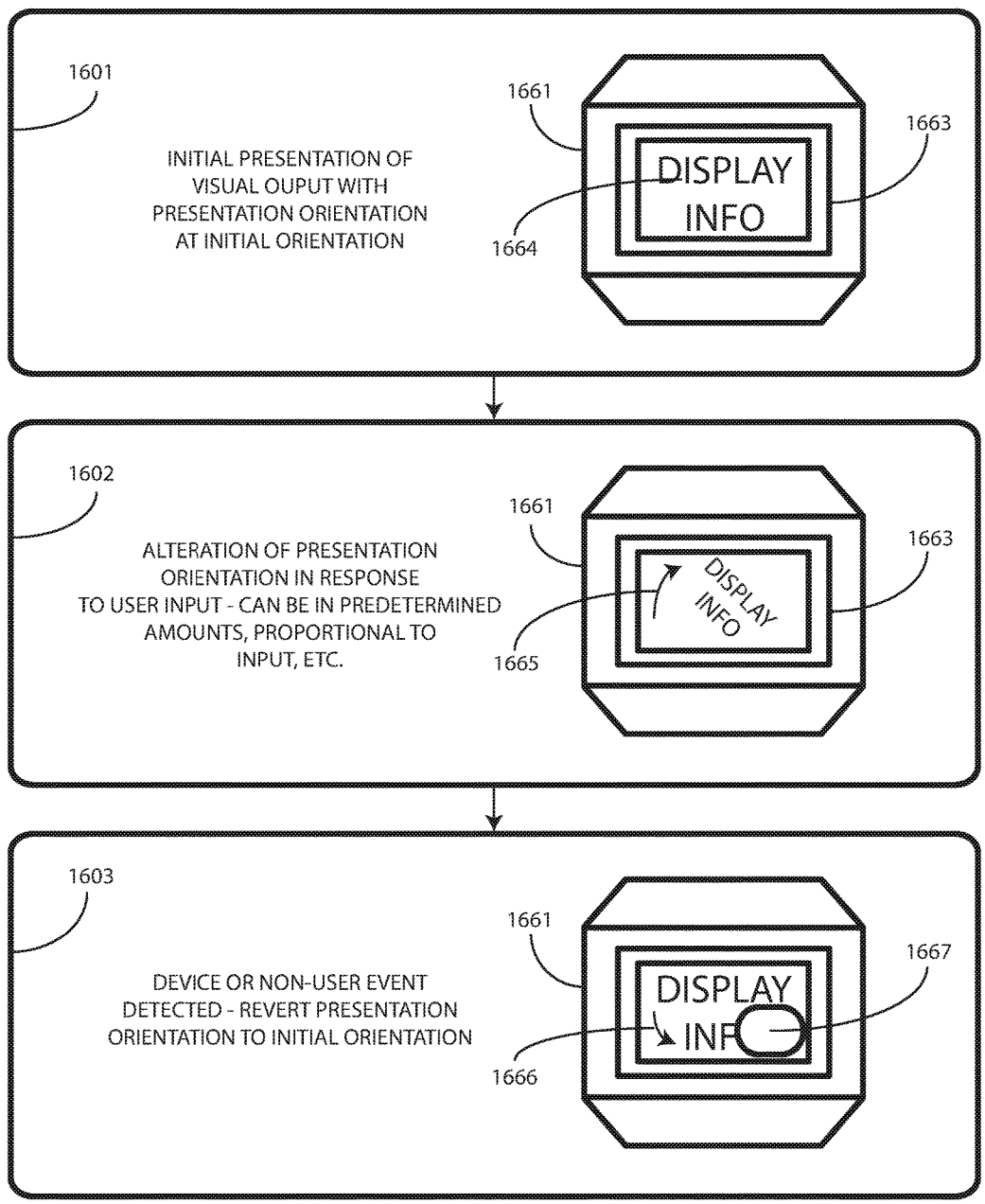
FIG. 16 illustrates a method for orienting images on a display of a device in accordance with one or more embodiments of the invention.

Turning now to FIG. 16, illustrated therein is a method, suitable for an electronic device, for orienting images on a display in accordance with one or more embodiments of the invention. As shown at step 1601, a display 1663 of an electronic device 1661 is configured to provide visual output 1664 having a presentation orientation associated therewith. As step 1601 is the initial step in the method, the presentation orientation of the visual output 1664 is the initial orientation.

At step 1602, user input is received by an interface element of the electronic device 1661. The user input can take a variety of forms. For instance, in one embodiment the user input comprises audio input. In another embodiment, the user input comprises touch input along the display 1663. In another embodiment, the user input comprises actuation of an input control device, such as a button, joystick, slider switch, rocker switch, or other device, that is operable with a control circuit disposed within the electronic device 1661. In another embodiment, the user input comprises a sensed gesture, such as movement of a body part to which the electronic device is connected, which may be sensed by an accelerometer or gyroscope. In another embodiment, the user input comprises a light-sensed user action or an infrared-sensed user action, such as movement of the user's body, hands, or limbs away from the electronic device 1661.

In response to the user input, the control circuit coupled to the display can be configured to alter 1665 the presentation orientation from the initial orientation. As shown in illustrative step 1602, the alteration comprises a rotation of the presentation orientation in the clockwise direction. Note that it is not necessary to rotate or move the display 1663 to change the presentation orientation. For instance, the display 1663 can remain stationary in three-dimensional space while the presentation orientation of the visual output 1664 rotates or otherwise changes with reference to the physical orientation of the display 1663. Note also that the amount of alteration can depend upon the configuration of the electronic device 1661, the user input, or a combination of the two. For example, in one embodiment, the control circuit can be configured to alter 1665 the presentation orientation in an amount proportional to the user input. Where the user input comprises a finger sweep across a surface of the electronic device 1661 or the display 1663, the control circuit may alter 1665 the presentation in a proportional amount and in a corresponding direction. However, other alteration schemes are possible as well. For instance, when a cover layer of the display 1663 is configured as an input control device, the control circuit may be configured to alter 1665 the presentation orientation by a predetermined rotation amount when the input control device is actuated. A press of the cover layer may result in, for example, a 90-degree, 180, degree, or other amount of rotation. Predetermined rotation amounts can be associated with other user inputs as well, including gestures. Repeated presses of the cover layer may result in additional rotation of the predetermined amount, for example, one press of the cover layer resulting in a 90-degree rotation, with a second press resulting in an additional 90-degree rotation for a total of 180 degrees, and so forth.

In addition to rotation, the control circuit can be configured to perform other alterations in response to user input as well. The control circuit can be configured to alter one of a color, a resolution, a scaling, or a magnification of the visual output upon altering the presentation orientation in response to the user input. Other alterations will be obvious to those of ordinary skill in the art having the benefit of this disclosure.

At step 1603, a non-user event occurs. Non-user events are events that occur in the absence of user input to user interface devices. Non-user events can take a variety of forms. Non-user events can be user defined as well. Examples of non-user events include incoming telephone calls, an incoming text message, an incoming multimedia message, a low battery warning, expiration of a timer, or a calendar alarm event. Where the electronic device 1661 includes wellness sensors, the non-user input event comprises a detected user wellness condition sensed by the user wellness sensors. Detected wellness events are non-user events because they do not result from manipulation of user interface devices, but rather from signals sensed from user monitoring devices, e.g., the wellness sensors (334) described above with reference to FIG. 3.

When the non-user event occurs, the control circuit is configured to revert 1666 the presentation orientation back to the initial orientation. This not only returns the presentation orientation to one that is generally most readily accessible by the user, but also serves as a notification that the non-user event has occurred. The control circuit can optionally take additional steps as well, such as presenting a prompt 1667 on the display after reverting the presentation orientation to the initial orientation.

Figure 17:
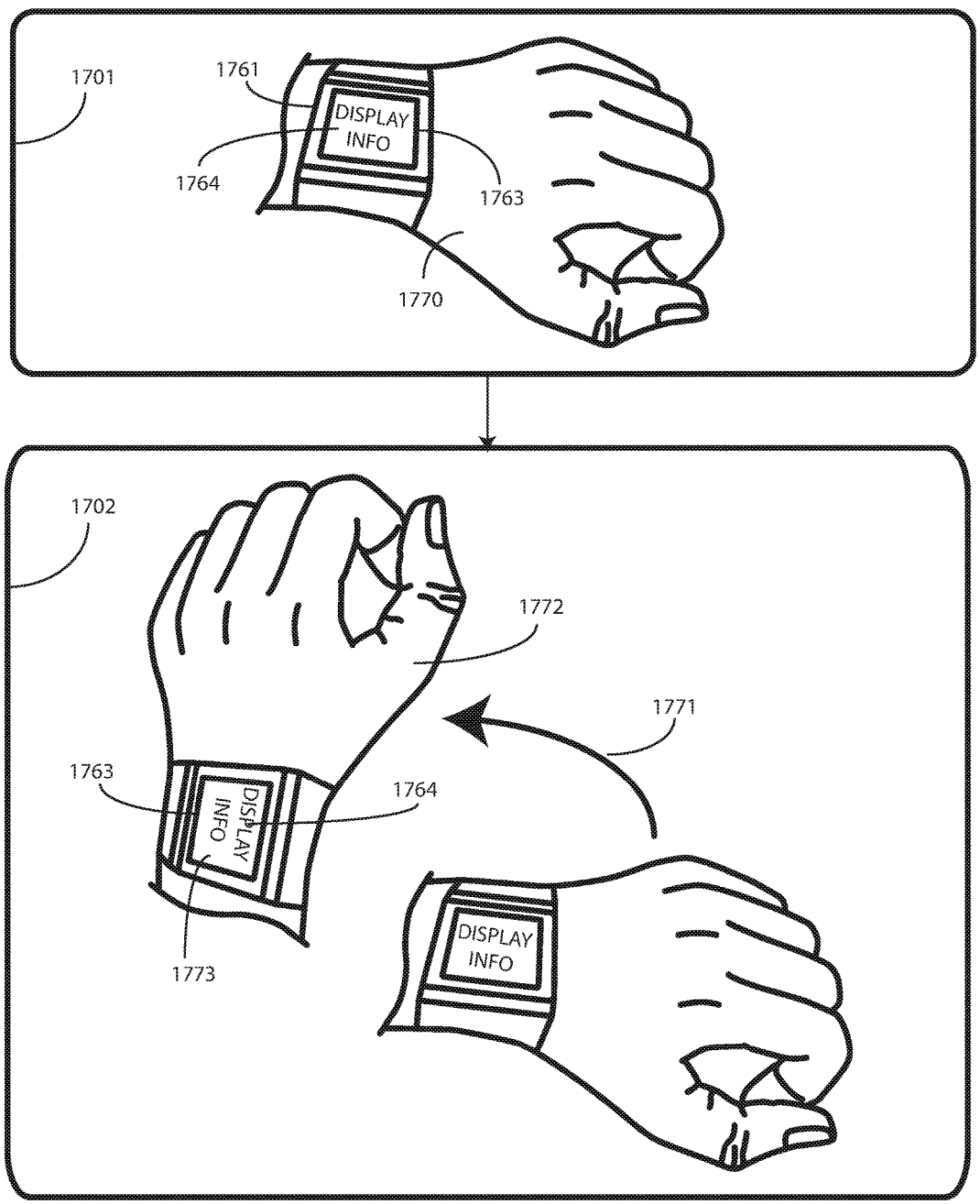
FIGS. 17-18 illustrate one method for altering the presentation orientation of visual output on an explanatory wearable electronic device by way of a gesture in accordance with one or more embodiments of the invention.
Figure 18:
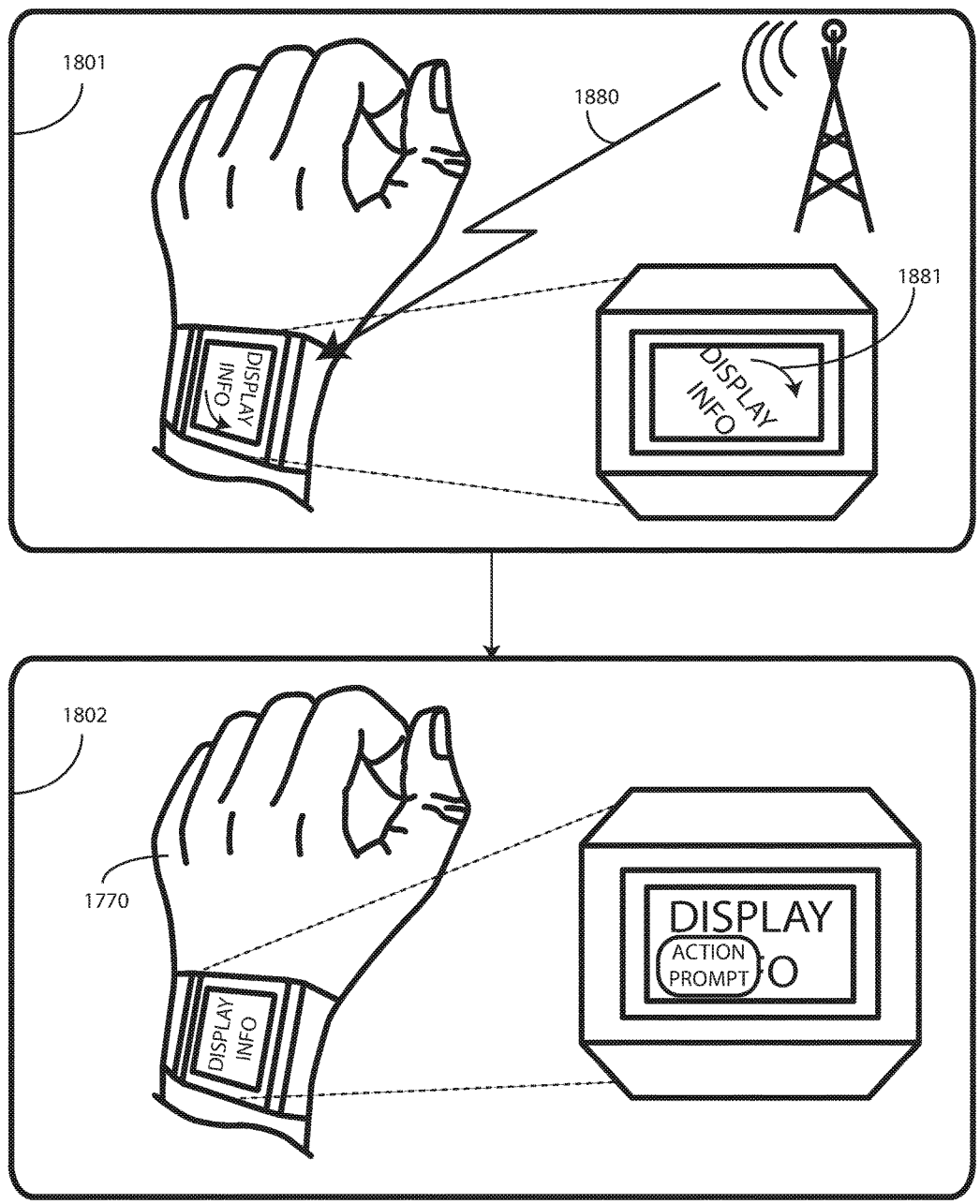

Turning now to FIGS. 17-18, the method described with reference to FIG. 16 will be illustratively described. Starting at step 1701, a user 1770 has a wearable electronic device 1761 strapped to his wrist. The display 1763 of the wearable electronic device 1761 presents visual output 1764 with a presentation orientation that is an initial orientation.

At step 1702, the user makes a gesture 1771, which in this illustration is a sweeping motion of his hand 1772. A motion detector disposed in the wearable electronic device 1761, which may be an accelerometer or gyroscope, senses the motion caused by this gesture 1771 and delivers a signal corresponding thereto to a control circuit. Upon receiving the user input, the control circuit alters the presentation orientation from the initial orientation to a second presentation orientation 1773. In this illustration, the second presentation orientation is a predetermined rotation amount of 180 degrees, thus causing the visual output 1764 to "flip" upside down on the display 1763.

At step 1801, an event occurring in absence of further user input occurs. In this illustration, the event is an incoming telephone call 1880. Upon detecting this non-user event, the control circuit reverts 1881 the presentation orientation of the visual output on the display to the initial orientation. The initial orientation is shown in step 1802. Note that this has transpired without additional gestures by the user. However, in this illustrative embodiment, the same would be true if there had been gestures, because the control circuit is configured to revert the presentation orientation of the visual output on the display to an initial orientation independent o fuser input when a non-user event is detected.

Figure 19:
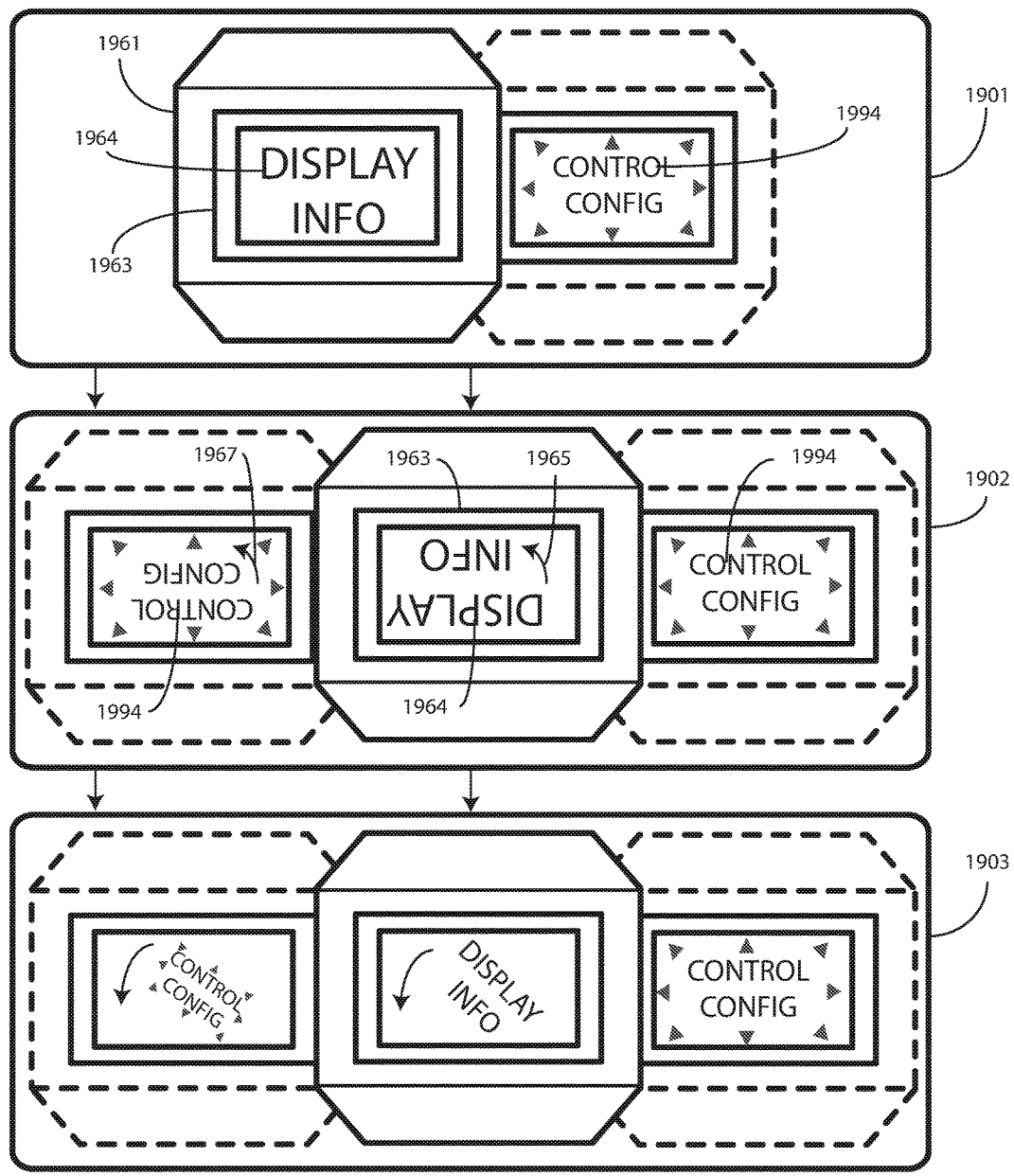
FIG. 19 illustrates one method of altering the presentation orientation of visual output on an explanatory wearable electronic device with either simultaneously altering the orientation of a user interface or retaining an initial disposition of the user interface in accordance with one or more embodiments of the invention.

Turning now to FIG. 19, illustrated therein is another method for orienting visual output 1964 on the display 1963 of an electronic device 1961 in accordance with one or more embodiments of the invention. In FIG. 19, the visual output 1964 has associated therewith a user input configuration. The user input configuration 1994 comprises actuation targets or other user controls that, when actuated, provide user input to the electronic device 1961. For instance, where the display 1963 is a touch sensitive display, the user input configuration 1994 forms a user interface with which a user may control the operation and functionality of the electronic device 1961. The user input configuration 1994 can include visual or non-visual user actuation targets present on the display 1963 of the electronic device 1961. Alternatively, the user input configuration can be a configuration of a morphing or otherwise configurable keypad, e.g., smart keys, or user interaction device disposed along a surface of the electronic device 1961.

Illustrating by example, the telephone dialer shown in FIG. 12 would have a user input configuration associated therewith because touching any of the dialers in the telephone dialer would correspond to user entry of a telephone number to be dialed. In another example, presume that the electronic device 1961 included three configurable buttons on its left side. In one mode of operation, actuation of the top button results in the visual output 1964 scrolling up, while actuation of the bottom button results in the visual output 1964 scrolling down. Actuation of the center button causes a soft user actuation target on the display 1963 highlighted in the visual output 1964 to be executed. The user input configuration 1994 associated with the visual output 1964 would be the configuration of the configurable buttons.

At step 1901, a control circuit of the electronic device 1961 presents the visual output 1964 on the display 1963 in an initial orientation. The user input configuration 1994 is presented in an initial disposition as well. The initial disposition of the user input configuration 1994 is oriented the same as the presentation orientation of the visual output 1964.

At step 1902, user input is received. As described above, the control circuit alters 1965 the presentation orientation of the visual output 1964 in response to the user input. The control circuit can then take one of a variety of options with the user input configuration 1994 depending upon the application running on the electronic device 1961, how the user has defined the control settings of the electronic device 1961, user preferences, or other factors.

In a first embodiment, shown to the left of the electronic device 1961 in step 1902, the control circuit is configured to alter 1967 the initial disposition of the user input configuration 1994 in response to the user input. In one embodiment, the control circuit is configured to alter 1967 the initial disposition of the user input configuration 1994 proportionally with the alteration of the presentation orientation of the visual output 1964. However, the initial disposition of the user input configuration 1994 could be altered in amounts different from the visual output 1964 as well.

In a second embodiment, shown to the right of the electronic device 1961 in step 1902, the control circuit is configured to retain the user input configuration 1994 in the initial disposition when the presentation orientation is altered in response to the user input. This second embodiment is advantageous when, for example, a user is showing pictures to a colleague on the display 1963. The user may wish to flip the picture, i.e., flip the visual output 1964 over so that the colleague can see it. However, the user may wish to retain the user input configuration 1994 so as not to have to scroll backwards. If the presentation of pictures has associated therewith a user input configuration 1994 that causes leftward scrolling when the left side of the display 1963 is pressed, and rightward scrolling when the right side of the display 1963 is pressed, without the ability to retain the user input configuration 1994 when altering the presentation orientation, the user would have to press left to scroll right and vice versa. The ability to retain the initial disposition of the user input configuration 1994 allows the user to retain the intuitive, properly oriented scrolling control while simultaneously flipping a picture associated with that control around so as to be visible to a friend.

Figure 20:
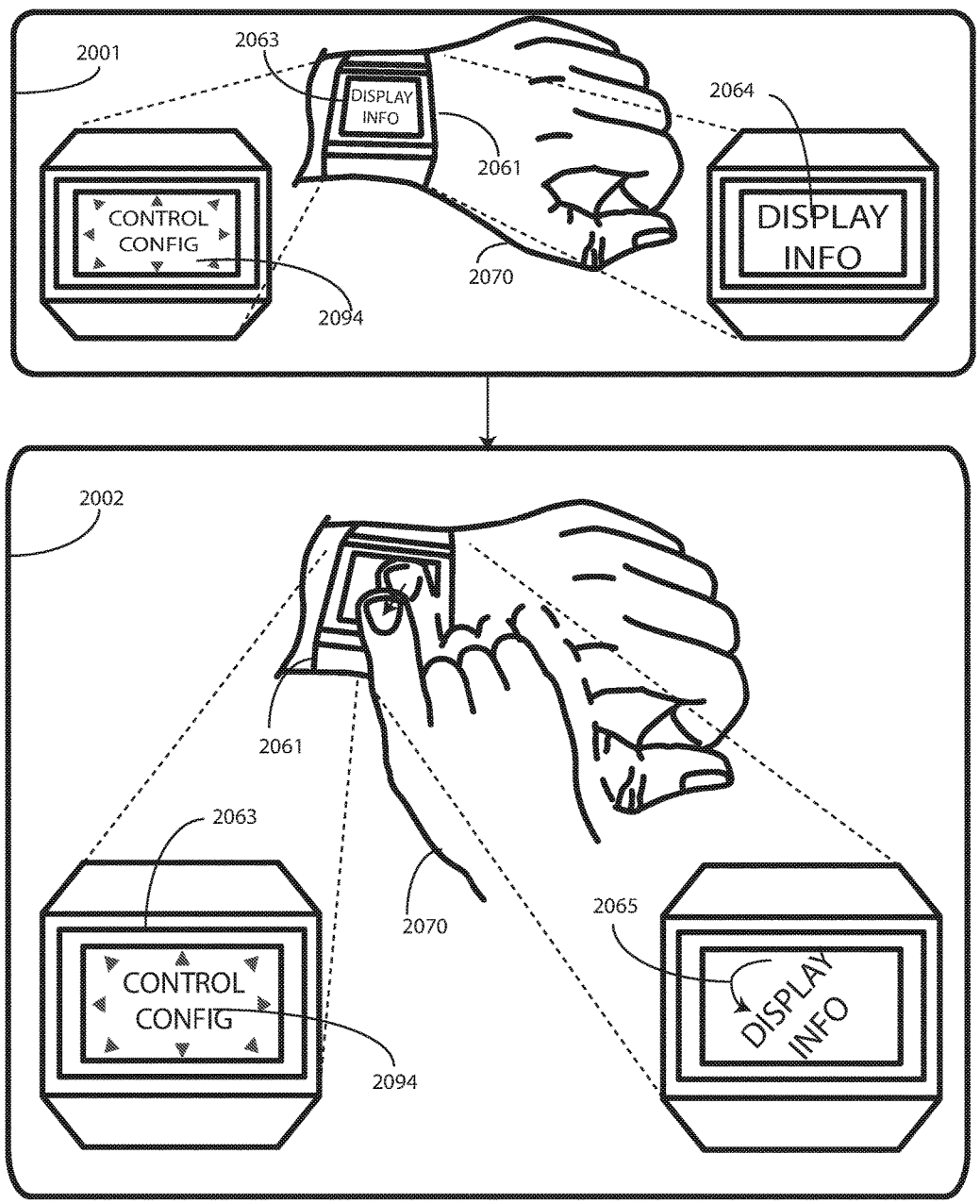
FIGS. 20-21 illustrate one method of altering the presentation orientation of visual output on an explanatory wearable electronic device in response to user input while retaining an initial disposition of an associated user interface relative to device geometry in accordance with one or more embodiments of the invention.
Figure 21:
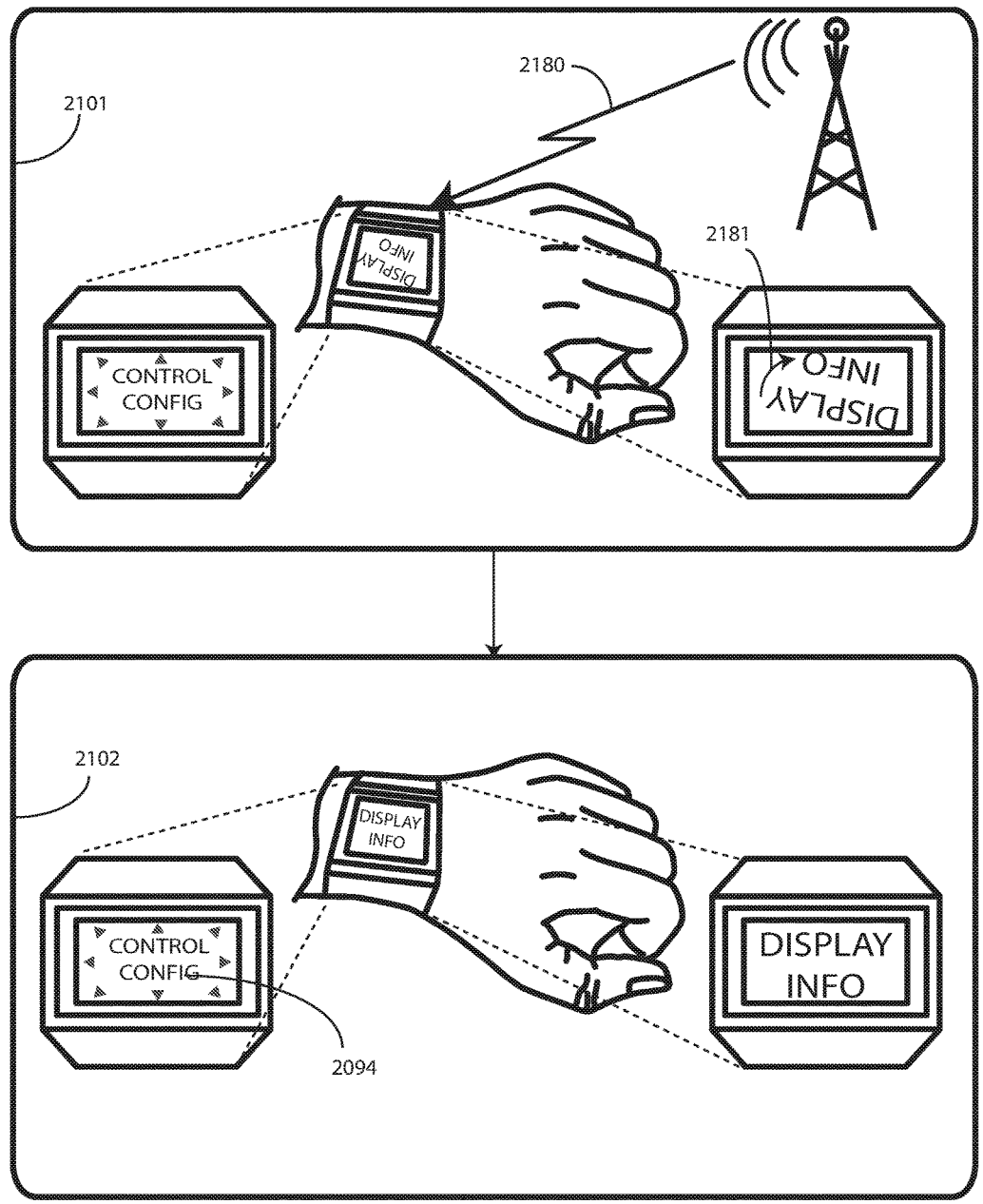

Turning to FIGS. 20-21, the method of FIG. 19 will be graphically described. Starting at step 2001, a user 2070 has a wearable electronic device 2061 strapped to his wrist. The display 2063 of the wearable electronic device 2061 presents visual output 2064, which in this case is a picture that the user 2070 wishes to show to a friend who is facing him. The visual output 2064 is presented with presentation orientation that is an initial orientation. In this example, the bottom of the picture is towards the user 2070.

The visual output 2064 also has associated therewith a user interface 2094. As the visual output 2064 is being presented in a photo-displaying application, the application is configured such that certain finger gestures cause certain actions to occur. For simplicity of discussion, presume that touching a left side of the display 2063 scrolls to a previous picture, while touching a right side of the display 2063 scrolls to a subsequent picture. As shown at step 2001, the initial disposition of the user interface 2094 is oriented with the initial orientation of the visual output 2064.

At step 2002, the user 2070 delivers user input to the wearable electronic device 2061. The user input in this example is a swirling motion made with a finger on the display 2063. This causes the presentation orientation of the visual output to be altered 2065. However, to preserve a common navigation control scheme, the initial disposition of the user interface 2094 is retained. Thus, the user can still touch a left side of the display 2063 to scroll to a previous picture, while touching a right side of the display 2063 will scroll to a subsequent picture.

At step 2101, a non-user event occurs. In this illustration, the non-user event is an incoming telephone call 2180. Upon detecting this non-user event, the control circuit reverts 2081 the presentation orientation of the visual output on the display to the initial orientation. The initial orientation is shown in step 2102. Since the user interface 2094 was retained in step 2002 above, it does not need to be altered.

Figure 22:
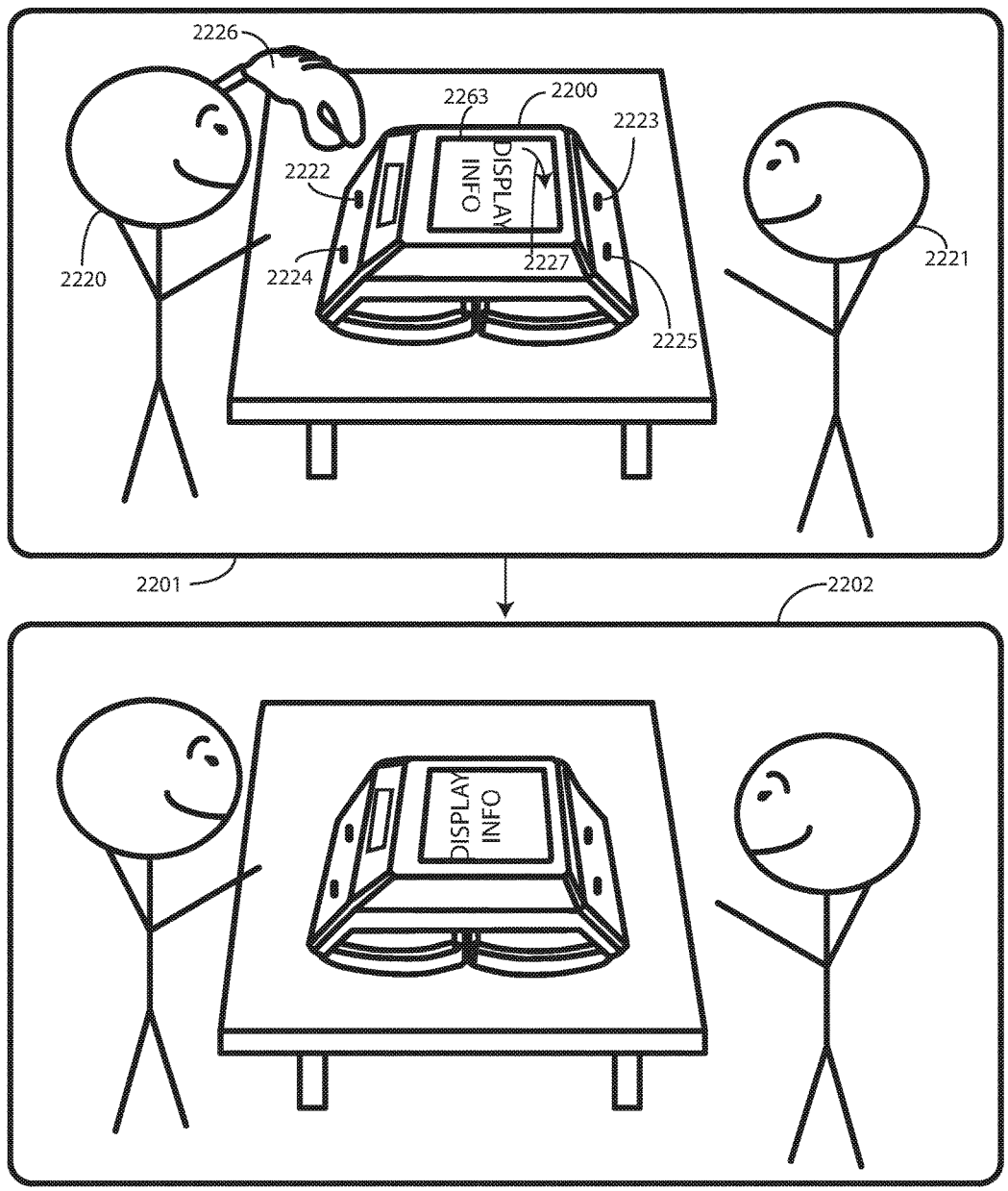
FIGS. 22-23 illustrate one method of altering the presentation orientation of visual output on an explanatory wearable electronic device in response to user input and reverting the presentation orientation to an initial orientation in response to a detected event in accordance with one or more embodiments of the invention.
Figure 23:
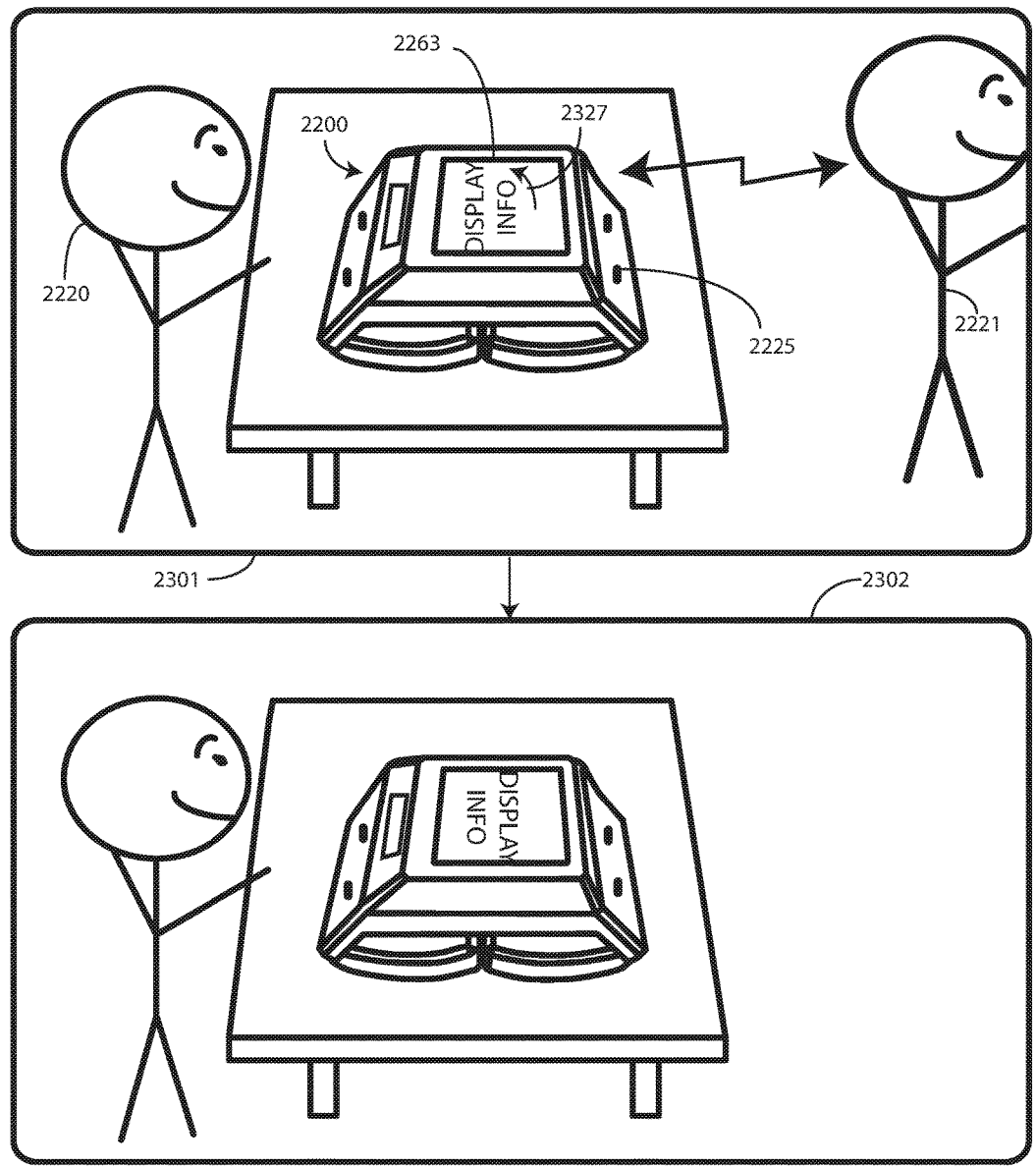

Turning now to FIGS. 22-23, illustrated therein is another use case that can occur using electronic devices configured in accordance with embodiments of the invention. At step 2201, a first user 2220 and a second user 2221 are engaged in a conference call, with a detachable electronic module 2200 in a folded configuration being used as the communication device. Initially, the first user 2220 is speaking. Accordingly, the visual output 2263 is oriented towards the first user 2220. The detachable electronic module 2200 of this illustration includes a plurality of audio input devices, with one audio input device 2222 being disposed such that its audio receive cone is directed towards the first user 2220. The second audio input device 2223 is disposed such that its audio receive cone is oriented towards the second user 2221. Similarly, the detachable electronic module 2200 also includes a directable audio output comprising a first speaker 2224 directed to the first user 2220 and a second speaker 2225 directed towards the second user 2221.

While the first user 2220 is speaking, not only is the visual output 2263 oriented toward the first user 2220, but so too are the audio input and the audio output. In step 2201, the first user 2220 finishes speaking and wishes to let the second user 2221 speak. Accordingly, the first user 2220 provides user input by gesturing with a hand 2226. This gesture is detected by an infrared sensor of the detachable electronic module 2200.

In response to detecting the user input, the control circuit is configured to alter 2227 the presentation orientation of the visual output 2263 so that the visual output 2263 is oriented towards the second user 2221. The control circuit of this example further is operable to switch between audio input devices 2222, 2223 upon altering the presentation orientation in response to the user input. In one embodiment, the switching results in the first audio input device 2222 being turned off and the second audio input device 2223 being turned on. Further, the control circuit is operable to redirect output audio upon altering the presentation orientation in response to the user input. This can include increasing the volume of the second speaker 2225 while reducing the volume of the first speaker 2224. The result of these alterations is shown in step 2202.

At step 2301, the second user 2221 is finished talking and leaves the room. With reference to the first user 2220, this constitutes a non-user event because it occurs in the absence of user input from the first user 2220. The infrared sensor of the detachable electronic module 2200 detects the second user 2221 leaving. Accordingly, the control circuit reverts 2327 the presentation orientation of the visual output 2263 back to the first user 2220. Simultaneously, the control circuit of this example switches between audio input devices to direct the audio input back to the first user 2220. Further, the control circuit redirects output audio upon altering the presentation orientation back to the first user 2220. Since the second user 2221 is no longer in the vicinity of the detachable electronic module 2200, as detected by the infrared sensor, the second speaker 2225 can be turned off. The result of these alterations is shown in step 2302.

The above discussion not withstanding, FIGS. 22 and 23 can be used to illustrate yet another use case that can occur using electronic devices configured in accordance with embodiments of the invention. At step 2201, a first user 2220 and a second user 2221 are engaged in the viewing of content on the detachable electronic module 2200 such as pictures. In this case the first user 2220 is showing the second user 2221 the pictures but controlling the slideshow via voice recognition. Accordingly, the visual output 2263 is oriented towards the first user 2220. The detachable electronic module 2200 of this illustration includes a plurality of audio input devices, with one audio input device 2222 being disposed such that its audio receive cone is directed towards the first user 2220. The second audio input device 2223 is disposed such that its audio receive cone is oriented towards the second user 2221.

While the first user 2220 is manipulating the detachable electronic module 2200 to find the appropriate content to show the second user 2221, not only is the visual output 2263 oriented toward the first user 2220, but so too is the audio input. In step 2201, the first user 2220 finds the content and wishes to show it to the second user 2221. Accordingly, the first user 2220 provides user input by gesturing with a hand 2226. This gesture is detected by an infrared sensor of the detachable electronic module 2200.

In response to detecting the user input, the control circuit is configured to alter 2227 the presentation orientation of the visual output 2263 so that the visual output 2263 is oriented towards the second user 2221. The control circuit of this example remains audio input device 2222 upon altering the presentation orientation in response to the user input. The result of these alterations is shown in step 2202. The result of these alterations allow the second user 2221 to view the images in the correct orientation, while allowing the first user 2220 to control the manipulation of the images via voice commands using the audio input device 2222.

As in the earlier example the presentation orientation can revert back to the first user due to a non-user event such as the second user 2221 leaving. Alternatively, the first user can manually revert the presentation orientation back in his direction by the use of a gesture or voice command.

Figure 24:
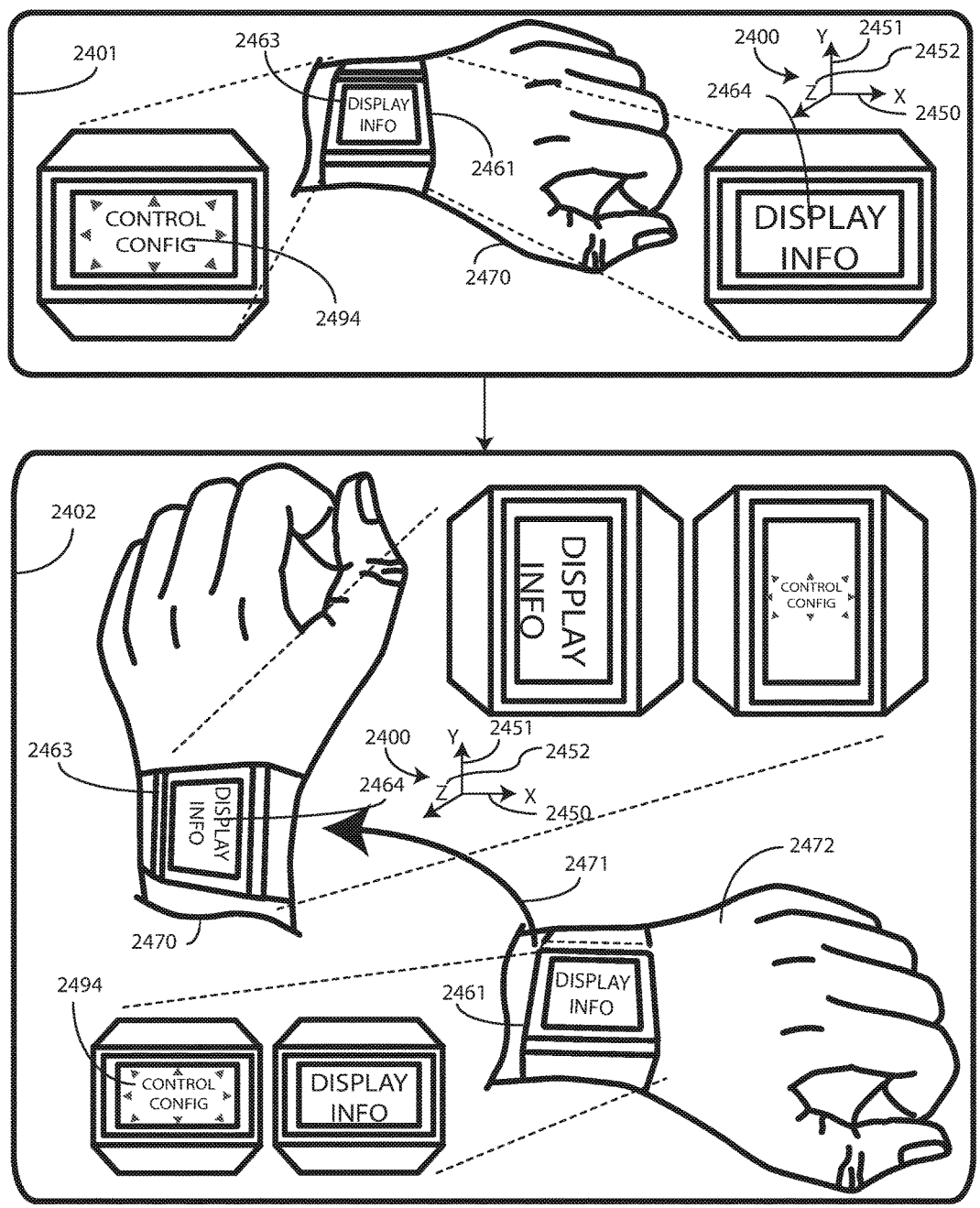
FIGS. 24-25 illustrate one method of altering the presentation orientation of visual output on an explanatory wearable electronic device in response to user input while retaining an initial disposition of an associated user interface relative to a three-dimensional spatial orientation in accordance with one or more embodiments of the invention.
Figure 25:
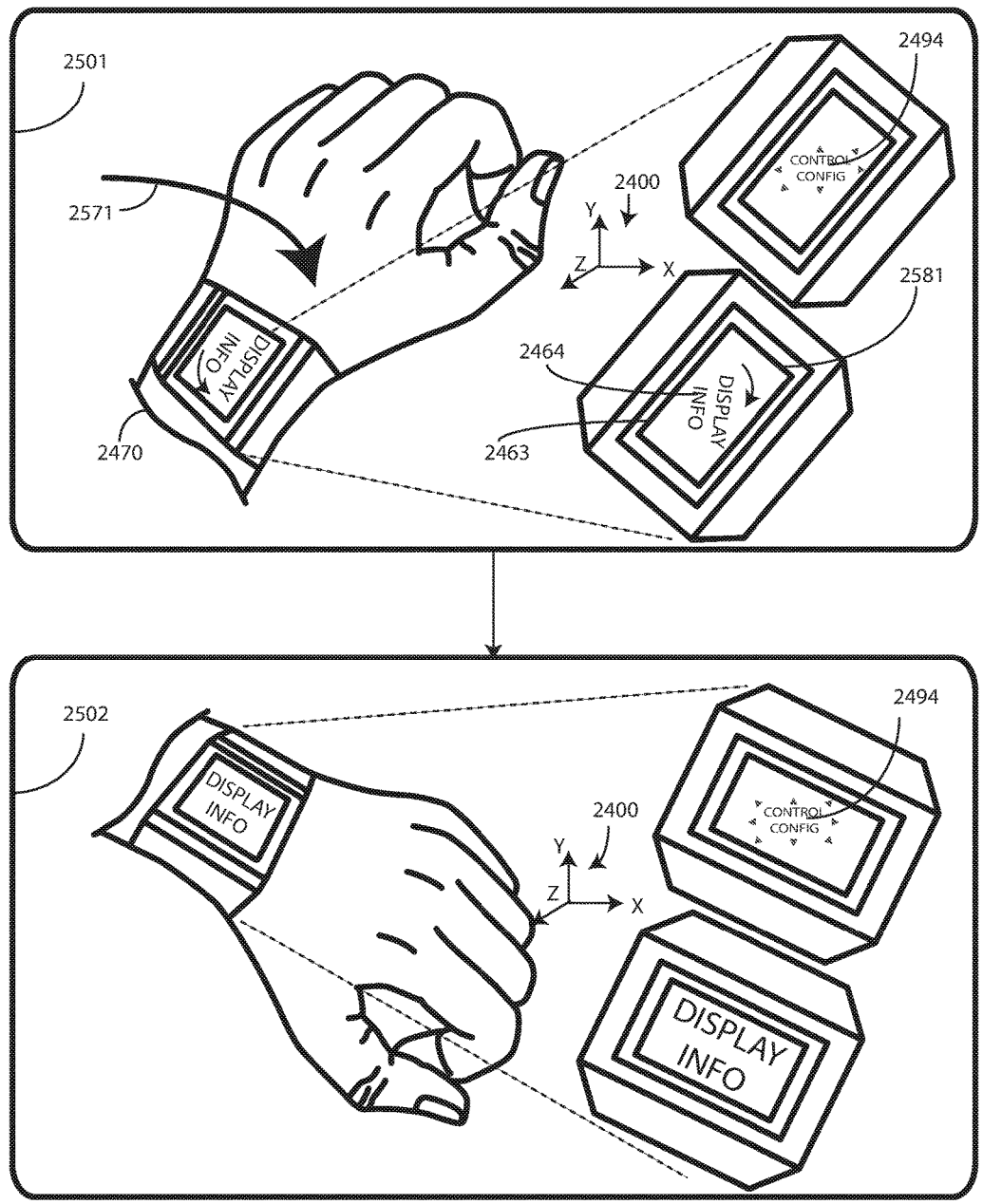

Turning now to FIGS. 24-25, illustrated therein is another method of orienting images on the display of an electronic device 2461 in accordance with one or more embodiments of the invention. Recall from the discussion of FIGS. 19-21 that in one or more embodiments, the control circuit of the electronic device 2461 can be configured to alter the presentation orientation of the visual output 2464 in response to user input while retaining the user interface component 2494 in an initial disposition. The user interface component 2494 is held while the presentation orientation of the visual output 2464 is altered. One of ordinary skill in the art with the benefit of this disclosure will recognize that the retention of the initial disposition of the user interface component 2494 can be with respect to various reference points. For example, the initial disposition can be with reference to the display 2463, the housing of the electronic device 2461, an edge of the display 2463, or other physical element of the electronic device 2461. In such an embodiment, when the electronic device 2461 is moved in three-dimensional space 2400, represented in FIG. 24 by three axes, the user interface component 2494 will remain constantly aligned with, for instance, an edge or corner of the display. This embodiment was illustrated in FIG. 20, where the user interface (2094) was retained in an initial disposition fixed relative to the physical orientation of the display (2063).

In another embodiment, the retention of the initial disposition of the user interface component 2494 can be with reference to its initial bearing in three-dimensional space 2400. Said differently, where the initial disposition of the user interface component 2494 is represented in three-dimensional space 2400 with a bearing along the x-axis 2450, the y-axis 2451, and the z-axis 2452 in three-dimensional space 2400, these bearings can be held while the visual output 2464 is altered. It is this latter embodiment that is shown in FIGS. 24-25.

Starting at step 2401, a user 2470 has an electronic device 2461 strapped to his wrist. The display 2463 of the electronic device 2461 presents visual output 2464 with a presentation orientation that is an initial orientation. The visual output 2464 is presented with presentation orientation that is an initial orientation. In this example, the bottom of the visual output 2464 is towards the body of the user 2470. The visual output 2464 also has associated therewith a user interface component 2494. The user interface component 2494 could comprise a plurality of user actuation targets, a data entry surface, such as one that can be written on with a stylus or other device, a configuration of physical keys, soft keys, or combinations thereof, a preferred voice input direction, or other user input devices. As shown at step 2401, the initial disposition of the user interface component 2494 is oriented with the initial orientation of the visual output 2464.

At step 2402, the user makes a gesture 2471, which in this illustration is a sweeping motion of his hand 2472. A motion detector disposed in the electronic device 2461, which may be an accelerometer, compass, gyroscope, or other device, senses the motion caused by this gesture 2471 and delivers a signal corresponding thereto to a control circuit. Upon receiving the user input, the control circuit alters the presentation orientation from the initial orientation to a second presentation orientation. In this illustration, the second presentation orientation is a predetermined rotation amount of 180 degrees, thus causing the visual output 2464 to "flip" upside down on the display 2463.

To preserve a common navigation control scheme, the initial disposition of the user interface component 2494 is retained. In this illustrative embodiment, the user interface component 2494 is retained in an initial disposition with a bearing fixed relative to the initial disposition's orientation in three-dimensional space 2400. Thus, despite the fact that the user's arm has rotated by 90 degrees, the user 2470 still has the user interface component 2494 facing him. Thus, if writing letters on the display 2463 with a stylus, the user could write them "right-side up" rather than having to write them in an odd orientation.

At step 2501, the user 2470 makes another gesture 2571 in the opposite direction. Upon detecting this gesture 2571, the control circuit reverts 2581 the presentation orientation of the visual output 2464 on the display 2463 to the initial orientation. The initial orientation is shown in step 2502. However, the initial disposition of the user interface component 2494 is retained with a bearing in three-dimensional space 2400 as shown in both steps 2501, 2502.

Figure 26:
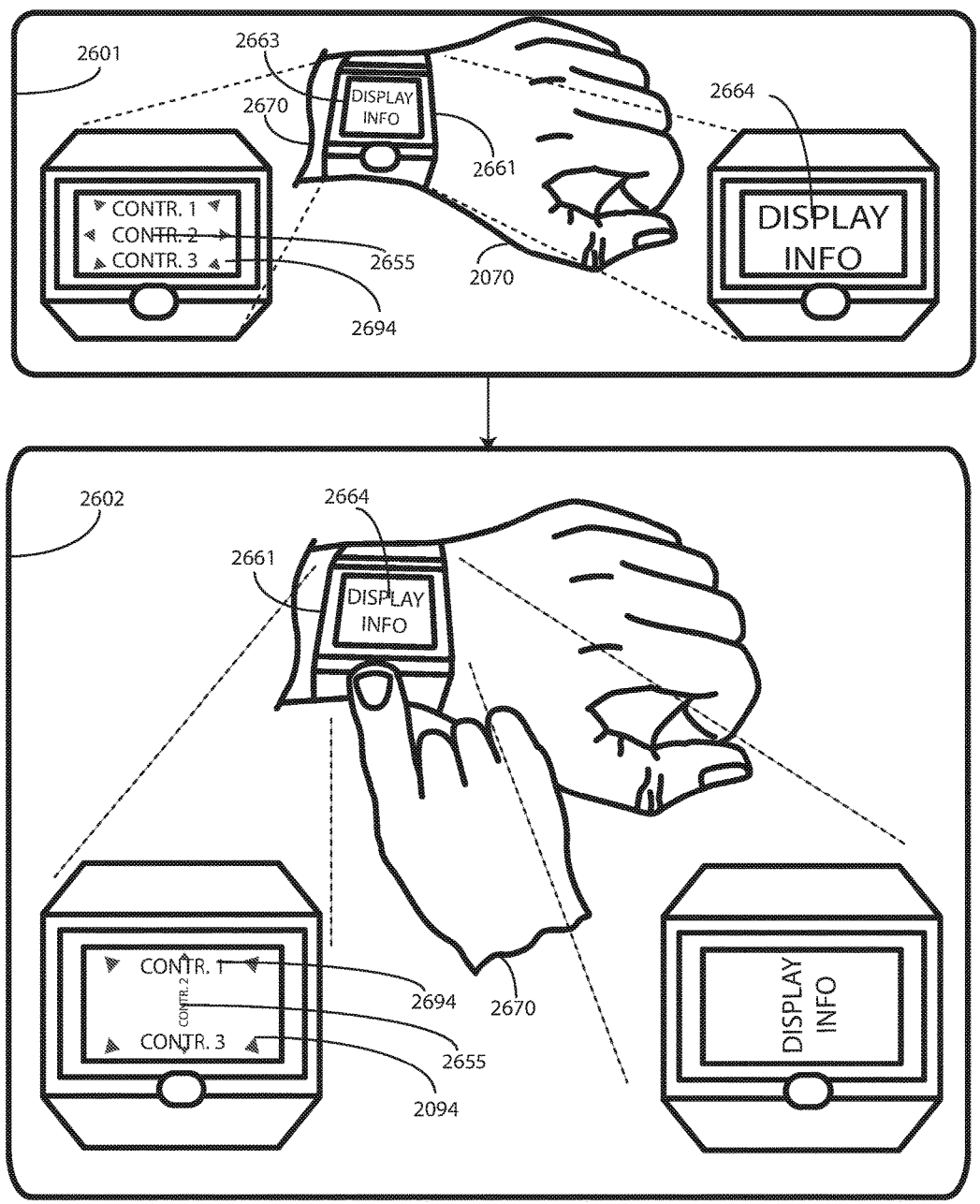
FIGS. 26-27 illustrate one method of altering the presentation orientation of visual output on an explanatory wearable electronic device in response to user input and altering a portion of an initial disposition of an associated user interface in accordance with one or more embodiments of the invention.
Figure 27:
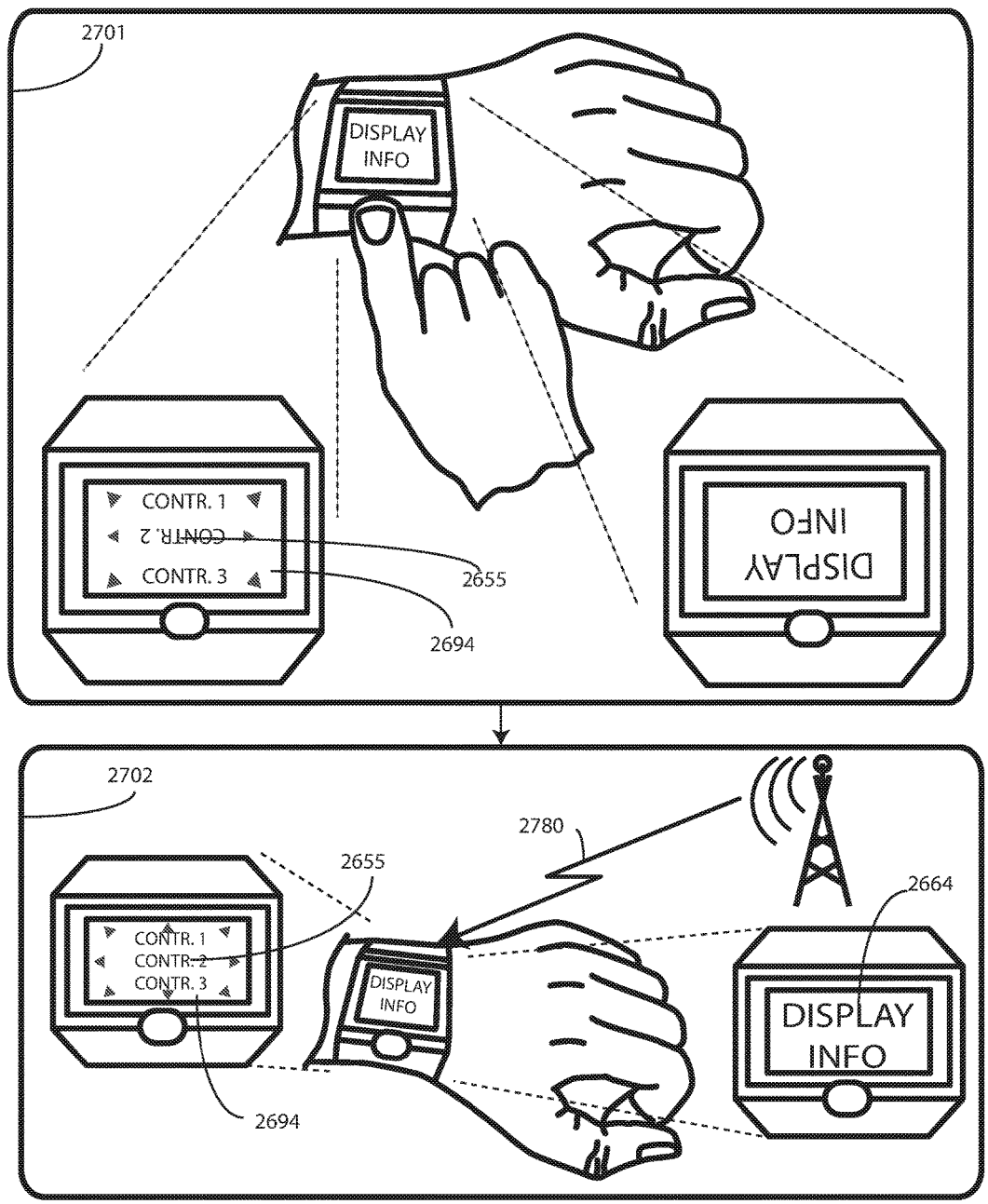

Turning now to FIGS. 26-27, illustrated therein is a method for altering a portion 2655 of the user interface component 2694 when altering the presentation orientation of visual output 2664 on the display 2663 of an electronic device 2661 in accordance with one or more embodiments of the invention. To this point, when user interface elements have been altered or retained, the examples have shown the entire user interface being altered or retained as a unit. However, it will be apparent to those of ordinary skill in the art having the benefit of this disclosure that portions of the user interface can be altered while other portions are retained. As noted in the discussion above, the retained portions can be retained in an orientation fixed relative to the electronic device 2661 or bearings fixed in three-dimensional space (2400). In the illustrative embodiment of FIGS. 26-27, a portion 2655 of the user interface component 2694 will be altered proportionally with the visual output 2664, while other portions are retained in an initial disposition fixed relative to both the electronic device 2661 and three-dimensional space due to the fact that the orientation of the electronic device 2661 remains unchanged.

Starting at step 2601, a user 2670 has a wearable electronic device 2661 strapped to his wrist. The display 2663 of the wearable electronic device 2661 presents visual output 2664, which in this case is a picture that the user 2670 wishes to show to a friend. The visual output 2664 is presented with presentation orientation that is an initial orientation. In this example, the bottom of the picture is towards the body of the user 2670.

The visual output 2664 also has associated therewith a user interface component 2694. As shown at step 2601, the initial disposition of the user interface component 2694 is oriented with the initial orientation of the visual output 2664.

At step 2602, the user 2670 delivers user input to the wearable electronic device 2661 by pressing a physical key disposed on the wearable electronic device 2661. In this illustrative embodiment, actuation of the physical key causes the control circuit to alter the presentation orientation by a predetermined rotation amount, which is 90 degrees in this example. A portion 2655 of the user interface component 2694 is altered proportionally with the presentation orientation of the visual output 2664. Another portion of the user interface component 2694 is retained in its initial disposition. The same happens again at step 2701, when the user actuates the physical key again, thus rotating both the portion 2655 of the user interface component 2694 and the presentation orientation by another 90 degrees, while retaining the remainder of the user interface component 2694 in its initial disposition.

At step 2702, a non-user event occurs. In this illustration, the non-user event is an incoming telephone call 2780. Upon detecting this non-user event, the control circuit reverts the presentation orientation of the visual output 2664 and the portion 2655 of the user interface component 2694 to the initial orientation.

With regards to this explanatory embodiment, portions of the user interface that remain in their initial disposition and portions that are reoriented can be different modes of a user interface. For example, a preferred voice input direction can remain in its initial disposition, while touch navigation inputs are reoriented with the presentation orientation. Alternatively gesture input can remain in its initial disposition while touch navigation input is reoriented with the presentation orientation.

Figure 28:
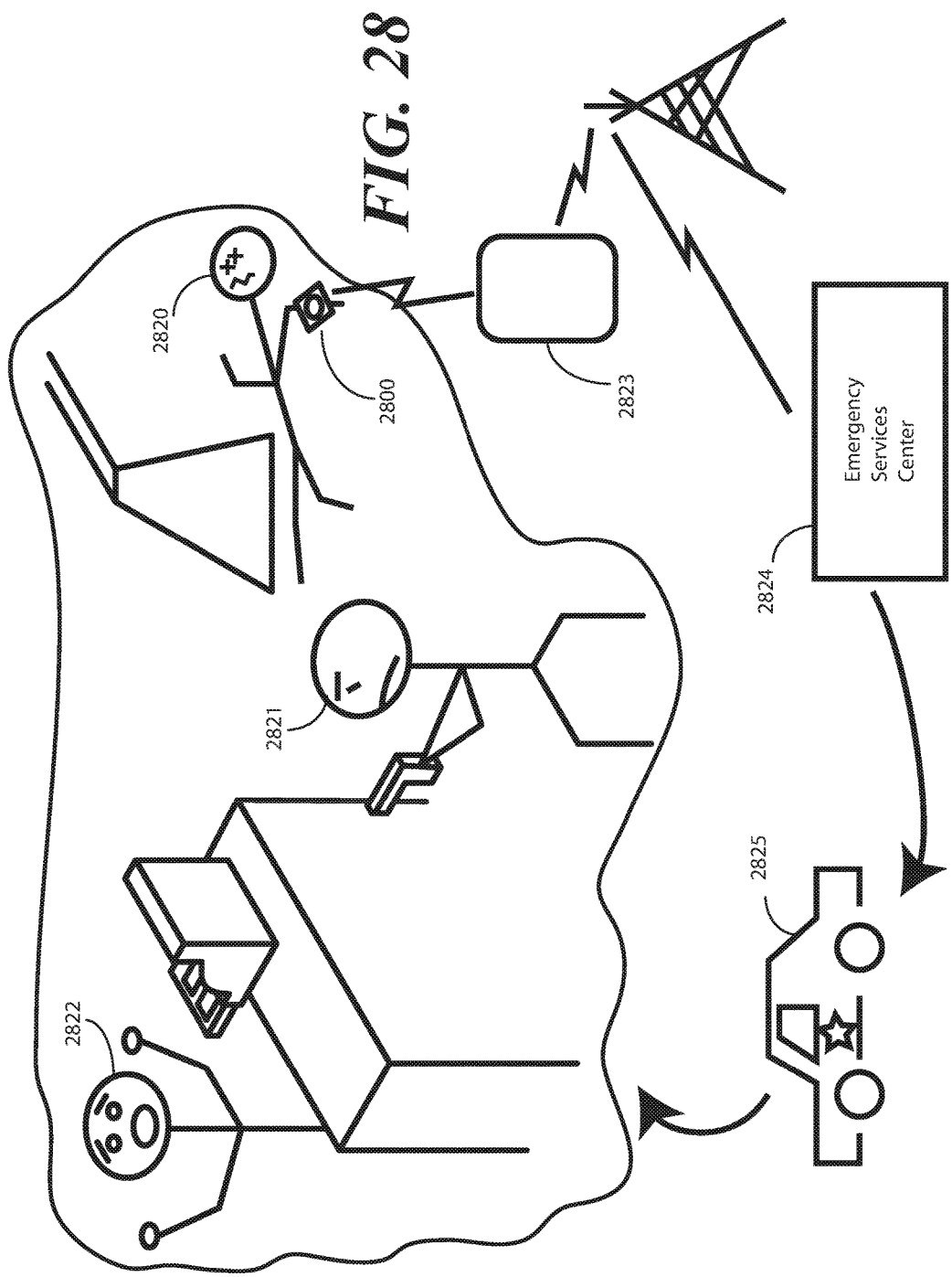
FIG. 28 illustrates one method of altering the presentation orientation of visual output on an explanatory wearable electronic device in response to wellness conditions sensed by wellness sensors in accordance with one or more embodiments of the invention.

Turning now to FIG. 28, illustrated therein is another use case demonstrating how wellness sensors disposed within an electronic device can be used not only to revert the presentation orientation, audio input, audio output, or combinations thereof, but also to perform other features as well.

As shown in FIG. 28, a store patron 2820 has passed out due to the stress of seeing a robbery in place. A robber 2821 is holding a clerk 2822 at gunpoint. The stress of this event has simply caused the store patron 2820 to faint. However, the store patron 2820 is fortunate enough to be wearing a wearable electronic device 2800 configured in accordance with one embodiment of the invention. This wearable electronic device 2800 is equipped with wellness sensors. The wellness sensors have sensed very abnormal vital signals from the store patron 2820. For example, his heart rate may have spiked through the roof only to fall upon fainting. Further, his temperature may have experienced variations as well. Perspiration may be present. More importantly, the wellness sensors are capable of detecting that the store patron 2820 has fallen and is now motionless after exhibiting the abnormal vital signs.

In the scenario of FIG. 28, the store patron 2820 cannot speak due to having fainted. However, the wearable electronic device 2800 is configured to transmit emergency alerts upon detecting that the store patron 2820 has experienced unusual physical conditions, has fallen, and is motionless. The wearable electronic device 2800 pulls location information from the global positioning sensor. The electronic device then sends an emergency communication message 2823 to the appropriate emergency services personnel through an emergency services call number, such as 911 or SOS. The emergency services call number will depend upon what regional authorities use as an appropriate emergency services call number. The emergency communication message 2823 is then sent to the emergency services center 2824. This transmission can be through any of a variety of methods, including short message services, multimedia message services, instant messaging, messaging over session interrupt protocol, and so forth. Emergency personnel 2825 can then be dispatched to render assistance.

Figure 29:
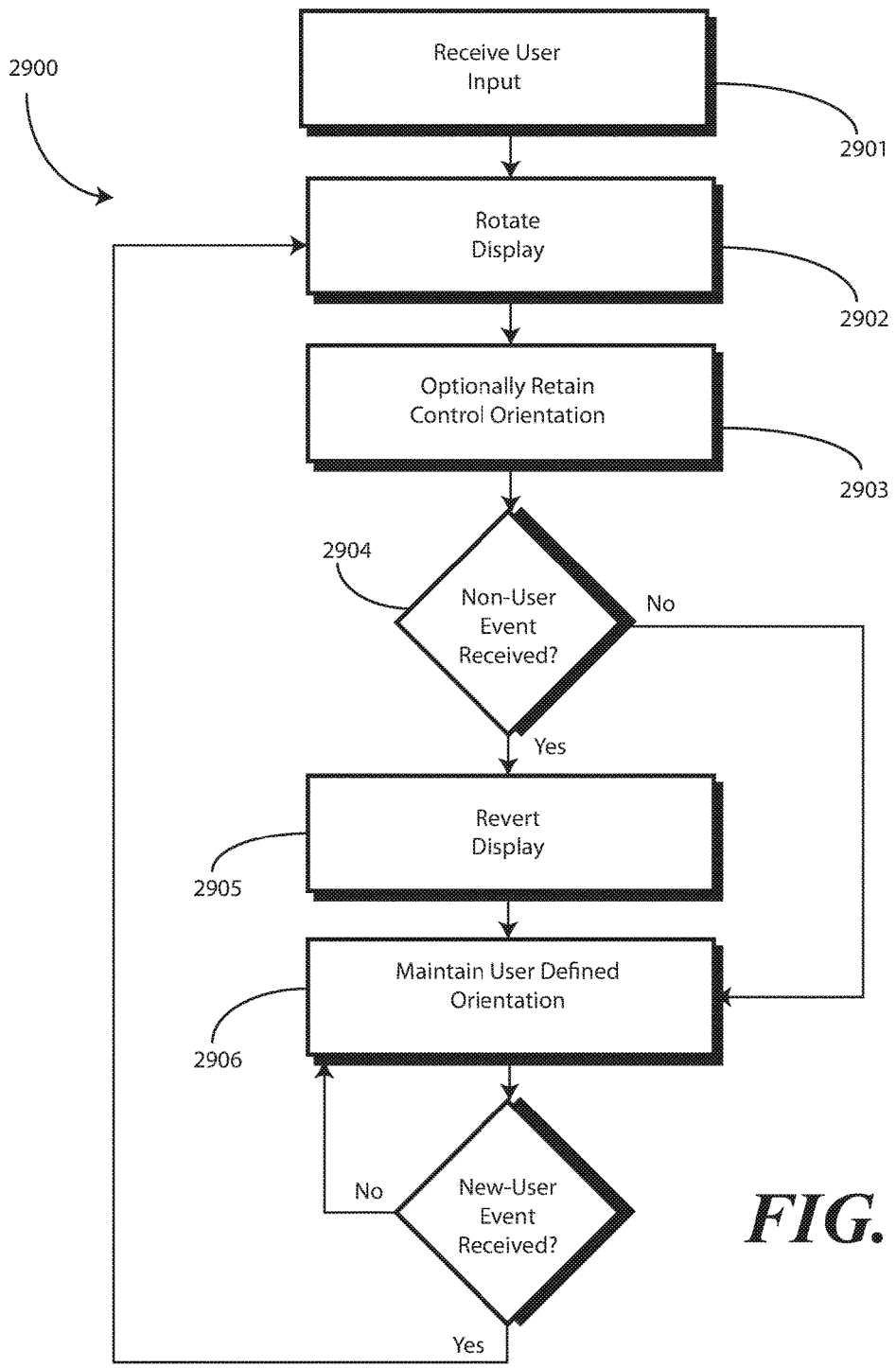
FIG. 29 illustrates a method of altering and reverting images and other visual output on a display in accordance with one or more embodiments of the invention.

Turning now to FIG. 29, illustrated therein is a method 2900 of orienting images in accordance with embodiments of the invention shown in flow-chart form. Most of the steps of FIG. 29 have been described in detail above, and as such, will be mentioned only briefly here.

At step 2901, the method 2900 receives user input. As noted above, the user input can comprise one of audio input, touch input on the display, actuation of an input control device operable with the control circuit, a sensed gesture, a light-sensed user action, an ultrasonic-sensed user action, or an infrared-sensed user action. Other examples of user input will be obvious to those of ordinary skill in the art having the benefit of this disclosure.

At step 2902, a presentation module operable with a display is configured to alter a presentation orientation of visual output from an initial orientation in response to receiving user input. This alteration can include rotating the visual output. Optionally, the alteration can include altering one of a color, a resolution, a scaling, or a magnification of the visual output, or combinations thereof. At step 2903, the presentation module can optionally maintain an initial disposition of a user input configuration associated with the visual output on a user interface.

At decision 2904, device events or non-user events are detected. Examples of these include an incoming telephone call, an incoming text message, an incoming multimedia message, a low battery warning, or a calendar alarm event. Device events can also include wellness factors of the user sensed by wellness detectors. When a device event or a non-user event occurs, the presentation module can revert the presentation orientation of the visual output on the display to an initial orientation at step 2905. Until the device event or non-user event occurs, the presentation module can retain the user-defined orientation at 2906 until additional user input requiring redirection of the visual output is received.

Figure 30:
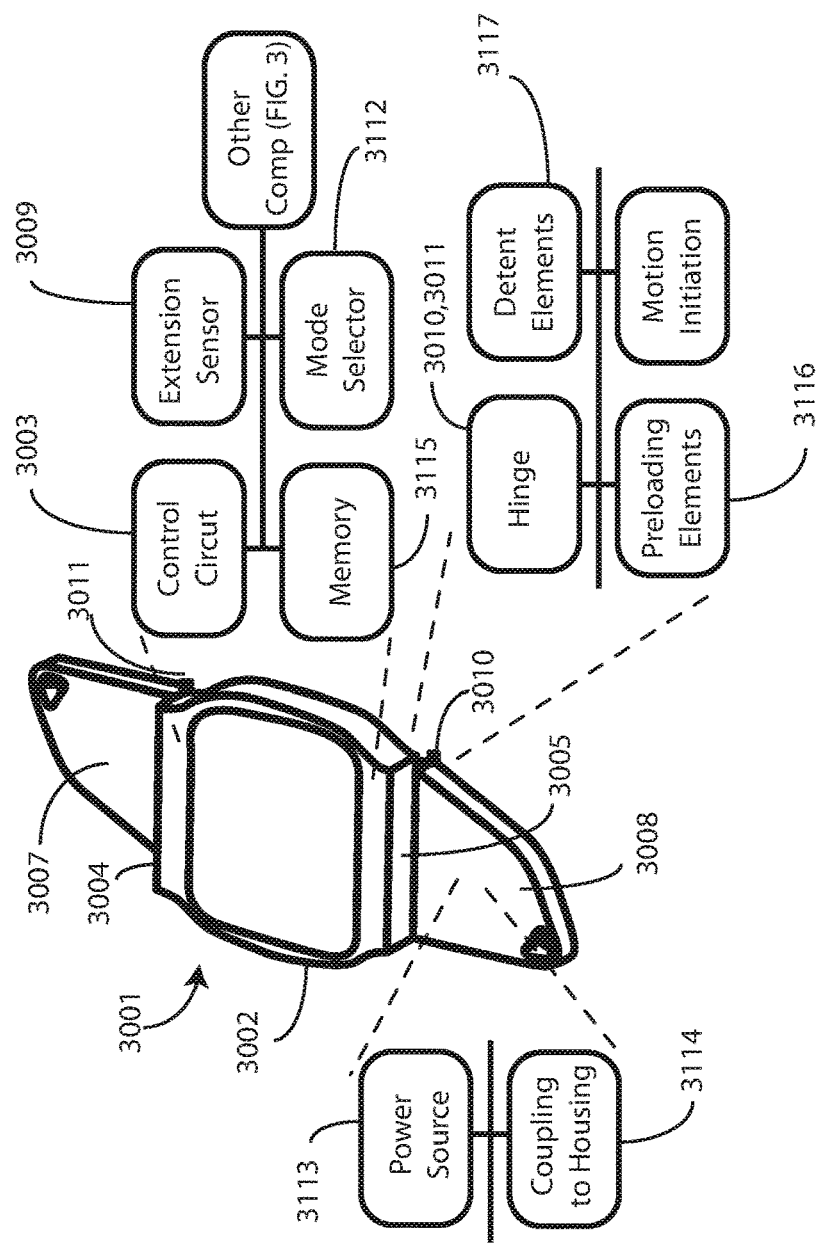
FIG. 30 illustrates a schematic block diagram of one explanatory electronic device configured in accordance with one or more embodiments of the invention.

Turning now to FIG. 30, illustrated therein is a detachable electronic module 3001 having a control circuit 3003 disposed within a central housing 3002 of the detachable electronic module 3001. The central housing 3002 is the portion of the detachable electronic module 3001 that is disposed between the first electronic module extension 3007 and the second electronic module extension 3008, which are hingedly coupled to a first side 3004 and a second side 3005 of the central housing 3002. The first electronic module extension 3007 and the second electronic module extension 3008 extending distally from the opposite first side 3004 and second side 3005 of the central housing 3002, and are configured to be selectively pivotable about the central housing 3002.

As shown in FIG. 30, each electronic module extension 3007, 3008 includes only a power source 3113 (and corresponding safety and/or charging components) and an electronic coupling structure 3114 through which energy can be delivered to and from the power source 3113. In one embodiment, the electronic coupling structure 3114 is integrated with the hinges 3010, 3011, For example, the hinges 3010, 3011 can comprise electrical contacts configured to couple to an external power source to the power sources 3113 disposed within the electronic module extensions 3007, 3008.

In one embodiment, the power source 3113 comprises a rechargeable battery. All other electronics associated with the operating modes of the detachable electronic module 3001, e.g., the control circuit 3003 and memory 3115, are disposed within the central housing 3002. The power source 3113 is thus configured to deliver energy to electronic components disposed only within the central housing 3002.

The hinges 3010, 3011 can include a variety of features. For example, in one embodiment the hinges 3010, 3011 are pre-loaded with a biasing element 3116 such as a spring. Pre-loading with a biased hinge can be used, for example, to retain the first electronic module extension 3007 and the second electronic module extension 3008 in one of the angularly displaced open position or the closed position.

In another embodiment, the hinges 3010, 3011 are detented with detenting elements 3117. For example, a detented hinge having a plurality of detent stops can be configured to hold one or both of the first electronic module extension 3007 or the second electronic module extension 3008 in one of a plurality of angularly displaced alignments relative to the central housing 3002.

The control circuit 3003 in this embodiment is operable to alter an operating mode of the detachable electronic module 3001 to one of a plurality of functional modes depending upon the angularly displaced orientation of the electronic module extensions 3007, 3008 relative to the central housing 3002. The operable modes can be any of the following: a desktop mode, a telephone mode, a wristwatch mode, health monitoring mode, a clock mode, a calendar mode, a gaming mode, an On-Star™ physical safety mode, an ON mode, an OFF mode, a security device mode, a baby monitor mode, a headset type mode, a scale function mode, or a media player mode. An example of a desktop mode may include features found in a desktop, palmtop, or tablet computer, such as a speaker phone, web browser, gaming applications, WiFi communication capabilities, and so forth. A telephone mode may include wide area network communication capabilities such that the detachable electronic module 3001 can function as a cellular phone. A wristwatch mode may include displaying the time, date, and calendar events. A clock mode may simply present the time on the display. A calendar mode may simply present calendar events on the display. A gaming mode may present gaming indicia and/or controls on the display. A media player mode may play music or videos on the display. A On-Star™ mode may monitor sudden gravitational force changes, such as a person falling. A security device mode may trigger audio monitoring and alerts. A scale mode my enable scale function when device is placed stationary flat on a tabletop. These modes are explanatory only, as others will be obvious to those of ordinary skill in the art having the benefit of this disclosure.

An extension detection sensor 3009 is configured to detect an angularly displaced location of one or both of the first electronic module extension 3007 or the second electronic module extension 3008. For example, in one embodiment the hinges 3010, 3011 are equipped with electrical sensors capable of determining a rotational amount of each hinge 3010, 3011. The extension detection sensor 3009 can then correlate the amount of rotation with an estimated angularly displaced orientation. In an alternate embodiment, where the hinges 3010, 3011 are detented, the extension sensor can detect with electrical switching in which détente a electronic module extension stop is resting, and thus determine the angularly displaced orientation.

Once the angularly displaced orientation of one or both of the first electronic module extension 3007 or the second electronic module extension 3008 is known, a mode selector 3112, operable with the control circuit 3003, can select one of the plurality of functional modes based upon the angular position detected by the extension detection sensor 3009. This will be illustrated in subsequent use cases.

The mode selector 3112 and extension detection sensor 3009 can be configured as executable instructions stored in the memory 3115. A flow chart of an illustrative method suitable for altering the operating modes of the detachable electronic module 3001 is shown in FIG. 31.

Figure 31:
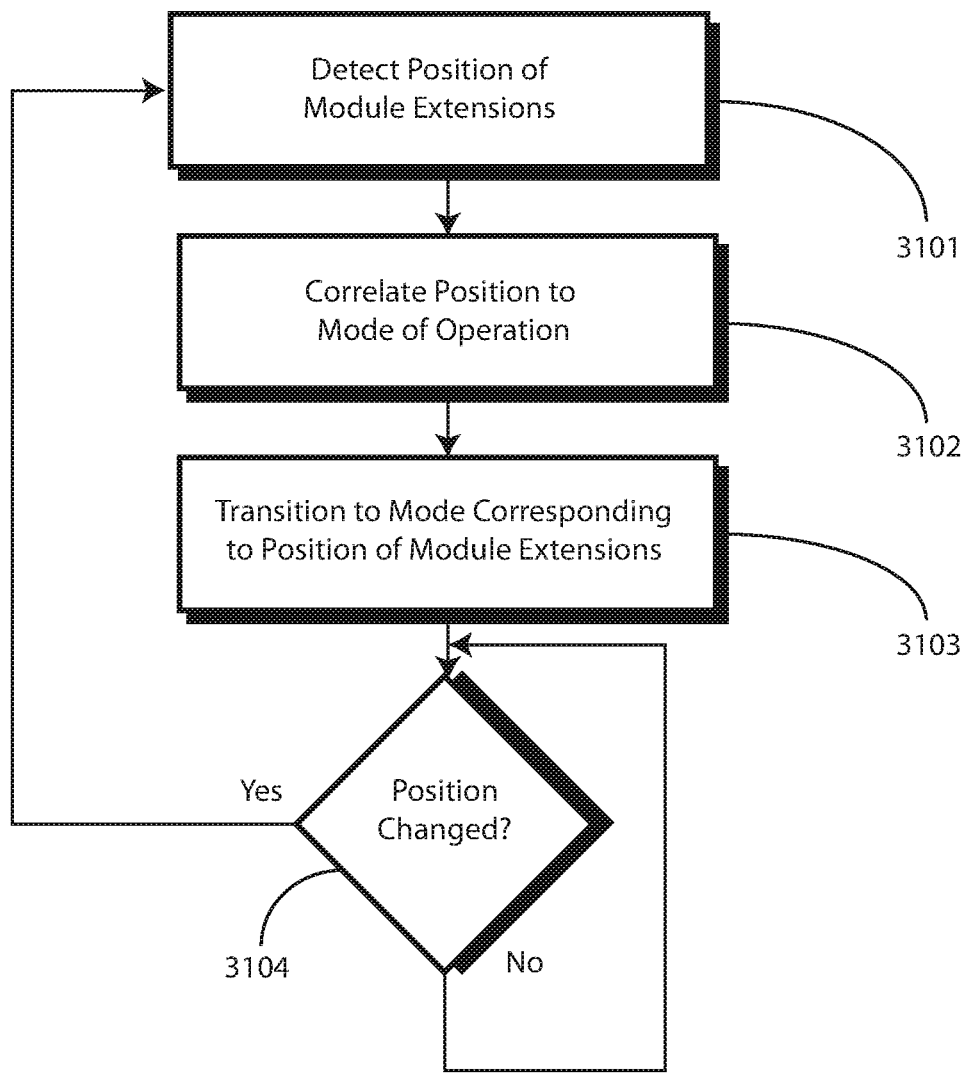
FIG. 31 illustrates one explanatory method of selecting an operational mode of an electronic module configured in accordance with one or more embodiments of the invention.

Turning now to FIG. 31, the method 3100 begins at step 3100 where the extension detection sensor (3009) detects an angular position of one or more electronic module extensions (3007, 3008) that pivotally coupled to a central housing (3002) and configured for selective movement between a plurality of angular displaced positions relative to the central housing (3002). At step 3102, the control circuit (3003) or extension detection sensor (3009) can correlate a detected angular position with a functional mode of the detachable electronic module (3001). At step 3103, the control circuit (3003) can transition the operational mode of the detachable electronic module (3001) to a correlated functional mode in response to the detecting the angular position of the electronic module extensions (3007, 3008).

The extension detection sensor (3009) can continue to monitor the angular positions of the electronic module extensions (3007, 3008). Where there is a change, detected at decision 3104, the method 3100 can repeat, resulting in the control circuit (3003) again transitioning the operational mode of the detachable electronic module (3001) to another correlated functional mode in response to the detecting the angular position of the electronic module extensions (3007, 3008). Turning now to FIGS. 32-44, illustrated therein will be several use cases demonstrating how the operational mode of various detachable electronic modules can be altered by changing the angularly displaced orientations of the electronic module extensions relative to the central housing.

Figure 32:
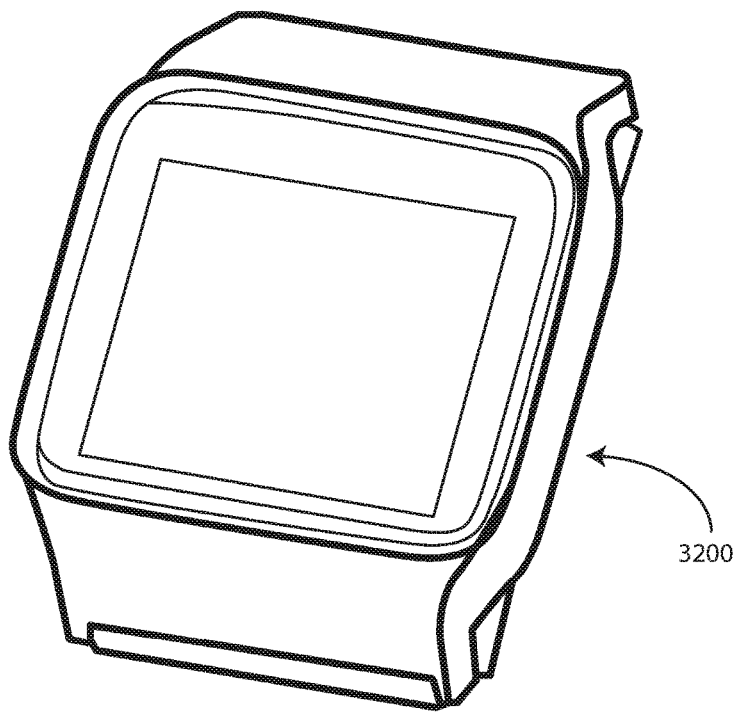
FIGS. 32-33 illustrates a detachable electronic module having planar electronic module extensions and operating in one of a plurality of predefined modes as a function of the angularly displaced location of its electronic module extensions in accordance with embodiments of the invention.
Figure 33:
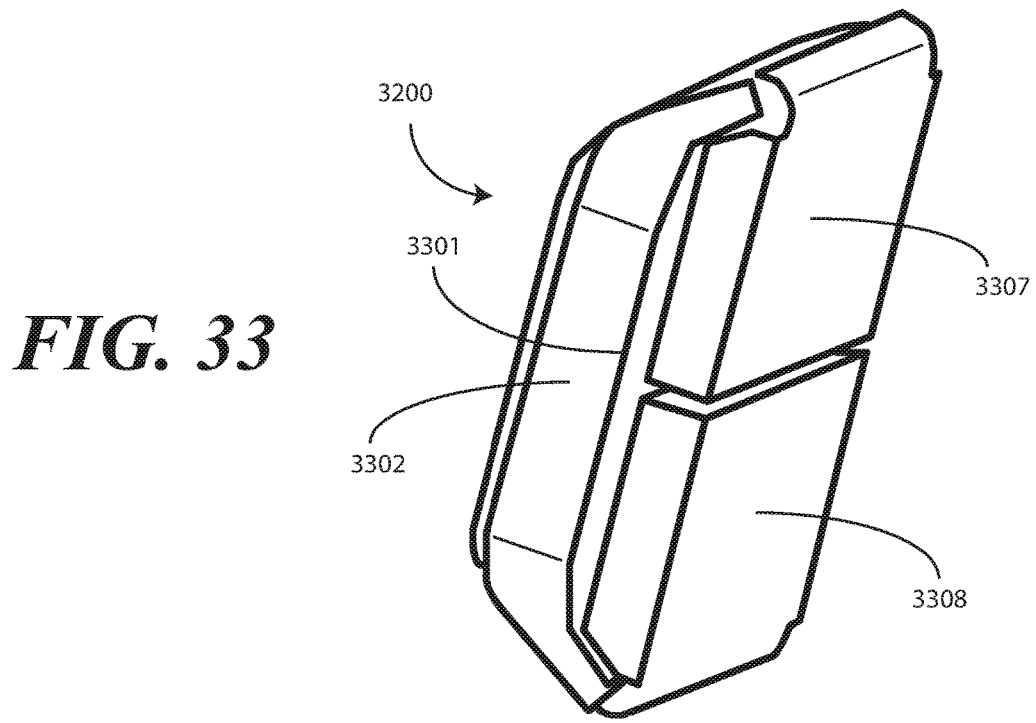

Beginning with FIGS. 32-33, illustrated therein is a detachable electronic module 3200 having substantially planar electronic module extensions 3307, 3308. In FIGS. 32-33, the electronic module extensions 3307, 3308 have been rotated to a closed position. In the closed position, the electronic module extensions 3307, 3308 are disposed against a major face 3301 disposed on the rear side of the central housing 3302.

As previously described, the control circuit disposed within the central housing 3302 can be configured to alter the operating mode of the detachable electronic module 3200 to one of a plurality of functional modes as a function of the position of the electronic module extensions 3307, 3308. In the embodiment of FIGS. 32-33, the electronic module extensions 3307, 3308 are substantially planar. By pivoting the electronic module extensions 3307, 3308 to the closed position, a user may want to place the detachable electronic module 3300 in a desktop mode, speakerphone mode, or gaming mode. In one embodiment, the control circuit is user programmable to function in a predefined, user-selected mode when the electronic module extensions 3307, 3308 are in the closed position.

Figure 34:
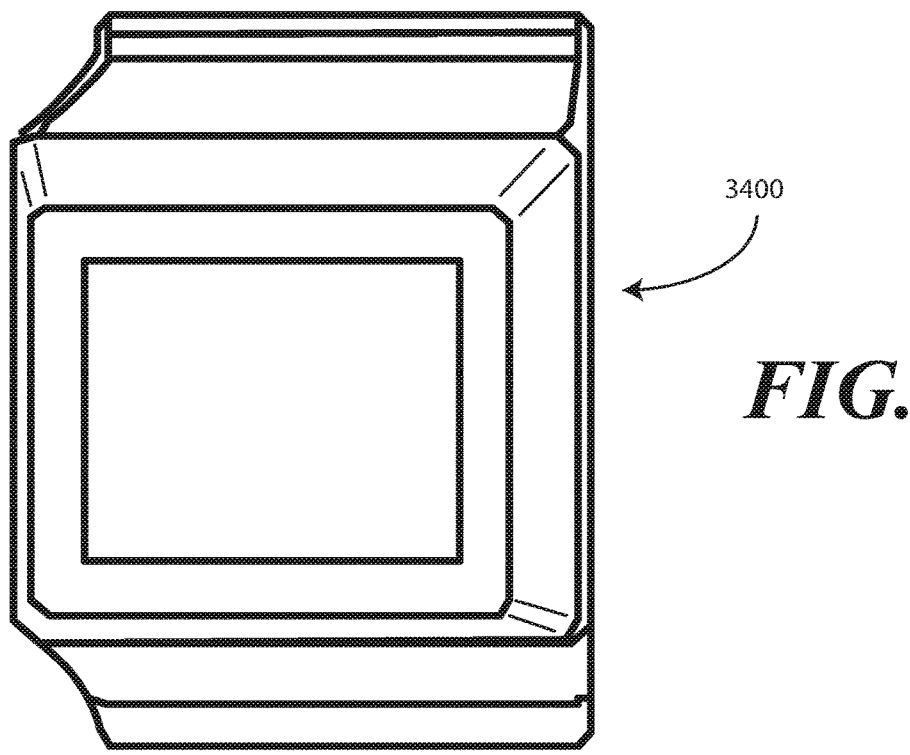
FIGS. 34-35 illustrates a detachable electronic module having non-planar electronic module extensions and operating in one of a plurality of predefined modes as a function of the angularly displaced location of its electronic module extensions in accordance with embodiments of the invention.
Figure 35:
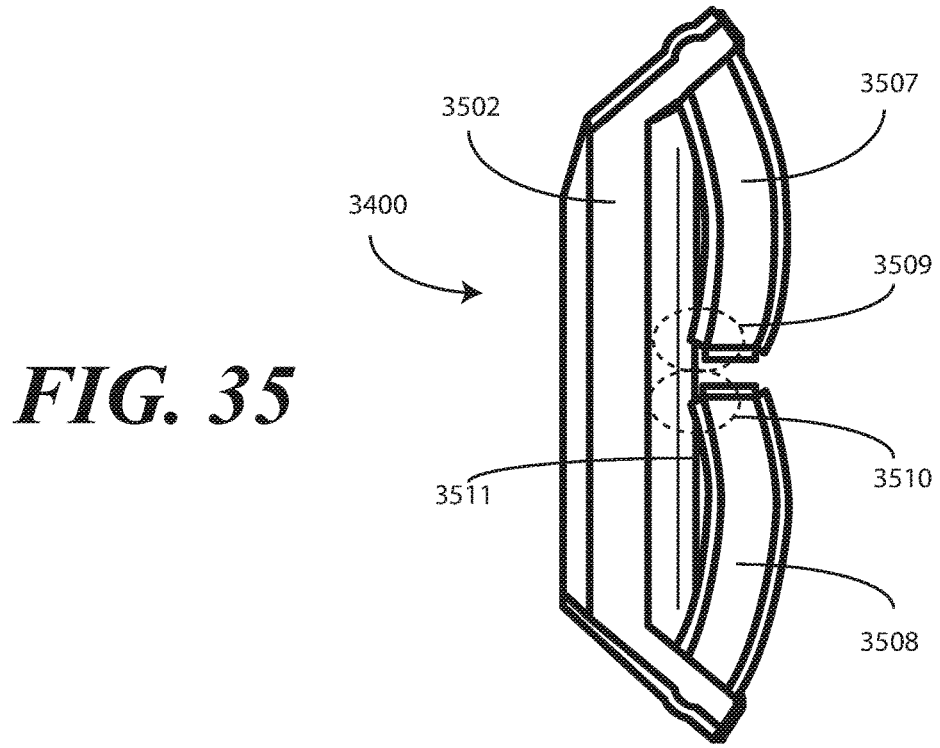

FIGS. 34-35 illustrate a similar detachable electronic module 3400 having electronic module extensions 3507, 3508 in the closed position as well. In FIGS. 34-35, the electronic module extensions 3507, 3508 are non-planar and have a curved cross section. Accordingly, when the electronic module extensions 3507, 3508 are in the closed position, only a portion 3509, 3510 of the electronic module extensions 3507, 3508 touches the rear face 3511 of the housing 3502. One advantage of non-planar electronic module extensions 3507, 3508 is that objects can be disposed within the voids between the electronic module extensions 3507, 3508 and the rear face 3511. For example, in the closed position shown in FIGS. 34-35, the electronic module extensions 3507, 3508 can be used as "clips" to hold the detachable electronic module 3400 onto a purse strap, a backpack strap, and so forth.

In the illustrative embodiment of FIGS. 34-35, since the control circuit is configured to select the one of the plurality of functional modes based upon the angular position of the electronic module extensions 3507, 3508. Thus, the detachable electronic module 3400 of FIGS. 34-35 is operating in a first operating mode.

Figure 36:
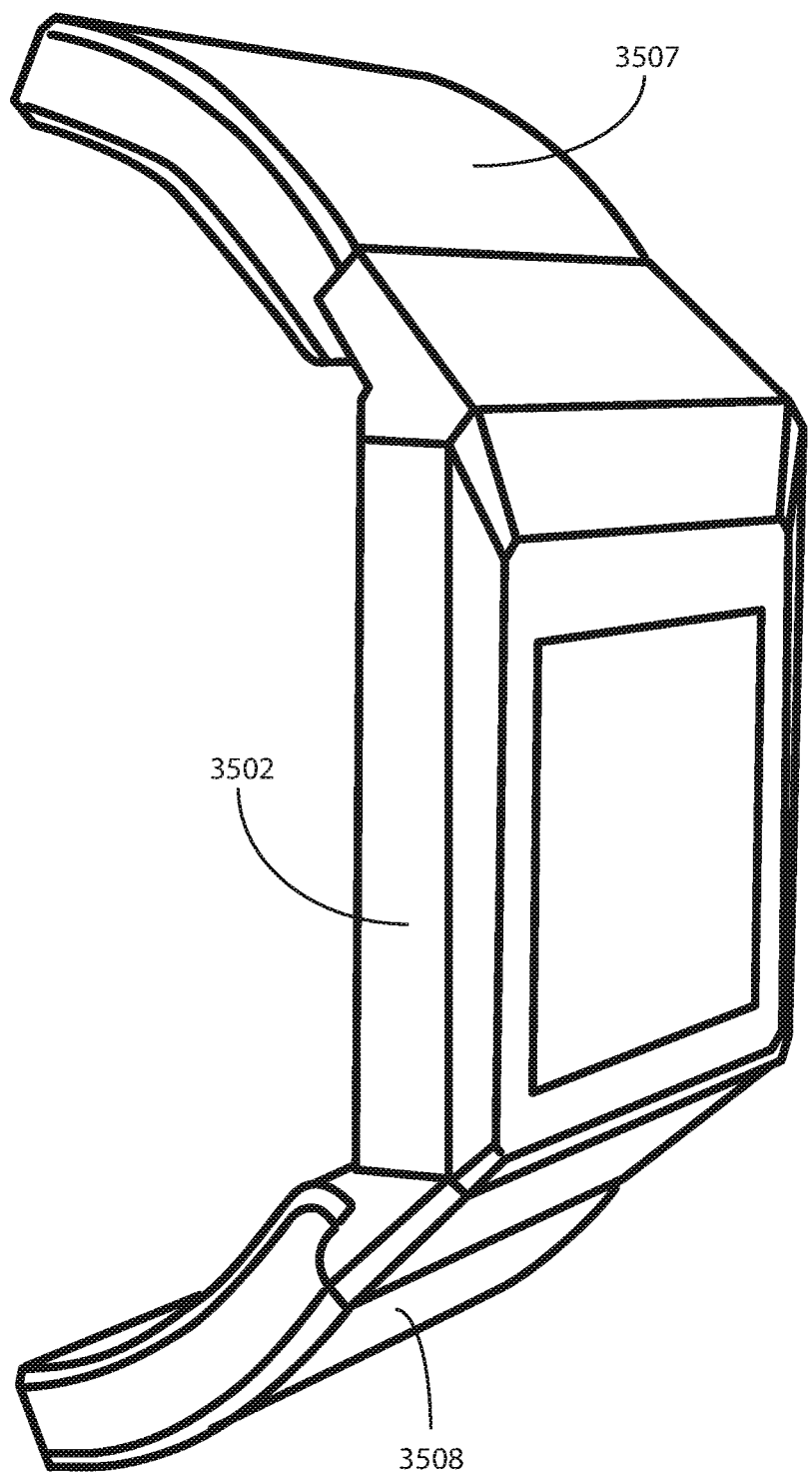
FIG. 36 illustrates the detachable electronic module of FIGS. 34 and 35 operating in another of a plurality of predefined modes as a function of the angularly displaced location of its electronic module extensions in accordance with embodiments of the invention.

By contrast, in FIG. 36, the electronic module extensions 3507, 3508 have been pivoted about the central housing 3502 to an angularly displaced open position extending distally outward from the housing 3502. Accordingly, the control circuit changes the operational mode to another mode that is different from that occurring in FIGS. 34-35. Illustrating by example, the operational mode in FIGS. 34-35 may have been a clock mode, while the operational mode in FIG. 36 is a health monitoring mode, and so forth.

Figure 37:
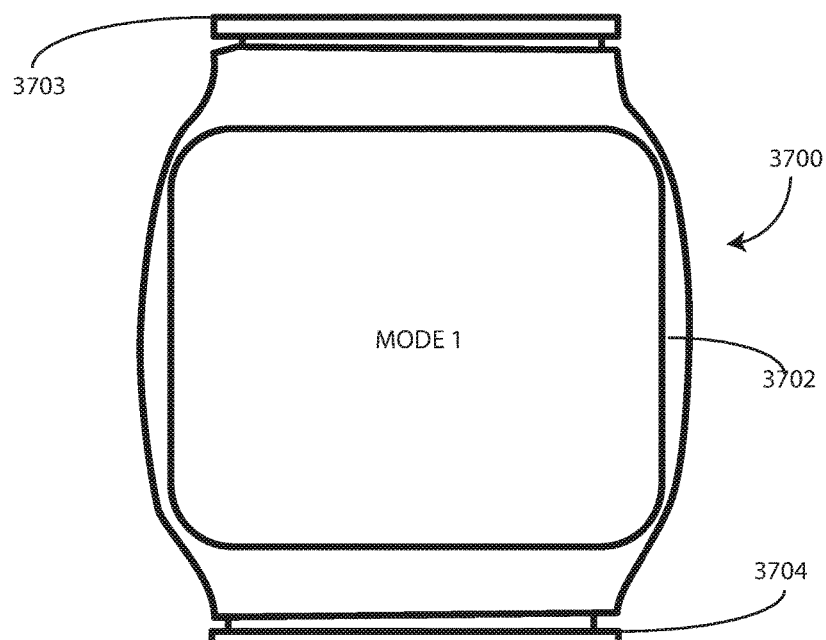
FIGS. 37 and 38 illustrate another detachable electronic module having planar electronic module extensions and operating in one of a plurality of predefined modes as a function of the angularly displaced location of its electronic module extensions in accordance with embodiments of the invention.
Figure 38:
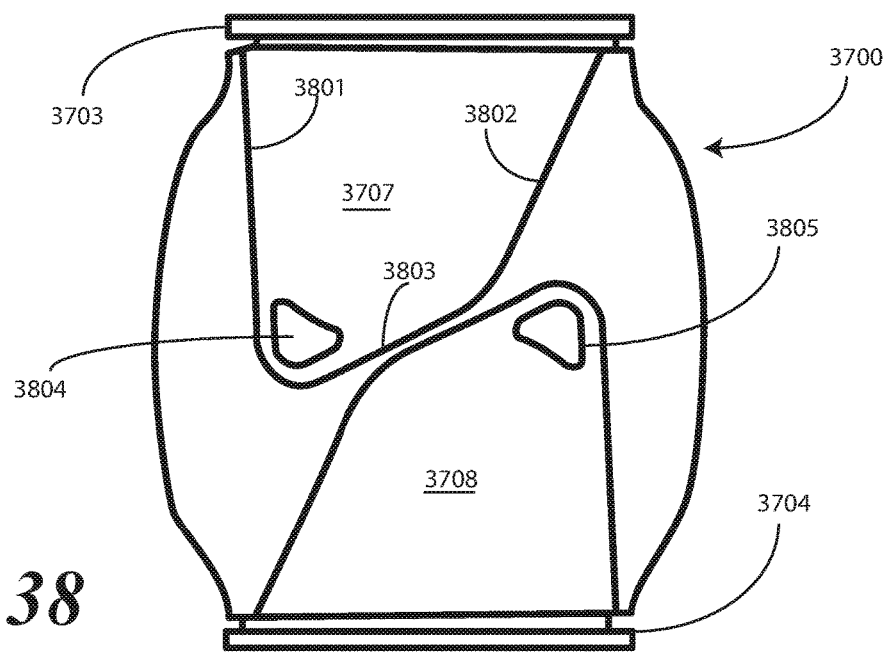
Figure 39:
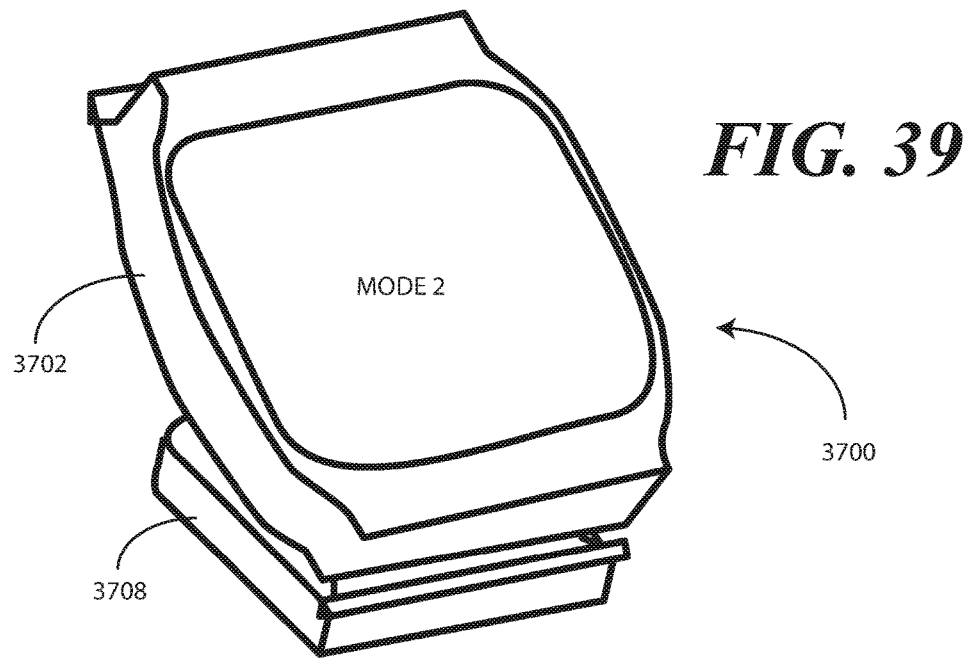
FIGS. 39-40 illustrate the detachable electronic module of FIGS. 37 and 38 operating in another of a plurality of predefined modes as a function of the angularly displaced location of its electronic module extensions in accordance with embodiments of the invention.
Figure 40:
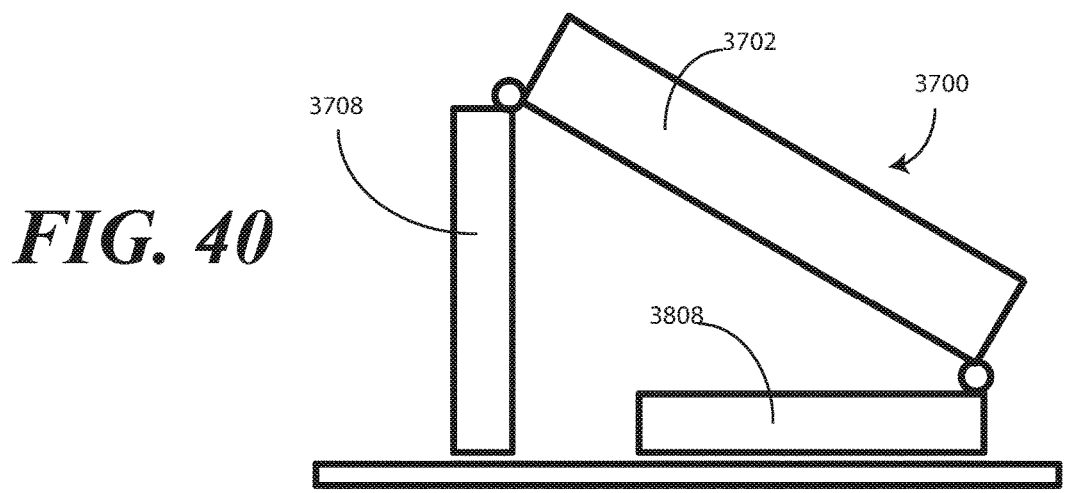
Figure 41:
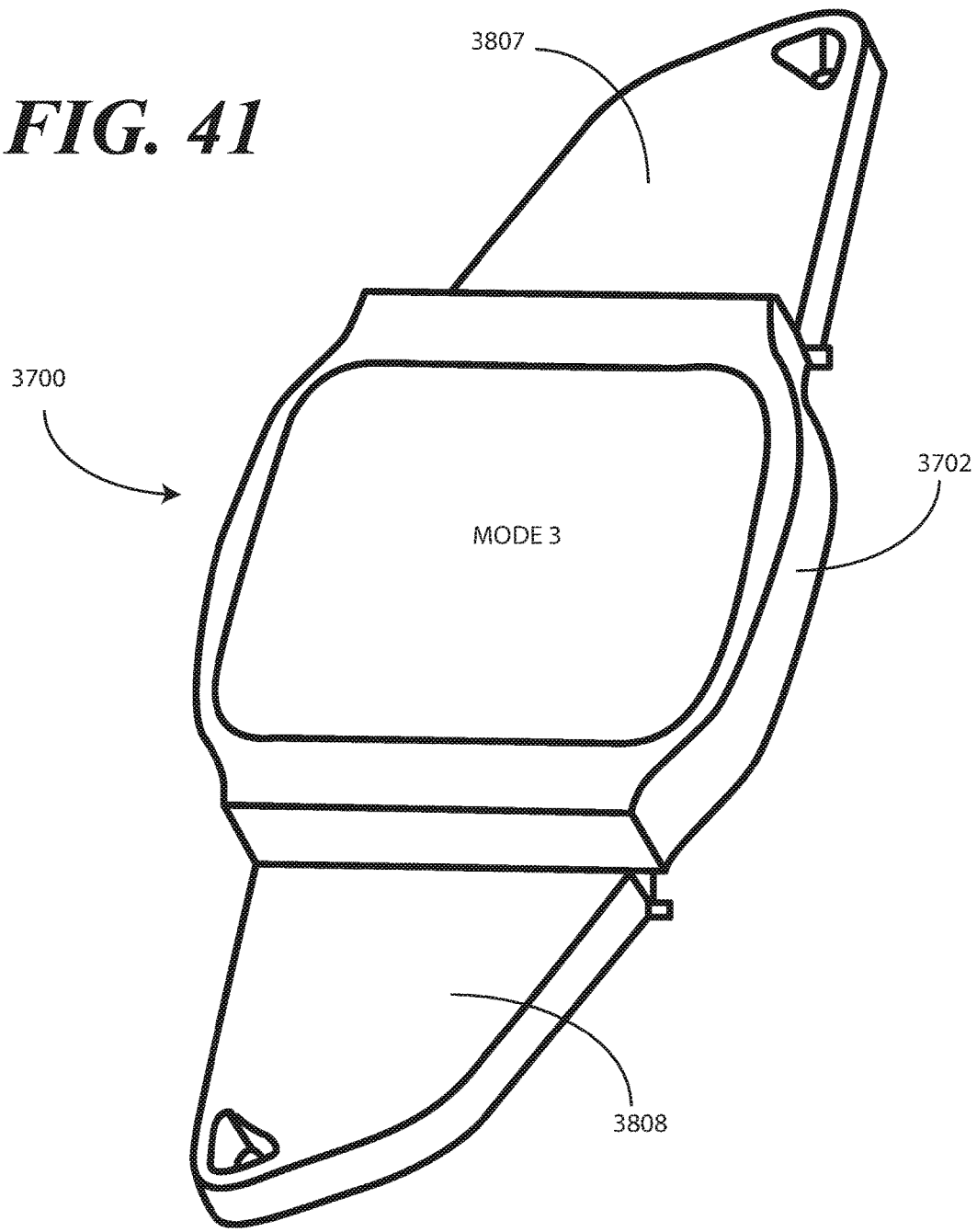
FIG. 41 illustrates the detachable electronic module of FIGS. 37 and 38 operating in yet another of a plurality of predefined modes as a function of the angularly displaced location of its electronic module extensions in accordance with embodiments of the invention.
Figure 42:
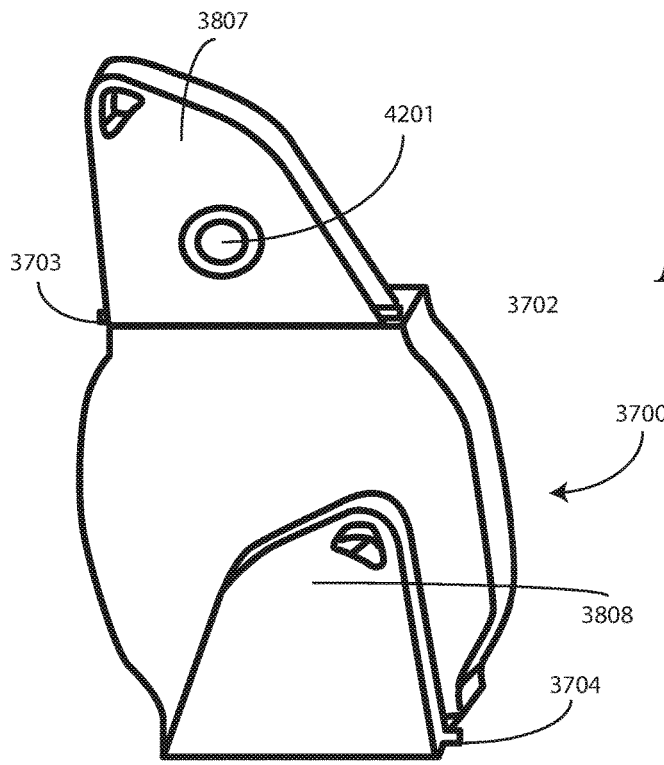
FIGS. 42-43 illustrate the detachable electronic module of FIGS. 37 and 38 operating in still yet another of a plurality of predefined modes as a function of the angularly displaced location of its electronic module extensions in accordance with embodiments of the invention.
Figure 43:
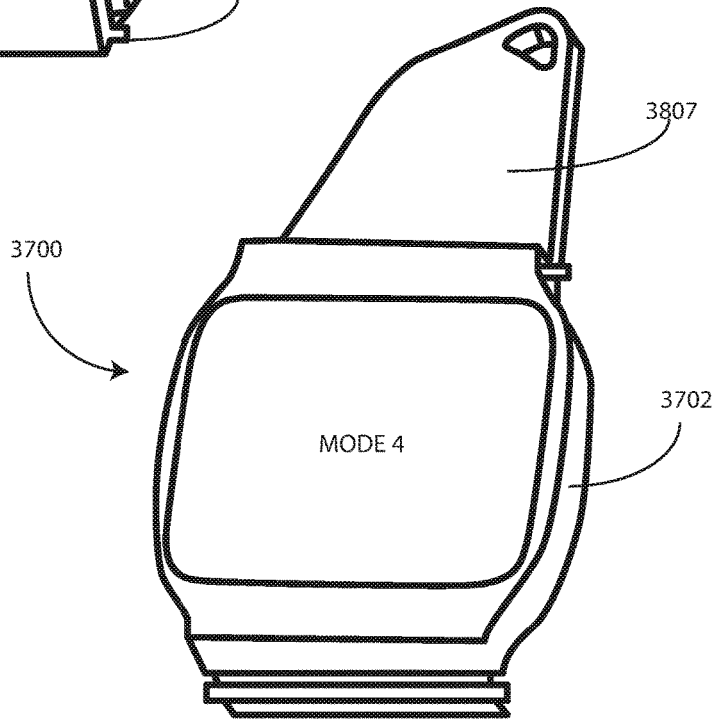

Turning to FIGS. 37-43, illustrated therein is another detachable electronic module 3700 configured in accordance with one or more embodiments of the invention. In FIGS. 37-43, three different operational modes are shown. Each operational mode is a function of the radial alignment of the electronic module extensions 3807, 3808 relative to the central housing 3702 of the detachable electronic module 3700. Each operating mode is selected from a plurality of predetermined operating modes of which the detachable electronic module 370 is capable of executing. A first mode is shown in FIGS. 37-38, while a second is shown in FIGS. 39-40. A third mode is shown in FIG. 41, while a fourth mode is shown in FIGS. 42-43. FIGS. 42-43 also depict how external electrical contacts 4201 can be hidden and revealed, or protected and exposed, as a function of the angularly displaced orientation of the electronic module extensions 3807, 3808.

In FIGS. 37-38, the electronic module extensions 3807, 3808 are in the closed position, with each electronic module extensions 3807, 3808 being folded completely about its respective hinge device 3703, 3704 to a displaced location against the back of the central housing 3702. The control circuit disposed within the central housing 3702 detects this and configures the detachable electronic module 3700 to operate in a first operational mode. The first operational mode may comprise a multimedia player mode where a video is presented on the display.

By contrast, in FIGS. 39-40, each electronic module extension 3807, 3808 is placed in a partially open angular displacement relative to the central housing 3702. Accordingly, the control circuit disposed within the central housing 3702 detects this and configures the detachable electronic module 3700 to operate in a second operational mode. The second operational mode may comprise a clock mode where the time of day is presented on the display to simulate a desk clock appearance.

FIG. 41 illustrates the electronic module extensions 3807, 3808 being in the open position. Accordingly, the control circuit disposed within the central housing 3702 detects this and configures the detachable electronic module 3700 to operate in a third operational mode. The third operational mode may comprise a health monitoring mode because the electronic module extensions 3807, 3808 are open and can be coupled to a strap for wearing on a wrist. When a strap that is selectively detachable from the detachable electronic module 3700 is attached, in one embodiment the control circuit actuates the health monitoring mode. In one embodiment, the control circuit is configured to convert the operating mode to modes other than the health monitoring mode when one or both of the first electronic module extension 3807 and the second electronic module extension 3808 is in the closed position, as shown in FIGS. 37-38.

FIGS. 42-43 illustrate a first electronic module extension 3807 being in the open position, while the second electronic module extension 3808 is in the closed position. Accordingly, the control circuit disposed within the central housing 3702 detects this and configures the detachable electronic module 3700 to operate in a fourth operational mode. The fourth operational mode may comprise a clock mode where the time of day is presented on the display to simulate a desk clock appearance.

The electronic module extensions 3807, 3808 of FIGS. 37-42 are configured with a different form factor as well. The form factor of FIGS. 37-42 includes both aesthetic elements and functional benefits. As shown in FIG. 38, the electronic module extensions 3807, 3808 are configured with asymmetric geometries such that they nest when placed in the closed position. This asymmetric contour having two side elements 3801, 3802 and a non-orthogonal, inclined third surface 3803 offer a unique aesthetic appearance.

At the same time, the electronic module extensions 3807, 3808 also have functional elements that are different from previously disclosed embodiments. For example, each electronic module extension 3807, 3808 has an aperture 3804, 3805 that can be used for attaching the detachable electronic module 3700 to various devices, including shirts, jackets, purses, backpacks, and the like.

FIGS. 42-43 illustrate another feature that the foldable electronic module extensions 3807, 3808 offer. As shown in FIG. 42, the bottom side of the electronic module extensions 3807, 3808 includes an externally exposed electrical contact 4201. While in on embodiment external charging contacts are disposed at the hinge devices 3703, 3704, in some applications it can be advantageous to place the charging contacts on major faces of the electronic module extensions 3807, 3808. Such an embodiment is shown in FIG. 42.

Where there is one or more externally exposed electrical contact 4201 on a major face of the electronic module extensions 3807, 3808, closing the electronic module extensions 3807, 3808 covers and protects the externally exposed electrical contact 4201. Said differently, the externally exposed electrical contact 4201 his hidden when the one or both of the first electronic module extension 3807 or the second electronic module extension 3808 is in the closed position, but is revealed when the electronic module extensions 3807, 3808 are in the open position.

Figure 44:
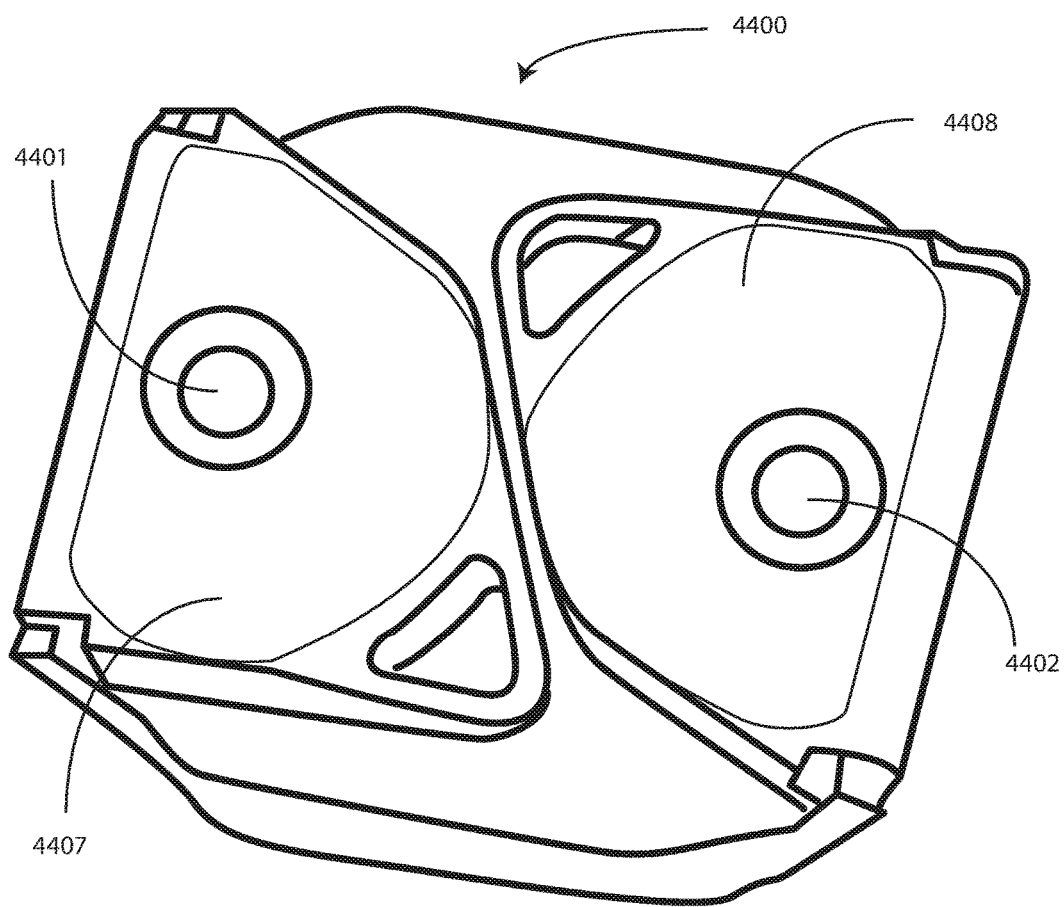
FIG. 44 illustrates a detachable electronic module having exposed electrical contacts on the electronic module extensions, where those contact can be hidden and revealed from a front view of the detachable electronic module based upon the position of the electronic module extensions.

FIG. 44 shows an alternate detachable electronic module 4400 having externally exposed electrical contacts 4401, 4402 disposed on the electronic module extensions 4407, 4408. In the embodiment of FIG. 4, the externally exposed electrical contacts 4401, 4402 are disposed on outer major faces of the electronic module extensions 4407, 4408. Accordingly, when the electronic module extensions 4407, 4408 are in the closed position, the externally exposed electrical contacts 4401, 4402 are concealed from view with reference to a viewer looking at the front of the detachable electronic module 4400. At the same time, the externally exposed electrical contacts 4401, 4402 are still exposed. This configuration allows the externally exposed electrical contacts 4401, 4402 to be rotated out of sight, while still being accessible. Accordingly, the detachable electronic module 4400 can be coupled to an external power source, e.g., placed in a charger or other device, while the electronic module extensions 4407, 4408 are in the closed position.

Figure 45:
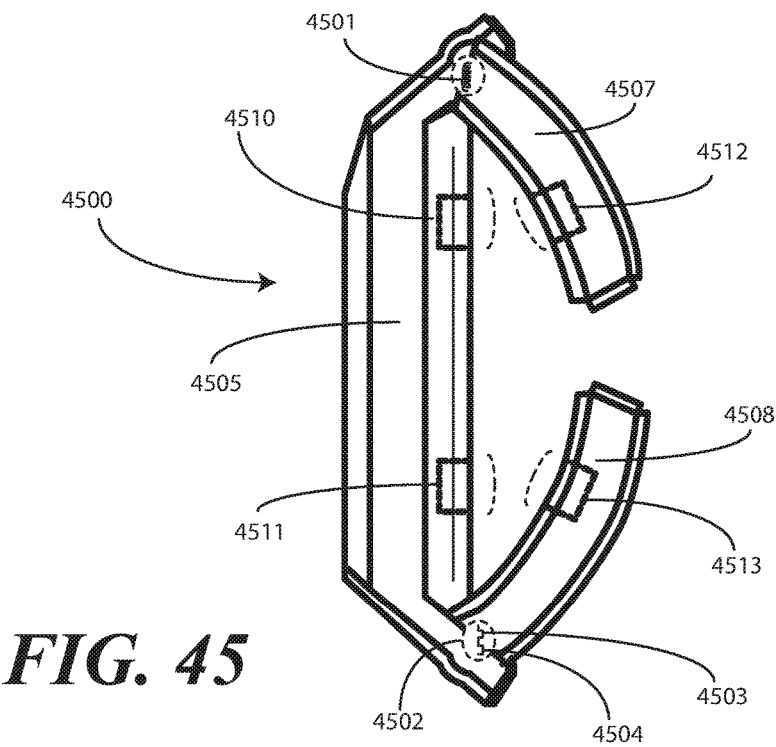
FIG. 45 illustrates one explanatory embodiment of a detachable electronic device having optional mechanical features configured in accordance with one or more embodiments of the invention.

FIG. 45 illustrates additional mechanical features that can be incorporated into a detachable electronic module 4500 configured in accordance with one or more embodiments of the invention. As mentioned above, in one embodiment the first electronic module extension 4507 and the second electronic module extension 4508 are coupled to the housing with a biased hinge 4501 configured to bias the first electronic module extension 4507 and/or the second electronic module extension 4508 towards one of the angularly displaced open position or the closed position. Such a biased hinge 4501 is shown in FIG. 45. Specifically, the biased hinge 4501 has a spring, which serves as a tensioning element that is configured to bias the first electronic module extension 4507 and/or the second electronic module extension 4508 towards one of the angularly displaced open position or the closed position.

As also described above, in one embodiment one or both of the first electronic module extension 4507 or the second electronic module extension 4508 is coupled to the housing by a detented hinge 4502 comprising a plurality of detent stops 4503, 4504 configured to hold the one or both of the first electronic module extension 4507 or the second electronic module extension 4508 in one of a plurality of angularly displaced alignments relative to the housing 4505. The detented hinge 4502 is illustrated in FIG. 45.

In one or more embodiments, the detachable electronic module 4500 includes retention devices 4510, 4511, 4512, 4513 configured to retain one or both of the first electronic module extension 4507 or the second electronic module extension 4508 in the closed position. The retention devices 4510, 4511, 4512, 4513 can be disposed in one or more of the housing 4505, the first electronic module extension 4507, or the second electronic module extension 4508. In the illustrative embodiment of FIG. 45, the retention devices 4510, 4511, 4512, 4513 comprise magnets, and are disposed in the electronic module extensions 4507, 4508 and the housing 4505. Other suitable retention devices suitable for use with embodiments of the invention include snaps, shaped detents, spring latches, and so forth.

Figure 46:
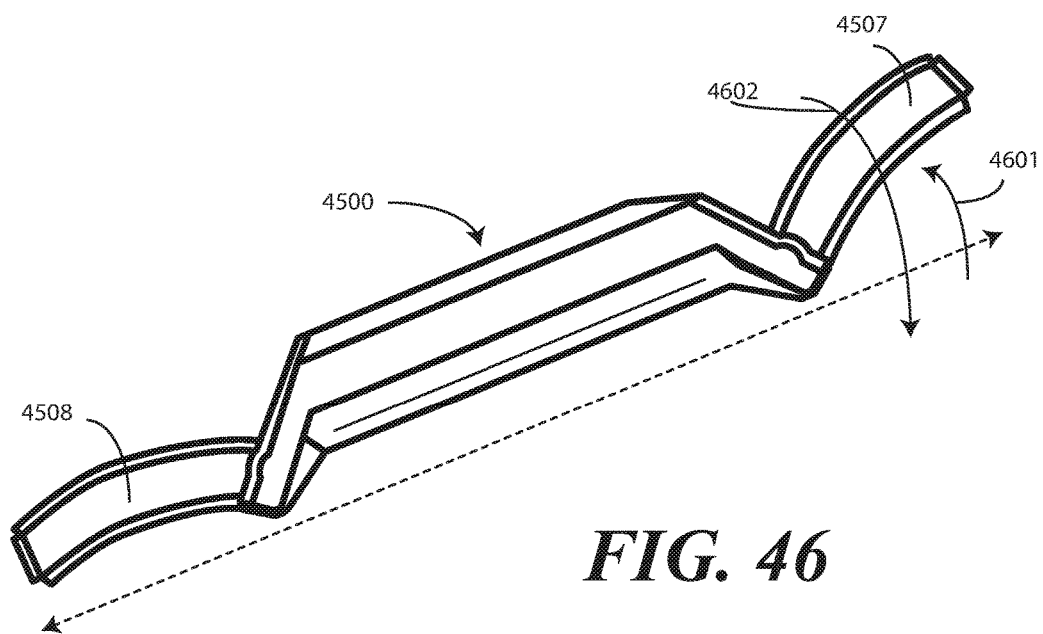
FIG. 46 illustrates a hyper-extended detachable module extension state suitable for detaching an electronic device module from, for example, an active strap in accordance with one or more embodiments of the invention.

As discussed above, the detachable electronic module 4500, in one embodiment, can be selectively coupled to a strap. The strap can be active or passive. It is contemplated that a user will want to attach or detach the detachable electronic module 4500 from the strap while the strap is on the wrist, which means that the attachment or detachment will occur with only one hand. To accomplish this, as shown in FIG. 46, in one embodiment the electronic module extensions 4507, 4508 are configured to "hyperextend" 4601 to facilitate detachment from a strap. Hyperextension is the angular displacement of the electronic module extensions 4507, 4508 past the open position, as shown in FIG. 46. In one embodiment, the detachable electronic module 4500 configured for hyperextension is equipped with biased hinges such that the hyperextension is opposed by a tensioning device. Accordingly, in one embodiment, when hyperextended, the tensioning device will cause the electronic module extensions 4507, 4508 to move back towards either the open position or the closed position with a closing force 4602.

Figure 47:
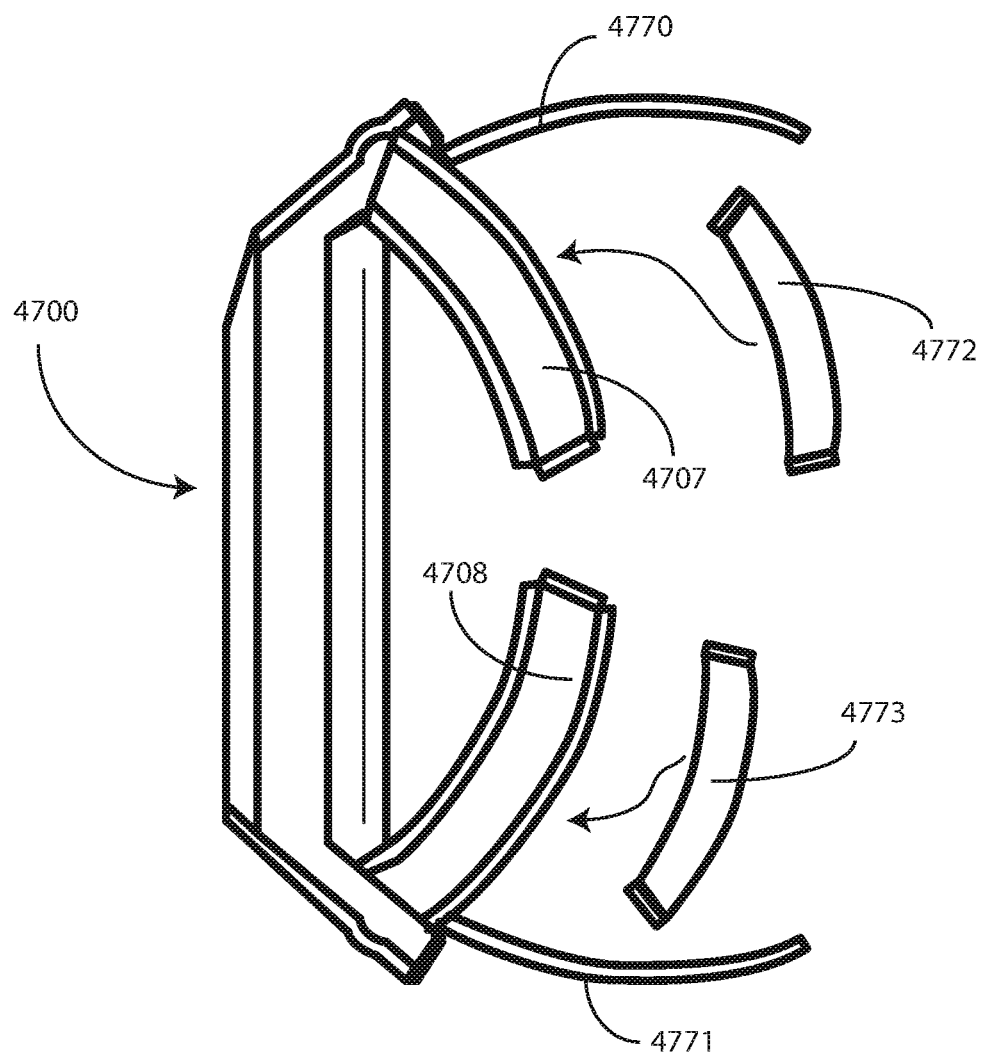
FIG. 47 illustrates a detachable electronic module having battery replacement doors on the electronic module extensions, where removable batteries can be replaced by a user in accordance with one or more embodiments of the invention.

Turning to FIG. 47, illustrated therein is yet another detachable electronic module 4700 having electronic module extensions 4707, 4708 configured in accordance with embodiments of the invention. In FIG. 47, each electronic module extension 4707, 4708 has an electronic module extension battery door 4770, 4771. A user may open each electronic module extension battery door 4770, 4771 to selectively replace the batteries 4772, 4773 as needed. In one embodiment, the batteries 4772, 4773 are rechargeable batteries. Accordingly, a user can remove the batteries 4772, 4773, couple them to a charger, and charge them for subsequent use. (As noted above, in other embodiments, the user may couple the entire detachable electronic module to a charger without the need of removing any battery.) In another embodiment, the batteries 4772, 4773 are primary batteries configured for single use. As shown in FIG. 47, each battery 4772, 4773 of this embodiment has a geometric shape that is complementary to the geometric shapes of the electronic module extension 4707, 4708.

The electronic module extension battery doors 4770, 4771, where included, offer a couple of advantageous features to a user. First and foremost, a user may simply replace the batteries 4772, 4773 rather than having to couple the entire detachable electronic module 4700 to a charger. Accordingly, a user can swap batteries 4772, 4773 and continue using the device, rather than having to discontinue use and wait for a predetermined charging time to recharge the batteries.

Figure 48:
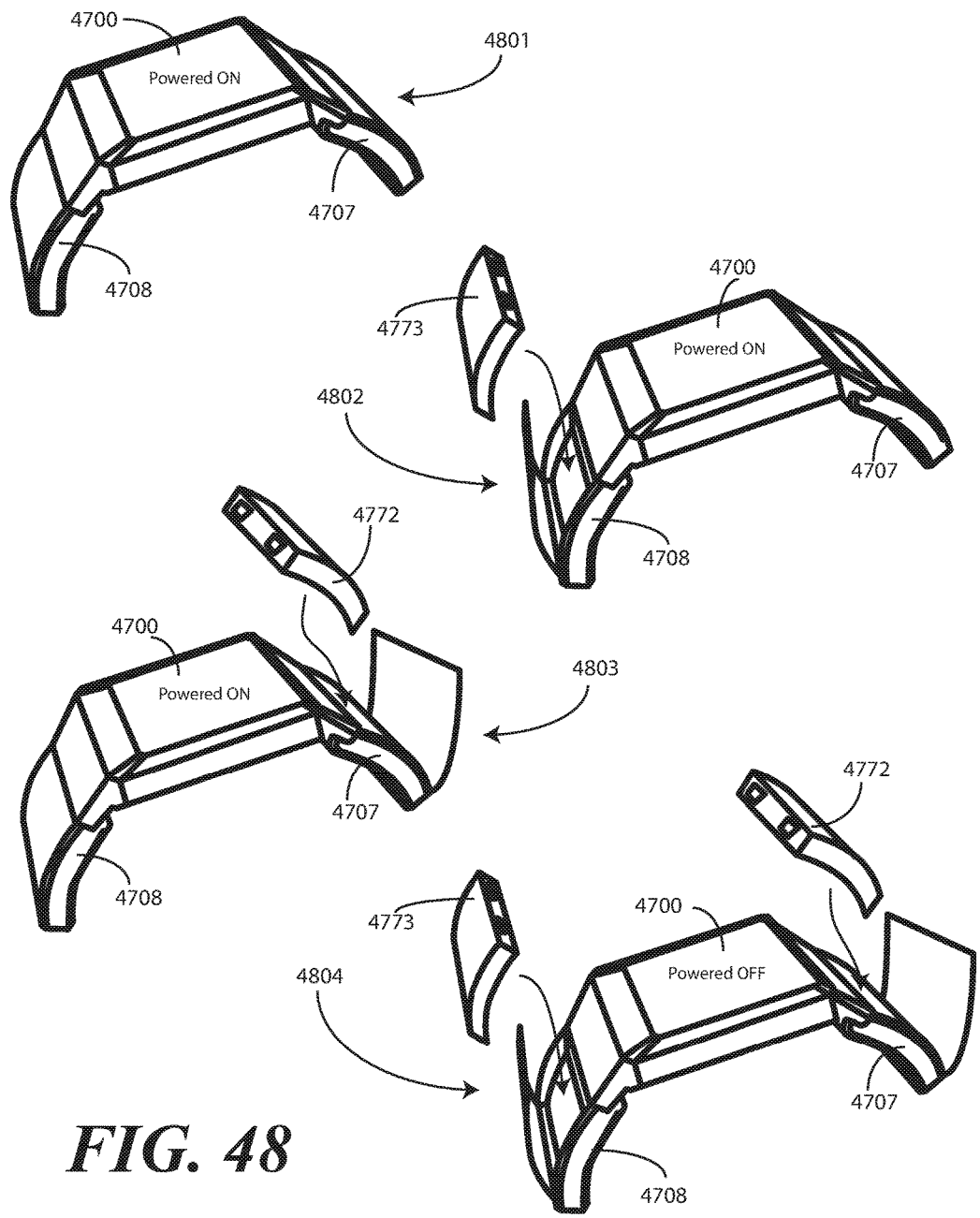
FIG. 48 illustrates operational states of one explanatory detachable electronic module having battery replacement doors and user-replaceable batteries configured in accordance with one or more embodiments of the invention.

As second advantageous feature is shown in FIG. 48. FIG. 48 illustrates four operational modes of the detachable electronic module 4700 of FIG. 47. In view 4801, each electronic module extension 4707, 4708 has a battery (4773, 4773) disposed therein. Accordingly, the detachable electronic module 4700 is powered ON.

In one or more embodiments, the detachable electronic module 4700 can be powered by a single battery. Thus, a user can "hot swap" one of the batteries without powering down the device. For example, in view 4802, one of the batteries 4773 has been removed from its corresponding electronic module extension 4708. The detachable electronic module 4700 is still powered ON because the other battery (4772) is still disposed within its corresponding electronic module extension 4707, and is powering the detachable electronic module 4700.

Similarly, in view 4803, the other battery 4772 has been removed from its corresponding electronic module extension 4707. The detachable electronic module 4700 is still powered ON because the other battery (4773) is still disposed within its corresponding electronic module extension 4708, and is powering the detachable electronic module 4700. Only when both batteries 4772, 4773 are removed, as shown in view 4804, is the detachable electronic module 4700 powered OFF. The ability to hot-swap batteries is especially advantageous in operational modes such as the health monitoring mode, because a user can selectively replace each battery without powering the device down, and thus without stopping the health monitoring features of the detachable electronic module 4700.

Figure 49:
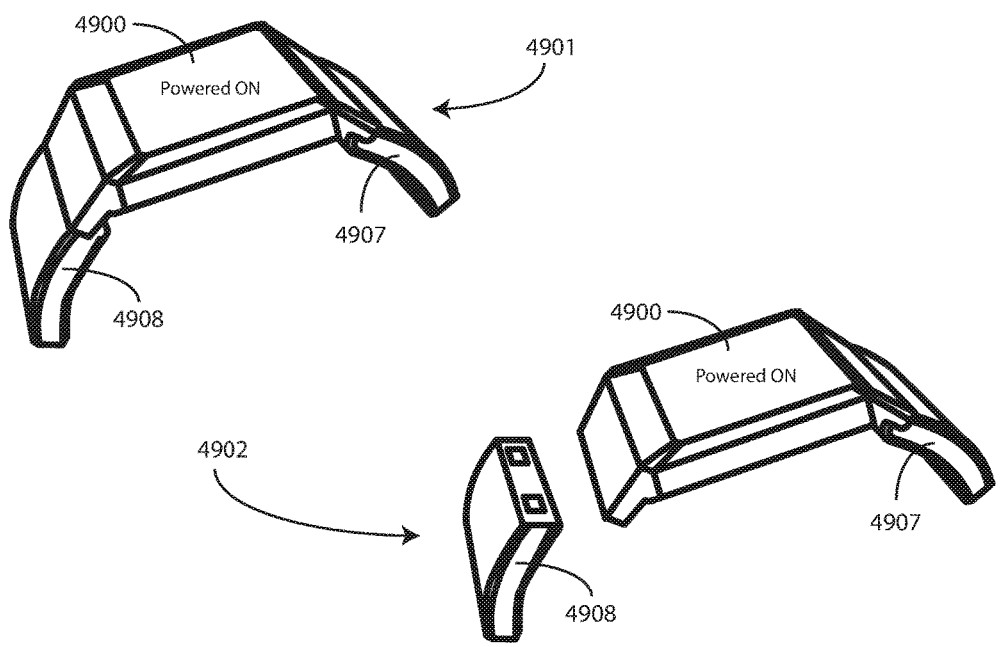
FIG. 49 illustrates operational states of one explanatory detachable electronic module having user-replaceable electronic module extensions configured in accordance with one or more embodiments of the invention.
Figure 49:
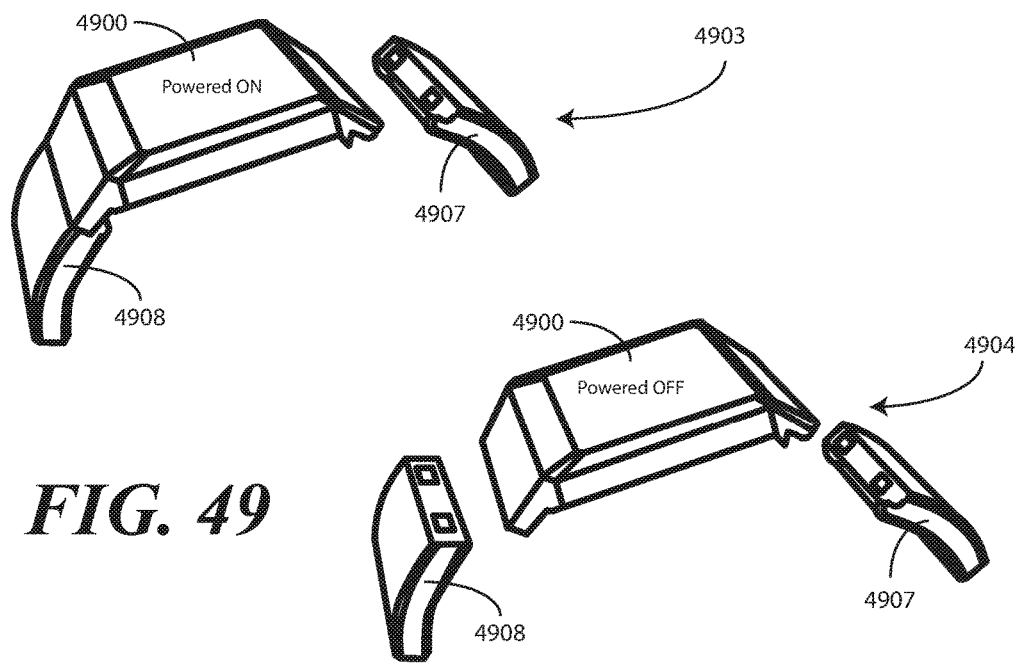

While battery doors are one option for providing a user-replaceable battery feature, in another embodiment, the electronic module extensions have self-contained batteries. Rather than opening a battery door to replace a battery, the user simply detaches one or both electronic module extensions. Such an embodiment is shown in FIG. 49. As with the battery doors, detachable electronic module extensions allow batteries to be hot swapped without powering down the detachable electronic module.

FIG. 49 illustrates four operational modes of the detachable electronic module 4900 having detachable electronic module extensions 4907, 4908. In view 4901, each detachable electronic module extension 4907, 4908 has a battery disposed therein. Each detachable electronic module extension 4907, 4908 is coupled to the detachable electronic module 4900. Accordingly, the detachable electronic module 4900 is powered ON.

As was the case in FIG. 48, in the explanatory embodiment of FIG. 49, a single battery can power the detachable electronic module 4900. Thus, a user can hot swap one of the batteries by detaching the corresponding electronic module extension without powering down the detachable electronic module 4900. For example, in view 4902, one of the detachable electronic module extensions 4908 has been removed from the detachable electronic module 4900. The detachable electronic module 4900 is still powered ON because the other detachable electronic module extension 4907 and its corresponding battery are still attached and powering the detachable electronic module 4900.

Similarly, in view 4903, the other detachable electronic module extension 4907 has been removed from the detachable electronic module 4900. However, the detachable electronic module 4900 is still powered ON because the other detachable electronic module extension 4908, with its corresponding integrated battery, is still attached to the detachable electronic module 4900 and is still powering the detachable electronic module 4900. Only when both detachable electronic module extensions 4907, 4908 are removed, as shown in view 4904, is the detachable electronic module 4900 powered OFF.

As shown and described above, methods and apparatuses configured in accordance with embodiments of the invention provide user input devices for altering the presentation orientation of visual output on a display. When non-user events are detected, the presentation orientation can revert to an initial orientation. In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. For example, predetermined rotation amount described above occurred at 180-degree intervals. However, other arrangements could be used, such as rotation by 90-degree intervals in response to user actuation of hardware elements. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A wearable electronic apparatus comprising:
a strap configured to perform operations independently or in connection with a detachable electronic module, the operations comprising storing one or more types of wellness information in one or more computer-readable storage media disposed in the strap, the strap comprising:
one or more processors;
the one or more computer-readable storage media; and
an attachment bay;
the detachable electronic module, the detachable electronic module configured to mate with the strap at the attachment bay; and
one or more electrical couplings disposed in the attachment bay, the one or more electrical couplings configured to mate with one or more complimentary electrical couplings disposed in the detachable electronic module, the strap configured to perform the operations independently when the one or more electrical couplings do not mate with the one or more complimentary electrical couplings disposed in the detachable electronic module, the strap further configured to perform the operations in connection with the detachable electronic module when the one or more electrical couplings and the one or more complimentary electrical couplings mate together.

2. The wearable electronic apparatus of claim 1, wherein the detachable electronic module further comprises:
one or more other processors;
one or more other computer-readable storage media; and
the one or more complimentary electrical couplings disposed in the detachable electronic module configured to mate with the one or more electrical couplings disposed in the attachment bay.

3. The wearable electronic apparatus of claim 2, wherein the one or more other computer-readable storage media include instructions stored thereon that, responsive to execution by the one or more other processors, implement a health-monitoring mode configured to:
sense one or more other types of wellness information from one or more wellness sensors disposed in the strap;
store the one or more other types of wellness information; and
pass the one or more other types of wellness information to one or more wellness applications.

4. The wearable electronic apparatus of claim 1, wherein the one or more computer-readable storage media include instructions stored thereon that, responsive to execution by the one or more processors, implement a health-monitoring mode configured to:
sense the one or more types of wellness information from one or more wellness sensors disposed in the strap;
pass the one or more types of wellness information to one or more wellness applications.

5. The wearable electronic apparatus of claim 4, wherein the one or more wellness sensors comprise a heart monitor, a moisture detector, a temperature monitor, a pulse monitor, or a galvanic device configured to monitor electric current.

6. The wearable electronic apparatus of claim 4, wherein the health-monitoring mode is configured to monitor vital signals corresponding to the one or more other types of wellness information upon predetermined criteria.

7. The wearable electronic apparatus of claim 1, the strap further comprising a display.

8. The wearable electronic apparatus of claim 7, wherein the display is flexible and covers a portion of an outer surface of the strap.

9. The wearable electronic apparatus of claim 7, wherein the display is configured to present a color based on input from a light sensor of the detachable electronic module.

10. The wearable electronic apparatus of claim 1, further comprising a communication circuit configured to communicate with:
one or more local area networks;
a global positioning system; or
one or more telephony networks.

11. A method performed by a mobile electronic apparatus comprising:
sensing one or more types of wellness information from one or more wellness sensors disposed in a strap, the strap configured to perform operations independently when one or more electrical couplings disposed in an attachment bay of the strap do not mate with one or more complimentary electrical couplings disposed in a detachable electronic module, the strap further configured to perform the operations in connection with the detachable electronic module when the one or more electrical couplings and the one or more complimentary electrical couplings mate together, the detachable electronic module configured to mate with the strap at the attachment bay;
performing the operations, the operations comprising storing the one or more types of wellness information in one or more computer-readable storage media disposed in the strap; and
passing the one or more types of wellness information to one or more wellness applications.

12. The method performed in the mobile electronic apparatus of claim 11, further comprising, based on the sensed one or more types of wellness information, determining a wellness condition.

13. The method performed in the mobile electronic apparatus of claim 12, further comprising communicating the determined wellness condition to a third party.

14. The method performed in the mobile electronic apparatus of claim 12, wherein the strap further comprises communication circuitry configured to communicate with a global positioning system and a communication of the determined wellness condition further comprises a location of the strap.

15. The method performed in the mobile electronic apparatus of claim 14, wherein the communication of the determined wellness condition further comprises an indication of a fall of a user, an automobile accident of the user, an extended lack of motion of the user, or the user being asleep.

16. The method performed in the mobile electronic apparatus of claim 11, further comprising, based on the sensed one or more types of wellness information, providing wellness reminders or health reminders.

17. The method performed in the mobile electronic apparatus of claim 16, wherein the wellness reminders or the health reminders comprise when a user should ingest a medicine or when the user should exercise.

18. A system comprising:
a strap comprising:
one or more processors;
one or more computer-readable storage media;
one or more wellness sensors; and an attachment bay;
one or more electrical couplings disposed in the attachment bay, the one or more electrical couplings configured to mate with one or more complimentary electrical couplings disposed in a detachable electronic module, the strap configured to perform operations independently when the one or more electrical couplings do not mate with the one or more complimentary electrical couplings disposed in the detachable electronic module, the operations comprising storing one or more types of wellness information in the one or more computer-readable storage media disposed in the strap, the strap further configured to perform the operations in connection with the detachable electronic module when the one or more electrical couplings and the one or more complimentary electrical couplings mate together; and
the detachable electronic module comprising:
one or more other processors;
one or more other computer-readable storage media; and
the one or more complimentary electrical couplings disposed in the detachable electronic module configured to mate with the one or more electrical couplings disposed in the attachment bay.

19. The system of claim 18, wherein the one or more computer-readable storage media include instructions stored thereon that, responsive to execution by the one or more processors, implement a health-monitoring mode configured to:
sense the one or more types of wellness information from the one or more wellness sensors disposed in the strap;
pass the one or more types of wellness information to one or more wellness applications.

20. The system of claim 18, wherein the one or more other computer-readable storage media include instructions stored thereon that, responsive to execution by the one or more other processors, implement a health-monitoring mode configured to:
- sense one or more other types of wellness information from the one or more wellness sensors disposed in the strap;
- store the one or more other types of wellness information; and
- pass the one or more other types of wellness information to one or more wellness applications.

* * * * *

UNITED STATES PATENT AND TRADEMARK OFFICE
CERTIFICATE OF CORRECTION

PATENT NO. : 10,387,020 B2
APPLICATION NO. : 15/876860
DATED : August 20, 2019
INVENTOR(S) : Patrick Cauwels et al.

Page 1 of 1

It is certified that error appears in the above-identified patent and that said Letters Patent is hereby corrected as shown below:

In the Claims

Column 41, Lines 19 and 20, Claim 4 after "strap;" before "pass" insert --and--

Column 42, Lines 63 and 64, Claim 19 after "strap;" before "pass" insert --and--

Signed and Sealed this
Seventeenth Day of September, 2019

Andrei Iancu
*Director of the United States Patent and Trademark Office*